(12) United States Patent
Remy et al.

(10) Patent No.: US 12,286,475 B2
(45) Date of Patent: Apr. 29, 2025

(54) ANTI-GPRC5D ANTIBODIES AND COMPOSITIONS

(71) Applicant: SANOFI, Paris (FR)

(72) Inventors: Elisabeth Remy, Paris (FR); Klervi Desrumeaux, Paris (FR); Helene Bonnevaux, Paris (FR); Marco Meloni, Paris (FR); Angela Virone-Oddos, Paris (FR); Marielle Chiron Blondel, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 18/790,955

(22) Filed: Jul. 31, 2024

(65) Prior Publication Data

US 2025/0042993 A1 Feb. 6, 2025

(30) Foreign Application Priority Data

Jul. 31, 2023 (EP) .................................. 23315301
Mar. 1, 2024 (EP) .................................. 24160978

(51) Int. Cl.
*C07K 16/28* (2006.01)
*A61P 35/00* (2006.01)

(52) U.S. Cl.
CPC .............. *C07K 16/28* (2013.01); *A61P 35/00* (2018.01); *C07K 2317/33* (2013.01); *C07K 2317/52* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2004/0110226 A1 | 6/2004 | Lazar et al. | |
| 2004/0132101 A1 | 7/2004 | Lazar et al. | |
| 2022/0356266 A1 | 11/2022 | Ganesan et al. | |

FOREIGN PATENT DOCUMENTS

| | | |
|---|---|---|
| WO | 2003/062401 A2 | 7/2003 |
| WO | 2004/029207 A2 | 4/2004 |
| WO | 2008/140603 A2 | 11/2008 |
| WO | 2011/122011 A2 | 10/2011 |
| WO | 2012/073992 A1 | 6/2012 |
| WO | 2012/133782 A1 | 10/2012 |
| WO | 2013/118858 A1 | 8/2013 |
| WO | 2013/187495 A1 | 12/2013 |
| WO | 2014/153063 A1 | 9/2014 |
| WO | 2014/153111 A2 | 9/2014 |
| WO | 2015/035215 A1 | 3/2015 |
| WO | 2016/090329 A2 | 6/2016 |
| WO | 2018/178122 A1 | 10/2018 |
| WO | 2021/018925 A1 | 2/2021 |
| WO | 2022/148370 A1 | 7/2022 |
| WO | 2022/212470 A2 | 10/2022 |
| WO | 2022/249146 A1 | 12/2022 |
| WO | 2023/015298 A1 | 2/2023 |
| WO | 2023/030272 A1 | 3/2023 |
| WO | 2023/043123 A1 | 3/2023 |
| WO | 2023/043124 A1 | 3/2023 |
| WO | 2023/043125 A1 | 3/2023 |
| WO | 2023/068710 A1 | 4/2023 |
| WO | 2023/070100 A1 | 4/2023 |
| WO | 2023/125888 A1 | 7/2023 |
| WO | 2023/205659 A2 | 10/2023 |
| WO | 2023/244276 A2 | 12/2023 |

OTHER PUBLICATIONS

Jacobsen et al., "Engineering an IgG Scaffold Lacking Effector Function with Optimized Developability," J Biol Chem. (2017) 292(5):1865-75.
Krahn et al., "Inhibition of glycosylation on a camelid antibody uniquely affects its FcyRI binding activity," Eur J Pharm Sci. (2017) 96:428-39.
Lazar et al., "Engineered antibody Fc variants with enhanced effector function," PNAS (2006) 103:4005-10.
Pereira et al., "The 'less-is-more' in therapeutic antibodies: afucosylated anti-cancer antibodies with enhanced antibody-dependent cellular cytotoxicity," MAbs (2018) 10(5):693-711.
Yamane-Ohnuki et al., "Establishment of FUT8 knockout Chinese hamster ovary cells: an ideal host cell line for producing completely defucosylated antibodies with enhanced antibody-dependent cellular cytotoxicity," Biotechnol Bioeng. (2004) 87:614-22.
Hartley-Brown et al., "Monoclonal Antibodies in Myeloma: Optimizing Targeted Therapy," Cancer Journal (2021) 27 (3):222-30.

*Primary Examiner* — Ruixiang Li
(74) *Attorney, Agent, or Firm* — Steptoe LLP; Z. Ying Li; Wyan-Ching M. Lee

(57) ABSTRACT

The present disclosure provides antigen-binding proteins specifically binding GPRC5D, as well as respective antibodies in enhanced ADCC formats, and methods of using them to treat cancers such as multiple myeloma.

20 Claims, 17 Drawing Sheets

Specification includes a Sequence Listing.

E

SEQUENCE LISTING

```
Sequence total quantity: 18
SEQ ID NO: 1              moltype = AA  length = 8
FEATURE                   Location/Qualifiers
REGION                    1..8
                          note = Synthetic: 11 HCDR1
source                    1..8
                          mol_type = protein
                          organism = synthetic construct
SEQUENCE: 1
GFTVSSNY                                                                  8

SEQ ID NO: 2              moltype = AA  length = 7
FEATURE                   Location/Qualifiers
REGION                    1..7
                          note = Synthetic: 11 HCDR2
source                    1..7
                          mol_type = protein
                          organism = synthetic construct
SEQUENCE: 2
IYSGGST                                                                   7

SEQ ID NO: 3              moltype = AA  length = 16
FEATURE                   Location/Qualifiers
REGION                    1..16
                          note = Synthetic: 11 HCDR3
source                    1..16
                          mol_type = protein
                          organism = synthetic construct
SEQUENCE: 3
ARGFLAFGRY YYGMDV                                                        16

SEQ ID NO: 4              moltype = AA  length = 8
FEATURE                   Location/Qualifiers
REGION                    1..8
                          note = Synthetic: 11 LCDR1
source                    1..8
                          mol_type = protein
                          organism = synthetic construct
SEQUENCE: 4
SSNIGSNY                                                                  8

SEQ ID NO: 5              moltype =     length =
SEQUENCE: 5
000

SEQ ID NO: 6              moltype = AA  length = 11
FEATURE                   Location/Qualifiers
REGION                    1..11
                          note = Synthetic: 11 LCDR3
source                    1..11
                          mol_type = protein
                          organism = synthetic construct
SEQUENCE: 6
AAWDDSLSGD V                                                             11
```

```
SEQ ID NO: 7              moltype = AA   length = 122
FEATURE                   Location/Qualifiers
REGION                    1..122
                          note = Synthetic: 11 VH
source                    1..122
                          mol_type = protein
                          organism = synthetic construct
SEQUENCE: 7
EVQLVESGGG LVQPGGSLRL SCAASGFTVS SNYMSWVRQA PGKGLEWVSV IYSGGSTYYA    60
DSVKGRFTIS RDNSKNTLYL QMNSLRAEDT AVYYCARGFL AFGRYYYGMD VWGQGTTVTV   120
SS                                                                  122

SEQ ID NO: 8              moltype = AA   length = 110
FEATURE                   Location/Qualifiers
REGION                    1..110
                          note = Synthetic: 11 VL
source                    1..110
                          mol_type = protein
                          organism = synthetic construct
SEQUENCE: 8
QSVLTQPPSA SGTPGQRVTI SCSGSSSNIG SNYVYWYQQL PGTAPKLLIY RNNQRPSGVP    60
DRFSGSKSGT SASLAISGLR SEDEADYYCA AWDDSLSGDV FGGGTKLTVL              110

SEQ ID NO: 9              moltype = AA   length = 451
FEATURE                   Location/Qualifiers
REGION                    1..451
                          note = Synthetic: 11 HC
source                    1..451
                          mol_type = protein
                          organism = synthetic construct
SEQUENCE: 9
EVQLVESGGG LVQPGGSLRL SCAASGFTVS SNYMSWVRQA PGKGLEWVSV IYSGGSTYYA    60
DSVKGRFTIS RDNSKNTLYL QMNSLRAEDT AVYYCARGFL AFGRYYYGMD VWGQGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP G                                  451

SEQ ID NO: 10             moltype = AA   length = 451
FEATURE                   Location/Qualifiers
REGION                    1..451
                          note = Synthetic: 11 HC with Fc mutations
source                    1..451
                          mol_type = protein
                          organism = synthetic construct
SEQUENCE: 10
EVQLVESGGG LVQPGGSLRL SCAASGFTVS SNYMSWVRQA PGKGLEWVSV IYSGGSTYYA    60
DSVKGRFTIS RDNSKNTLYL QMNSLRAEDT AVYYCARGFL AFGRYYYGMD VWGQGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPDVFLFPP KPKDTLMISR TPEVTCVVVD VSHEDPEVKF NWYVDGVEVH NAKTKPCEEQ   300
YNSTYRCVSV LTVLHQDWLN GKEYKCKVSN KALPAPEEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP G                                  451

SEQ ID NO: 11             moltype = AA   length = 216
FEATURE                   Location/Qualifiers
REGION                    1..216
                          note = Synthetic: 11 LC
source                    1..216
                          mol_type = protein
                          organism = synthetic construct
SEQUENCE: 11
QSVLTQPPSA SGTPGQRVTI SCSGSSSNIG SNYVYWYQQL PGTAPKLLIY RNNQRPSGVP    60
DRFSGSKSGT SASLAISGLR SEDEADYYCA AWDDSLSGDV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 12             moltype = AA   length = 345
FEATURE                   Location/Qualifiers
REGION                    1..345
                          note = misc_feature - human GPRC5D
source                    1..345
                          mol_type = protein
                          organism = Homo sapiens
SEQUENCE: 12
MYKDCIESTG DYFLLCDAEG PWGIILESLA ILGIVVTILL LLAFLFLMRK IQDCSQWNVL    60
```

```
PTQLLFLLSV LGLFGLAFAF IIELNQQTAP VRYFLFGVLF ALCFSCLLAH ASNLVKLVRG   120
CVSFSWTTIL CIAIGCSLLQ IIIATEYVTL IMTRGMMFVN MTPCQLNVDF VVLLVYVLFL   180
MALTFFVSKA TFCGPCENWK QHGRLIFITV LFSIIIWVVW ISMLLRGNPQ FQRQPQWDDP   240
VVCIALVTNA WVFLLLYIVP ELCILYRSCR QECPLQGNAC PVTAYQHSFQ VENQELSRAR   300
DSDGAEEDVA LTSYGTPIQP QTVDPTQECF IPQAKLSPQQ DAGGV                   345

SEQ ID NO: 13          moltype = AA   length = 175
FEATURE                Location/Qualifiers
REGION                 1..175
                       note = Synthetic: (Gly4 Ser)n, n = 1 to 35
VARIANT                6..175
                       note = "GGGGS" may or may not be present
source                 1..175
                       mol_type = protein
                       organism = synthetic construct
SEQUENCE: 13
GGGGSGGGGS GGGGSGGGGS GGGGSGGGGS GGGGSGGGGS GGGGSGGGGS GGGGSGGGGS    60
GGGGSGGGGS GGGGSGGGGS GGGGSGGGGS GGGGSGGGGS GGGGSGGGGS GGGGSGGGGS   120
GGGGSGGGGS GGGGSGGGGS GGGGSGGGGS GGGGSGGGGS GGGGSGGGGS GGGGS        175

SEQ ID NO: 14          moltype = AA   length = 363
FEATURE                Location/Qualifiers
REGION                 1..363
                       note = misc_feature - Human GPRC5A
source                 1..363
                       mol_type = protein
                       organism = Homo sapiens
SEQUENCE: 14
MATTVPDGCR NGLKSKYYRL CDKAEAWGIV LETVATAGVV TSVAFMLTLP ILVCKVQDSN    60
RRKMLPTQFL FLLGVLGIFG LTFAFIIGLD GSTGPTRFFL FGILFSICFS CLLAHAVSLT   120
KLVRGRKPLS LLVILGLAVG FSLVQDVIAI EYIVLTMNRT NVNVFSELSA PRRNEDFVLL   180
LTYVLFLMAL TFLMSSFTPC GSFTGWKRHG AHIYLTMLLS IAIWVAWITL LMLPDFDRRW   240
DDTILSSALA ANGWVFLLAY VSPEFWLLTK QRNPMDYPVE DAFCKPQLVK KSYGVENRAY   300
SQEEITQGFE ETGDTLYAPY STHFQLQNQP PQKEFSIPRA HAWPSPYKDY EVKKEGSEYM   360
PME                                                                363

SEQ ID NO: 15          moltype = AA   length = 356
FEATURE                Location/Qualifiers
REGION                 1..356
                       note = Synthetic: human GPRC5D-human GPRC5A chimera (N-term)
source                 1..356
                       mol_type = protein
                       organism = synthetic construct
SEQUENCE: 15
MATTVPDGCR NGLKSKYYRL CDKAEAWGIV LESLAILGIV VTILLLLAFL FLMRKIQDCS    60
QWNVLPTQLL FLLSVLGLFG LAFAFIIELN QQTAPVRYFL FGVLFALCFS CLLAHASNLV   120
KLVRGCVSFS WTTILCIAIG CSLLQIIIAT EYVTLIMTRG MMFVNMTPCQ LNVDFVVLLV   180
YVLFLMALTF FVSKATFCGP CENWKQHGRL IFITVLFSII IWVVWISMLL RGNPQFQRQP   240
QWDDPVVCIA LVTNAWVFLL LYIVPELCIL YRSCRQECPL QGNACPVTAY QHSFQVENQE   300
LSRARDSDGA EEDVALTSYG TPIQPQTVDP TQECFIPQAK LSPQQDAGGV EYMPME       356

SEQ ID NO: 16          moltype = AA   length = 351
FEATURE                Location/Qualifiers
REGION                 1..351
                       note = Synthetic: human GPRC5D-human GPRC5A chimera (85-93)
source                 1..351
                       mol_type = protein
                       organism = synthetic construct
SEQUENCE: 16
MYKDCIESTG DYFLLCDAEG PWGIILESLA ILGIVVTILL LLAFLFLMRK IQDCSQWNVL    60
PTQLLFLLSV LGLFGLAFAF IIELDGSTGP TRFFLFGVLF ALCFSCLLAH ASNLVKLVRG   120
CVSFSWTTIL CIAIGCSLLQ IIIATEYVTL IMTRGMMFVN MTPCQLNVDF VVLLVYVLFL   180
MALTFFVSKA TFCGPCENWK QHGRLIFITV LFSIIIWVVW ISMLLRGNPQ FQRQPQWDDP   240
VVCIALVTNA WVFLLLYIVP ELCILYRSCR QECPLQGNAC PVTAYQHSFQ VENQELSRAR   300
DSDGAEEDVA LTSYGTPIQP QTVDPTQECF IPQAKLSPQQ DAGGVEYMPM E            351

SEQ ID NO: 17          moltype = AA   length = 353
FEATURE                Location/Qualifiers
REGION                 1..353
                       note = Synthetic: human GPRC5D-human GPRC5A chimera
                         (145-167)
source                 1..353
                       mol_type = protein
                       organism = synthetic construct
SEQUENCE: 17
MYKDCIESTG DYFLLCDAEG PWGIILESLA ILGIVVTILL LLAFLFLMRK IQDCSQWNVL    60
PTQLLFLLSV LGLFGLAFAF IIELNQQTAP VRYFLFGVLF ALCFSCLLAH ASNLVKLVRG   120
CVSFSWTTIL CIAIGCSLLQ IIIAIEYIVL TMNRTNVNVF SELSAPRRNV DFVVLLYYVL   180
FLMALTFFVS KATFCGPCEN WKQHGRLIFI TVLFSIIIWV VWISMLLRGN PQFQRQPQWD   240
```

```
DPVVCIALVT NAWVFLLLYI VPELCILYRS CRQECPLQGN ACPVTAYQHS FQVENQELSR    300
ARDSDGAEED VALTSYGTPI QPQTVDPTQE CFIPQAKLSP QQDAGGVEYM PME           353

SEQ ID NO: 18          moltype = AA  length = 347
FEATURE                Location/Qualifiers
REGION                 1..347
                       note = Synthetic: human GPRC5D-human GPRC5A chimera
                       (226-239)
source                 1..347
                       mol_type = protein
                       organism = synthetic construct
SEQUENCE: 18
MYKDCIESTG DYFLLCDAEG PWGIILESLA ILGIVVTILL LLAFLFLMRK IQDCSQWNVL    60
PTQLLFLLSV LGLFGLAFAF IIELNQQTAP VRYFLFGVLF ALCFSCLLAH ASNLVKLVRG    120
CVSFSWTTIL CIAIGCSLLQ IIIATEYVTL IMTRGMMFVN MTPCQLNVDF VVLLVYVLFL    180
MALTFFVSKA TFCGPCENWK QHGRLIFITV LFSIIIWVVW ISMLLLPDFD RRWDDPVVCI    240
ALVTNAWVFL LLYIVPELCI LYRSCRQECP LQGNACPVTA YQHSFQVENQ ELSRARDSDG    300
AEEDVALTSY GTPIQPQTVD PTQECFIPQA KLSPQQDAGG VEYMPME                  347
```

ANTI-GPRC5D ANTIBODIES AND COMPOSITIONS

CROSS-REFERENCE TO RELATED APPLICATIONS

This application claims priority to EP Patent Application No. 23315301.4, filed Jul. 31, 2023, and EP Patent Application No. 24160978.3, filed Mar. 1, 2024. The disclosures of those priority applications are incorporated by reference herein in their entirety.

SEQUENCE LISTING

The instant application contains a Sequence Listing which has been submitted electronically in XML format and is part of the specification, and is hereby incorporated by reference herein in its entirety. The electronic copy of the Sequence Listing, created on Jul. 3, 2024, is named 122548.US016_SL.xml and is 26,432 bytes in size.

BACKGROUND OF THE INVENTION

Multiple myeloma (MM) is the second most common hematological malignancy, and is characterized by uncontrolled proliferation of plasma cells in the bone marrow. Patients present with symptoms such as weakness, fatigue, anemia, weight loss, immunosuppression, hypercalcemia, and bone pain. While therapies for MM have improved in recent years, it remains a difficult-to-treat heterogeneous disease and is considered incurable.

GPRC5D is an orphan G protein-coupled receptor (GPCR) strongly expressed on malignant plasma cells in patients with MM. Nearly 80% MM tumor cells express GPRC5D, while normal tissue expression is mainly restricted to plasma cells and hair follicles. Due to its limited expression in healthy tissues, GPRC5D has been identified as a potential immunotherapeutic target for treatment of MM.

SUMMARY OF THE INVENTION

The present invention provides an antigen-binding protein, in particular an antibody or an antigen-binding portion thereof that comprises HCDR1-3 and LCDR1-3 amino acid sequences of SEQ ID NOs: 1-6, respectively. In some embodiments that antigen-binding protein comprises two variable domains, the first variable domain comprises a HCDR1 of SEQ ID NO: 1, a HCDR2 of SEQ ID NO: 2 and a HCDR3 of SEQ ID NO: 3, and the second variable domain comprises a LCDR1 of SEQ ID NO: 4, a LCDR2 of SEQ ID NO: 5 and a LCDR3 of SEQ ID NO: 6. In some embodiments, the antigen-binding protein, in particular an antibody, binds to human GPRC5D, to cynomolgus GPRC5D, or to both. Also provided is a binding protein comprising the antigen binding protein of the invention, in particular an antibody or an antigen-binding portion thereof.

In some embodiments, the antigen-binding protein, in particular the antibody described herein comprises a heavy chain variable domain (VH) amino acid sequence and a light chain variable domain (VL) amino acid sequence that are at least 90%, 91%, 92% 93%, 94%, 95%, 96%, 97%, 98%, or 99% (e.g., at least 90%) identical to the amino acid sequences of SEQ ID NOs: 7 and 8, respectively. In some of these embodiments the HCDR1 to HCDR3 and LCDR1 to LCDR3 have the amino acid sequences according to SEQ ID NO: 1 to 6, respectively, i.e. the sequence variations are outside the HCDR1 to HCDR3 and LCDR1 to LCDR3. In certain embodiments, the antigen-binding protein, in particular the antibody comprises a VH comprising SEQ ID NO: 7 and a VL comprising SEQ ID NO: 8. According to one embodiment, the antigen-binding protein, in particular the antibody may be of human IgG isotype, preferably of human $IgG_1$ isotype subclass.

In some embodiments, the antigen binding protein, in particular the antibody comprises a heavy chain (HC) variable domain amino acid sequence and a light chain (LC) variable domain amino acid sequence that are at least 90%, 91%, 92%, 93%, 94%, 95%, 96%, 97%, 98%, or 99% (e.g., at least 90%) identical to the amino acid sequences of SEQ ID NOs: 9 and 11, respectively. In some of these embodiments the HCDR1 to HCDR3 and LCDR1 to LCDR3 have the amino acid sequences according to SEQ ID NO: 1 to 6, respectively, i.e. the sequence variations are outside the HCDR1 to HCDR3 and LCDR1 to LCDR3. In particular embodiments, the antigen binding protein, in particular the antibody comprises an HC comprising SEQ ID NO: 9 and an LC comprising SEQ ID NO: 11.

In some embodiments, the antigen-binding protein, in particular the antibody described herein comprises at least one Fc domain mutation, preferably a mutation that enhances binding of the antigen binding protein, in particular the antibody described herein to human FcγRIIIa. The Fc domain mutation may be at, for example, position 239 (e.g., S239D), position 332 (e.g., I332E), or both (e.g., S239D and I332E), wherein the residues are numbered according to Eu numbering (Edelman, G. M. et al., *Proc. Natl. Acad. USA*, 63, 78-85 (1969)). According to a particular embodiment, the Fc domain mutation is S239D, I332E or the double mutation S239D and I322E, more preferably S239D and I332E.

In some embodiments, the antigen-binding protein, in particular the antibody described herein comprises at least one Fc domain mutation that enhances antibody stability. In certain embodiments, the antibody comprises a pair of Fc domain mutations to cysteines, for example at positions 292 and 302 (e.g., R292C and V302C), wherein the residues are numbered according to Eu numbering. According to a preferred embodiment, the antigen-binding protein, in particular the antibody described herein comprises the Fc domain mutations R292C and V302C.

According to a particular embodiment, the antigen-binding protein, in particular the antibody described herein comprises the Fc mutations S239D, I332E, R292C and V302C, wherein the residues are numbered according to Eu numbering.

In certain embodiments, the antigen-binding protein, in particular the antibody described herein comprises an HC amino acid sequence and an LC amino acid sequence that are at least 90%, 91%, 92%, 93%, 94%, 95%, 96%, 97%, 98%, or 99% (e.g., at least 90%) identical to the amino acid sequences of SEQ ID NOs: 10 and 11, respectively. In some of these embodiments the HCDR1 to HCDR3 and LCDR1 to LCDR3 have the amino acid sequences according to SEQ ID NO: 1 to 6, respectively, i.e. the sequence variations are outside the CDRs. In particular embodiments, the antigen-binding protein, in particular the antibody comprises a heavy chain comprising SEQ ID NO: 10 and a light chain comprising SEQ ID NO: 11.

According to a specific embodiment, the antigen-binding protein, in particular the antibody described herein comprises a Fc that is afucosylated Fc.

In some embodiments, the antigen-binding protein, in particular antibody or an antigen-binding portion thereof described herein, or a binding protein comprising said antibody or antigen-binding portion, has at least one property selected from:
a) binds specifically to cells that express human GPRC5D;
b) binds specifically to cells that express cynomolgus GPRC5D;
c) binds to cells that express human FcγRIIIa;
d) binds to cells that express cynomolgus FcγRIIIa;
e) binds, preferably specifically to human GPRC5D with the amino acid sequence of SEQ ID NO: 12 or having an N-terminal deletion of up to 20 amino acids, such as an N-terminal deletion of 1, 2, 3, 4, 5, 6, 7, 8, 9, 10, 11, 12, 13, 14, 15, 16, 17, 18, 19 or 20 amino acids;
f) binds, preferably specifically to SEQ ID NO: 15;
g) binds, preferably specifically to SEQ ID NO: 16;
h) binds, preferably specifically to SEQ ID NO: 17;
i) promotes NK cell engagement;
j) promotes NK cell degranulation;
k) induces NK cell activation;
l) induces primary plasma cell depletion;
m) promotes lysis of multiple myeloma cells in the presence of NK cells; n) induces no more than a 5-fold increase in IFN-γ, IL-6, and/or TNF-α by peripheral blood mononuclear cells in the presence of GPRC5D-expressing cells;
o) is quantifiable in plasma for at least 28 days in vivo;
p) has a terminal elimination half-life of at least nine days in vivo;
q) does not result in elevation of IFN-γ, IL-8, and TNFα levels in vivo;
r) inhibits tumor growth in vivo;
s) specifically binds to a GPRC5D dimer;
t) shows cross-reactivity in mice; and
u) shows cross-reactivity in cynomolgus monkeys.

The antigen-binding protein, in particular antibody, antigen-binding portion, or the binding protein may have any combination of said properties, or all of said properties.

In some embodiments, the antigen-binding protein or the binding protein comprising an antibody or antigen-binding portion thereof described herein is monospecific, bispecific (e.g., a bispecific T cell engager), or multi-specific. In some embodiments, the antigen-binding protein is a fusion protein, for example, a chimeric antigen receptor (CAR). In some embodiments, the antigen-binding protein is a T cell receptor (TCR) or part of a TCR.

The present invention also provides a pharmaceutical composition comprising an antigen-binding protein, in particular antibody, antigen-binding portion, or binding protein described herein and a pharmaceutically acceptable excipient.

The present invention further provides isolated nucleic acid molecule(s) comprising one or more nucleotide sequences that encode the antigen-binding protein, in particular antibody or antigen binding fragment thereof described herein. Preferably, the nucleotide sequence encodes a protein comprising the first variable domain, e.g. a heavy chain variable domain or heavy chain, and the same or a different nucleotide sequence encodes a protein comprising the second variable domain, e.g. a light chain or light chain variable domain of the antigen-binding portion, in particular the antibody or antigen-binding portion thereof described herein, or comprises (a) nucleotide sequence(s) that encode a binding protein described herein. Further provided are vector(s) comprising the isolated nucleic acid molecule(s), wherein the vector(s) may comprise an expression control sequence. Also provided are one or more host cells comprising the isolated nucleic acid molecule(s), as well as a method for producing the antigen-binding protein, in particular the antibody or antigen-binding portion thereof or a binding protein as described herein, comprising providing the host cell(s), culturing said host cell(s) under conditions suitable for expression of the antigen-binding protein, and isolating the resulting antigen-binding protein from the culture.

The present invention further provides a pharmaceutical composition comprising the antigen-binding protein, the isolated nucleic acid molecule(s), the vector(s), or the host cell(s) described herein, and a pharmaceutically acceptable excipient.

The present invention further provides the antigen-binding protein, the isolated nucleic acid molecule(s), the vector(s), the host cell(s), or the pharmaceutical composition described herein, for use as a medicament. According to a preferred embodiment, the medicament is for use in treating cancer, more preferably wherein the cancer is multiple myeloma, non-Hodgkin's lymphoma, renal cancer, breast cancer, ovarian cancer, or pancreatic cancer. According to a particularly preferred embodiment, the cancer is multiple myeloma (MM). For example, the cancer may be smoldering (asymptomatic) multiple myeloma or active (symptomatic) multiple myeloma. The multiple myeloma may be hyperdiploid (HMM) or non-hyperdiploid or hypodiploid. The myeloma subtype may be, e.g., IgG, IgA, IgM, IgE, or IgD myeloma. Further preferred forms of myeloma include light chain myeloma, non-secretory myeloma, solitary plasmacytoma, multiple solitary plasmacytoma, extramedullary myeloma, and monoclonal gammopathy of undetermined significance (MGUS). According to a particularly preferred embodiment, the cancer is a GPRC5D-positive cancer.

The present disclosure also provides a method for treating cancer in a patient, in particular a human patient in need thereof, comprising administering to said patient a therapeutically effective amount of the antigen-binding protein, in particular the antibody, the antigen-binding portion thereof, the binding protein, or of the pharmaceutical composition as described herein. In certain embodiments, the cancer is multiple myeloma, non-Hodgkin's lymphoma, renal cancer, breast cancer, ovarian cancer, or pancreatic cancer. In particular embodiments, the cancer is multiple myeloma.

It is understood that the present disclosure also provides an antibody, antigen-binding portion thereof, binding protein, or pharmaceutical composition described herein for use in treating a human in need thereof in a therapeutic method described herein. Also provided are uses of the antigen-binding protein, in particular the antibody, the antigen-binding portion thereof, the binding protein, the isolated nucleic acid molecule(s), the vector(s), the host cell(s), or of the pharmaceutical composition described herein for the manufacture of a medicament for treating a patient in need thereof, preferably a patient having cancer. In certain embodiments, the cancer is multiple myeloma, non-Hodgkin's lymphoma, renal cancer, breast cancer, ovarian cancer, or pancreatic cancer. In particular embodiments, the cancer is multiple myeloma.

Other features, objectives, and advantages of the invention are apparent in the detailed description that follows. It should be understood, however, that the detailed description, while indicating embodiments and aspects of the invention, is given by way of illustration only, not limitation. Various changes and modification within the scope of the invention will become apparent to those skilled in the art from the detailed description.

DETAILED DESCRIPTION OF THE INVENTION

Figure 1:
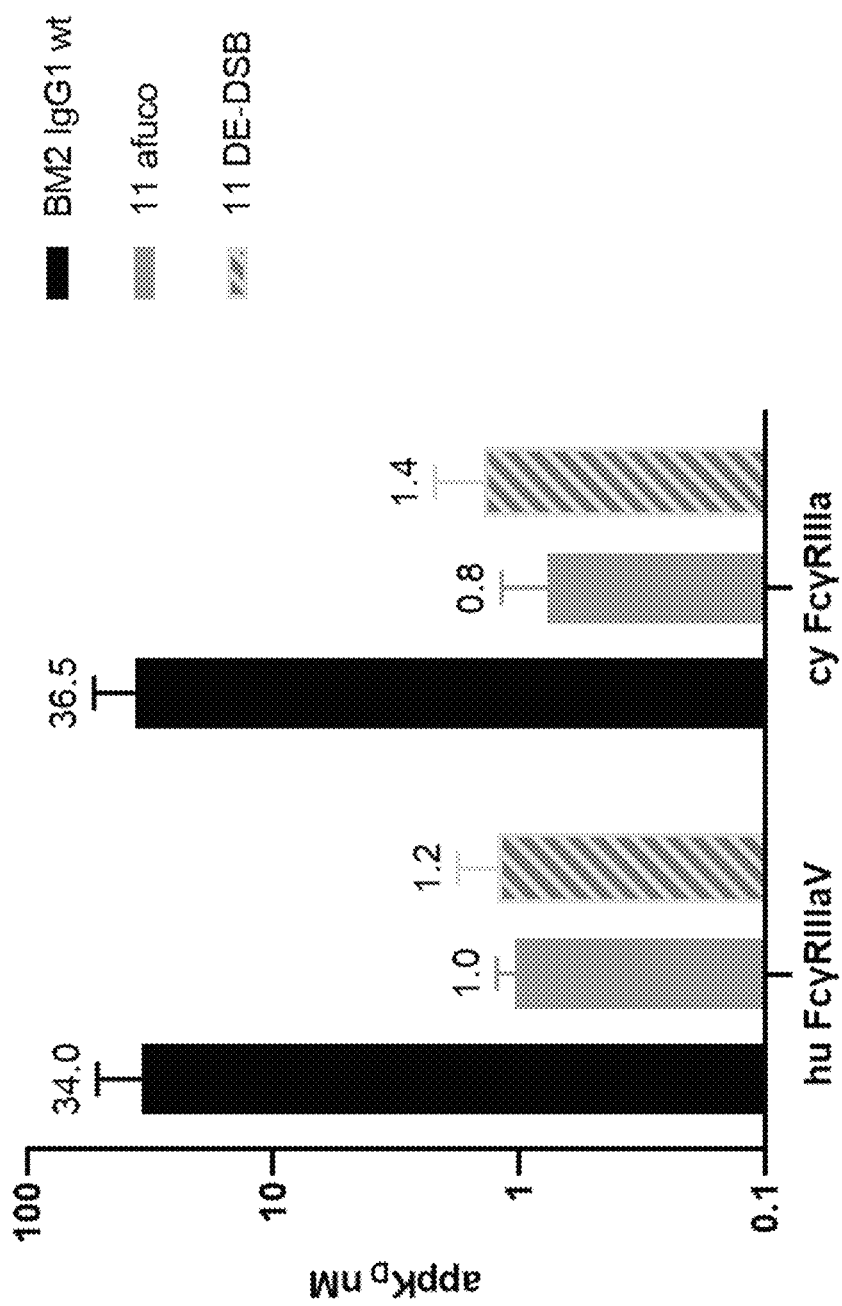
FIG. 1 is a histogram depicting the affinity (apparent $K_D$, or "app$K_D$") for cynomolgus ("cy") and human ("hu") FcγRIIIa-expressing HEK293 T cells of clone 11 in afucosylated ("afuco") and DE-DSB formats as well as comparator anti-GPRC5D antibody Benchmark 2 ("BM2") in IgG$_1$ wildtype ("wt") format. The data represent the mean of three experiments.

The present invention provides new anti-GPRC5D antigen-binding proteins, in particular antibodies that can be used to treat cancer (e.g., multiple myeloma) in a patient, as well as GPRC5D-binding proteins comprising said antibodies or antigen-binding portions of said antibodies. Also provided are pharmaceutical compositions comprising one or more of these antibodies or antigen-binding portions thereof or binding proteins, and use of the antigen-binding proteins, in particular antibodies or antigen-binding portions thereof, binding proteins, and pharmaceutical compositions for treatment of cancer (e.g., multiple myeloma). The antigen-binding proteins, in particular antibodies and antigen-binding portions thereof, binding proteins, and compositions described herein may be used in a method for treating cancer in a patient; may be used for the manufacture of a medicament for treating cancer in a patient; or may be for use in treating cancer in a patient. In a specific embodiment, the present invention provides antigen-binding proteins, in particular antibodies that comprise two variable domains, the first variable domain comprises a HCDR1 of SEQ ID NO: 1, a HCDR2 of SEQ ID NO: 2 and a HCDR3 of SEQ ID NO: 3, and the second variable domain comprises a LCDR1 of SEQ ID NO: 4, a LCDR2 of SEQ ID NO: 5 and a LCDR3 of SEQ ID NO: 6. The antigen-binding protein specifically binds to GPRC5D, as described herein, preferably to human GPRC5D, more preferably to GPRC5D having the amino acid sequence as set forth in SEQ ID NO: 12. The antigen-binding protein of the present invention can be used to treat cancer (e.g., multiple myeloma) in a patient. The antigen-binding protein of the present invention is preferably a GPRC5D-binding protein, such as an antibody or an antigen-binding portions of said antibody.

Also provided are pharmaceutical compositions comprising one or more of these antigen-binding proteins, in particular antibodies or antigen-binding portions thereof or binding proteins, as well as the antigen-binding proteins, in particular antibodies or antigen-binding portions thereof, binding proteins, and pharmaceutical compositions for use in the treatment of cancer (e.g., multiple myeloma). Accordingly, the antigen-binding proteins, in particular antibodies and antigen-binding portions thereof, binding proteins, and compositions described herein may be used in a method for treating cancer in a patient; may be used for the manufacture of a medicament for treating cancer in a patient; or may be for use in treating cancer in a patient.

In some embodiments, the antigen-binding protein of the invention is an anti-GPRC5D antibody having enhanced ADCC activity, which can be used for example as natural killer (NK) cell engagers, i.e., molecules that can simultaneously bind GPRC5D on a target cell (e.g., a malignant plasma cell) and a cell surface molecule (e.g., an Fc receptor) on NK cells. Treatments with such NK cell engagers are expected to be safer than T cell-based treatments (e.g., BiTE (bispecific T cell engager) and CAR-T therapies) because NK cells are less likely to trigger cytokine release syndrome (CRS) or graft-versus-host disease (GVHD), or to cause neurotoxicity. The safer profile of NK cell engagers may in turn result in more convenient administration, with less or no need for observation stay in hospital during active treatment periods.

Before the present invention is described in detail below, it is to be understood that this invention is not limited to the particular methodology, protocols and reagents described herein as these may vary. It is also to be understood that the terminology used herein is for the purpose of describing particular embodiments only and is not intended to limit the scope of the present invention which will be limited only by the appended claims. Unless defined otherwise, all technical and scientific terms used herein have the same meaning as commonly understood by one of ordinary skill in the art.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention. In the event of a conflict between the definitions or teachings of such incorporated references and definitions or teachings recited in the present specification, the text of the present specification takes precedence.

To practice the present invention, unless otherwise indicated, conventional methods of chemistry, biochemistry, and recombinant DNA techniques are employed which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989).

In the following, some definitions of terms frequently used in this specification to characterize the invention are provided. These terms will, in each instance of its use, in the remainder of the specification have the respectively defined meaning and preferred meaning. Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. As used herein, the use of the term "comprising" also discloses the embodiment wherein no features other than the specifically mentioned features are present (i.e. "consisting of").

As used in this specification and the appended claims, the singular forms "a", "an", and "the" include plural referents, unless the content clearly dictates otherwise.

Throughout the instant application, the term "and/or" is a grammatical conjunction that is to be interpreted as encompassing that one or more of the cases it connects may occur. For example, the wording "the mutation is at position 239 and/or position 332" indicates that the mutation is at position 239, or at position 332, or at both, position 239 and position 332.

Unless otherwise stated, "GPRC5D" refers to human GPRC5D. A human GPRC5D polypeptide sequence is available under UniProt Accession No. Q9NZD1 (GPC5D_HUMAN) (last updated 2000 Oct. 1) or under NCBI Accession No. NP_061124.1, as shown below:

```
                                            (SEQ ID NO: 12)
MYKDCIESTG DYFLLCDAEG PWGIILESLA ILGIVVTILL

LLAFLELMRK IQDCSQWNVL PTQLLFLLSV LGLEGLAFAF

IIELNQQTAP VRYFLEGVLE ALCFSCLLAH ASNLVKLVRG

CVSESWTTIL CIAIGCSLLQ IIIATEYVTL IMTRGMMFVN

MTPCQLNVDE VVLIVYVLFL MALTFEVSKA TECGPCENWK

QHGRLIFITV LFSIIIWVVW ISMLLRGNPQ FQRQPQWDDP

VVCIALVTNA WVFLLLYIVP ELCILYRSCR QECPLQGNAC

PVTAYQHSFQ VENQELSRAR DSDGAEEDVA LTSYGTPIQP

QTVDPTQECF IPQAKLSPQQ DAGGV
```

The term "antigen-binding protein" as used herein refers to a polypeptide or a complex of two or more polypeptides comprising an antigen binding site that is able to specifically bind to an antigen. As used in the context of the present specification, the term antigen-binding protein includes antigen-binding proteins of multiple different formats as described below, including soluble antigen-binding proteins, membrane bound antigen-binding proteins, monovalent, bivalent and multivalent antigen-binding proteins, monospecifc, bispecific and multispecific antigen-binding proteins, single chain antigen-binding proteins and antigen-binding proteins comprising two or more chains, fusion proteins and chimeric proteins. The term includes antigen-binding proteins having the overall structure of e.g. a T cell receptor (TCR), an antibody, a chimeric antigen receptor (CAR), or of a fusion protein comprising elements of an antibody, a CAR and/or a TCR. The term further includes antigen-binding proteins having the overall structure of e.g. B cell receptors (BCRs), single chain antibodies, and single chain TCRs. An antigen-binding protein according to the present invention comprises variable regions or domains comprising specific complementary determining regions (CDRs) for binding to the respective epitope. Variable regions can be, for example, antibody based heavy chain variable domains (VH) and light chain variable domains (LH), or TCR based alpha and beta, or gamma and delta variable domains ($V_\alpha$ and $V_\beta$, or $V_\gamma$ and $V_\delta$).

The term "antibody" (Ab) or "immunoglobulin" (Ig), as used herein, refers to a tetramer comprising two heavy chains (HC) (about 50-70 kDa) and two light chains (LC) (about 25 kDa) inter-connected by one or more disulfide bonds. Each heavy chain is comprised of a heavy chain variable domain (VH) and a heavy chain constant region (CH). Each light chain is composed of a light chain variable domain (VL) and a light chain constant region (CL). The VH and VL domains can be subdivided further into regions of hypervariability, termed "complementarity determining regions" (CDRs), interspersed with regions that are more conserved, termed "framework regions" (FRs). Each VH and VL is composed of three CDRs (HCDR herein designates a CDR from the heavy chain; and LCDR herein designates a CDR from the light chain) and four FRs, arranged from amino-terminus to carboxyl-terminus in the following order: FR1, CDR1, FR2, CDR2, FR3, CDR3, FR4. There are two types of light chains, lambda (δ) and kappa (κ). There are five main heavy chain classes (or isotypes) which determine the functional activity of an antibody molecule: IgM, IgD, IgG, IgA and IgE. The term "antibody" refers to antibodies and fragments thereof, as well as single domain antibodies and fragments thereof and multispecific antibodies and fragments thereof, in particular a variable heavy chain of a single domain antibody, chimeric, humanized, bispecific or multispecific antibodies. Fragments or antigen-binding portions of antibodies comprise a portion of an intact antibody, in particular the antigen binding site or variable region of the antibody. Non-limiting examples of antibody fragments include Fv, Fab, F(ab')$_2$, Fab', dsFv, (dsFv)$_2$, scFv, sc(Fv)$_2$, diabodies, bispecific and multispecific antibodies formed from antibody fragments. A fragment of an antibody may also be a single domain antibody, such as a heavy chain variable region (VH). Preferably, "fragments of an antibody" comprise a portion of an intact antibody, in particular fragments of an antibody comprise the antigen binding site comprising at least the variable domain(s). Fragments of antigen-binding proteins or of antibodies exert essentially the same function compared to the antigen-binding protein or antibody from which they are derived meaning that fragments of antigen-binding proteins or of antibodies specifically bind to the same target as the antigen-binding protein or antibody from which they are derived.

The term "T cell receptor" (TCR) refers in the context of this invention to a heterodimeric cell surface protein of the immunoglobulin super-family, which is associated with invariant proteins of the CD3 complex involved in mediating signal transduction. TCRs exist in αγ and γδ forms, which are structurally similar but have quite distinct anatomical locations. The extracellular portion of native heterodimeric αβ TCR and γδ TCR each contain two polypeptides, each of which has a membrane-proximal constant domain, and a membrane-distal variable domain. Each of the constant and variable domains includes an intra-chain disulfide bond. The variable domains contain the highly polymorphic loops analogous to the complementarity determining regions (CDRs) of antibodies. Native alpha-beta heterodimeric TCRs have an alpha chain and a beta chain. Each alpha chain comprises variable, joining and constant regions, and the beta chain also usually contains a short diversity region between the variable and joining regions, but this diversity region is often considered as part of the joining region. The constant, or C, regions of TCR alpha and beta chains are referred to as TRAC and TRBC respectively (Lefranc, (2001), Curr Protoc Immunol Appendix 1: Appendix 10). Each variable region, comprises three "complementarity determining regions" (CDRs) embedded in a framework sequence of a framework region.

The assignment of amino acid numbers, and of FR and CDR regions, in the heavy or light chain or in the TCR variable domains may be in accordance with IMGT® definitions (Lefranc et al., *Dev Comp Immunol*. (2003) 27(1): 55-77); or the definitions of Kabat, *Sequences of Proteins of Immunological Interest* (National Institutes of Health, Bethesda, MD (1987 and 1991)); Chothia & Lesk, *J Mol Biol*. (1987) 196:901-17; Chothia et al., *Nature* (1989) 342:878-83; MacCallum et al., *J Mol Biol*. (1996) 262:732-45; Honegger and Plückthun, *J Mol Biol*. (2001) 309(3): 657-70; or Abhinandan and Martin, *Mol. Immunol*. (2008), 45(14):3832-9.

The term "complementary determining region" (CDR) as used herein refers to the non-contiguous antigen combining sites found within the variable domains of immunoglobulins, e.g. in VH, VL, Vα and Vβ. The definitions in the literature cited above include overlapping or subsets of amino acid residues when compared against each other. Nevertheless, application of either definition to refer to a CDR of an antibody or grafted antibodies or variants or fragments thereof, is intended to be within the scope of the term as defined and used herein. The amino acid residues, which encompass the CDRs, as defined by each of the above cited references are exemplarily set forth in below table as a comparison.

|       | Kabat[1] | Chothia[2] | AbM[3]  | Contact[4] |
|-------|----------|------------|---------|------------|
| HCDR1 | 31-35    | 26-32      | 26-35   | 30-35      |
| HCDR2 | 50-65    | 52-56      | 50-58   | 47-58      |
| HCDR3 | 95-102   | 95-102     | 95-102  | 93-101     |
| LCDR1 | 24-34    | 24-34      | 24-34   | 31-36      |
| LCDR2 | 50-56    | 50-56      | 50-56   | 46-55      |
| LCDR3 | 89-97    | 89-97      | 89-97   | 89-96      |

[1]Residue numbering follows the nomenclature of Kabat et al., supra
[2]Residue numbering follows the nomenclature of Chothia et al., supra
[3]Residue numbering according to AbM, Abhinandan and Martin, supra;
[4]Residue according to Contact Numbering, MacCallum et al., supra.

The terms "HCDR1", "HCDR2", and "HCDR3" refer to the first, second, and third CDR in a heavy chain variable domain of an antigen-binding polypeptide, for example an antibody or functional fragment thereof. As used herein, the terms "LCDR1", "LCDR2", and "LCDR3" refer, respectively, to the first, second, and third CDR in a light chain variable domain of an antigen-binding polypeptide, for example an antibody or a fragment thereof. As used herein, the terms "CDR1", "CDR2", and "CDR3" refer, respectively, to the first, second and third CDRs of a polypeptide chain's variable region of an antigen-binding polypeptide such as an antibody or an antigen-binding portion thereof, or of either variable domain of a TCR.

The term "chimeric antigen receptor" (CAR; also known as chimeric immunoreceptor, chimeric T cell receptor, artificial T cell receptor) as used herein refers to engineered receptors, which graft an arbitrary specificity onto an immune effector cell, preferably a T cell. Cells are genetically equipped with a CAR, which is a composite membrane receptor molecule and provides both targeting specificity and T cell activation. The most common form of CARs are fusions of a single chain variable fragment (scFv) derived from monoclonal antibodies, fused to a CD3 transmembrane- and endodomain. The CAR targets the T cell to a desired cellular target through an antibody-derived binding domain in the extracellular moiety, and T cell activation occurs via the intracellular moiety signaling domains when the target is encountered. The transfer of the coding sequence of these receptors into suitable cells, in particular T cells, is commonly facilitated by retro- or lentiviral vectors.

The term "recombinant antibody" refers to a non-naturally occurring antibody that is expressed from a cell or cell line comprising the nucleotide sequence(s) that encode the antibody, wherein said nucleotide sequence(s) are not naturally associated with the cell.

The term "isolated protein", "isolated polypeptide" or "isolated antibody" refers to a protein, polypeptide or antibody that by virtue of its origin or source of derivation (1) is not associated with naturally associated components that accompany it in its native state, (2) is free of other proteins from the same species, (3) is expressed by a cell from a different species, and/or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "affinity" refers to a measure of the attraction between an antigen and an antibody. The intrinsic attractiveness of the antibody for the antigen is typically expressed as the binding affinity equilibrium constant ($K_D$) of a particular antibody-antigen interaction. An antibody is said to specifically bind to an antigen when the $K_D$ for the binding is ≤1 µM, e.g., ≤100 nM or ≤10 nM. A $K_D$ binding affinity constant can be measured, e.g., by surface plasmon resonance (SPR) (Biacore™) using the Biacore™ T200 system, the IBIS MX96 SPR system from IBIS Technologies, or the Carterra LSA SPR platform, or by bio-layer interferometry, for example using the Octet™ system from ForteBio. A preferred method for determining the $K_D$ is by SPR using a Biacore™ T200 instrument, preferably as described in more detail in Example 2 below. An alternative preferred method for determining binding of an antigen-binding protein is by flow cytometry binding assays, preferably as described in more detail in Example 3 below.

The term "epitope" as used herein refers to a portion (determinant) of an antigen that specifically binds to an antigen-binding protein such as an antibody or a related molecule such as a bispecific binding molecule. Epitopic determinants generally consist of chemically active surface groupings of molecules such as amino acids or carbohydrate or sugar side chains and generally have specific three-dimensional structural characteristics, as well as specific charge characteristics. An epitope may be "linear" or "conformational". In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope on an antigen is determined, it is possible to generate antibodies to that epitope using techniques well known in the art. For example, an antibody to a linear epitope may be generated, e.g., by immunizing an animal with a peptide having the amino acid residues of the linear epitope. An antibody to a conformational epitope may be generated, e.g., by immunizing an animal with a mini-domain containing the relevant amino acid residues of the conformational epitope. An antibody to a particular epitope can also be generated, e.g., by immunizing an animal with the target molecule of interest (e.g., GPRC5D) or a relevant portion thereof, then screening for binding to the epitope. An antibody to a particular epitope also may be generated using phage display methods.

As used herein, the term "specifically binds" indicates that the antigen-binding protein, in particular antibody or antigen-binding fragment thereof binds to an epitope via its antigen-binding domain and that the binding entails some complementarity between the antigen binding domain and the epitope. Accordingly, an antigen-binding protein, in particular antibody that "specifically binds" to human GPRC5D (SEQ ID NO:12) may also bind to GPRC5D from other species (e.g., cynomolgus monkey, mouse, and/or rat GPRC5D) and/or GPRC5D proteins produced from other human alleles, but the extent of binding to an un-related, non-GPRC5D protein is less than about 10%, preferably less than 1%, more preferably less than 0.1% of the binding of the antigen-binding protein, in particular antibody to GPRC5D as measured, e.g., by a radioimmunoassay (RIA).

One can determine whether an antigen-binding protein, in particular an antibody binds to the same epitope as or competes for binding with an antigen-binding protein such as an anti-GPRC5D antibody of the present disclosure by using methods known in the art, including, without limitation, competition assays, epitope binning, and alanine scanning. In some embodiments, one allows the antigen-binding protein such as an anti-GPRC5D antibody of the present disclosure to bind to GPRC5D under saturating conditions, and then measures the ability of a test antigen-binding protein such as an antibody to bind to GPRC5D. If the test antibody is able to bind to GPRC5D at the same time as the reference anti-GPRC5D antibody, then the test antibody binds to a different epitope than the reference anti-GPRC5D antibody. However, if the test antibody is not able to bind to GPRC5D at the same time, then the test antibody binds to the same epitope, an overlapping epitope, or an epitope that is in close proximity to the epitope bound by the anti-GPRC5D antibody of the present disclosure. This experiment can be performed using, e.g., ELISA, RIA, Biacore™, SPR, Bio-Layer Interferometry or flow cytometry. To test whether an anti-GPRC5D antibody cross-competes with another anti-GPRC5D antibody, one may use the competition method described above in two directions, i.e., determining if the known antibody blocks the test antibody and vice versa. Such cross-competition experiments may be performed, e.g., using a Biacore™ T200, IBIS MX96, or Carterra LSA SPR instrument or the Octet™ system.

The term "antigen-binding portion" or "antigen-binding fragment" of an antibody, as used herein, refers to one or more portions or fragments of an antibody that retain the ability to specifically bind to an antigen (e.g., human GPRC5D preferably of SEQ ID NO: 12, or a portion thereof). It has been shown that certain fragments of a full-length antibody can perform the antigen-binding function of the antibody. Examples of binding fragments encompassed within the term "antigen-binding portion" thus include but are not limited to (i) a Fab fragment: a monovalent fragment consisting of the VL, VH, CL and CH1 domains; (ii) a F(ab')$_2$ fragment: a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which consists of a VH domain; and (vi) an isolated complementarity determining region (CDR) capable of specifically binding to an antigen. Furthermore, although the two domains of the Fv fragment, VL and VH, are encoded by separate genes, they can be joined, using recombinant methods, by a synthetic linker that enables them to be made as a single protein chain in which the VL and VH domains pair to form monovalent molecules (e.g. known as single chain Fv (scFv)). Also within the present disclosure are antigen-binding molecules comprising a VH and/or a VL. In the case of a VH, the molecule may also comprise one or more of a CH1, hinge, CH2, or CH3 region. Such single chain antibodies are also intended to be encompassed within the term "antigen-binding portion" of an antibody. Other forms of single chain antibodies, such as diabodies, are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites.

Antibody portions, such as Fab and F(ab')$_2$ fragments, can be prepared from whole antibodies using conventional techniques, such as papain or pepsin digestion of whole antibodies. Moreover, antibodies, antibody portions and immunoadhesin molecules can be obtained using standard recombinant DNA techniques, e.g., as described herein.

The class (isotype) and subclass of anti-GPRC5D antibodies may be determined by any method known in the art. In general, the class and subclass of an antibody may be determined using antibodies that are specific for a particular class and subclass of antibody. Such antibodies are available commercially. The class and subclass can be determined by ELISA or Western blot as well as other techniques. Alternatively, the class and subclass may be determined by sequencing all or a portion of the constant regions of the heavy and/or light chains of the antibodies, comparing their amino acid sequences to the known amino acid sequences of various classes and subclasses of immunoglobulins, and determining the class and subclass of the antibodies.

The term "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA. According to the invention, a nucleic acid is preferably an isolated nucleic acid. According to the invention, the term "nucleic acid encoding" and similar expressions mean that a nucleic acid, if present in the appropriate environment, preferably within a cell, can be expressed to produce the protein or peptide encoded by said nucleic acid.

The terms "patient" and likewise "subject" as used herein refer to an individual, such as a human, a non-human primate (e.g. chimpanzees and other apes and monkey species); farm animals, such as birds, fish, cattle, sheep, pigs, goats and horses; domestic mammals, such as dogs and cats; laboratory animals including rodents, such as mice, rats and guinea pigs. The term does not denote a particular age or sex and thus encompass adults, elderlies, children, and newborns. According to a preferred embodiment, the patient or subject is a mammal, more preferably the patient or subject is a human.

In the following, the elements of the present invention will be described in more detail. These elements are listed with specific embodiments; however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

I. Anti-GPRC5D Antigen-binding Proteins, in particular Antibodies and Binding Proteins The present invention provides antigen-binding proteins, in particular antibodies directed against GPRC5D and antigen-binding portions thereof, as well as GPRC5D-binding proteins comprising said antibodies or antigen-binding portions. In certain embodiments, the antibodies may contain Fc region modifications to enhance ADCC, improve stability, and/or enhance binding affinity for Fc receptors expressed on NK cells (e.g., FcγRIIIa).

In certain embodiments the present invention provides antigen-binding proteins comprising a first variable domain comprising a CDR1 of SEQ ID NO: 1, CDR2 of SEQ ID NO: 2 and CDR3 of SEQ ID NO: 3, and a second variable domain comprising a CDR1 of SEQ ID NO: 4, CDR2 of SEQ ID NO: 5 and CDR3 of SEQ ID NO: 6. According to one embodiment, the antigen-binding protein comprises a first variable domain comprising SEQ ID NO: 7 or a sequence at least 90% identical thereto, and a second variable domain comprising SEQ ID NO: 8 or a sequence at least 90% identical thereto. According to a preferred embodiment, the antigen-binding protein specifically binds GPRC5D, preferably as set forth in SEQ ID NO: 12. The present invention thus provides antibodies and antigen-binding portions thereof specifically binding GPRC5D, as well as GPRC5D-binding proteins comprising said antibodies or antigen-binding portions.

In certain embodiments, the antigen-binding proteins, in particular antibodies may contain Fc region modifications to enhance ADCC, improve stability, and/or enhance binding affinity for Fcγ receptors expressed on NK cells (e.g., FcγRIIIa).

In some embodiments, the antigen-binding proteins, in particular antibody or antigen-binding portion competes or cross-competes for binding to human GPRC5D with, or binds to the same epitope of human GPRC5D as, an antibody comprising a VH that comprises the amino acid sequence of SEQ ID NO: 7 and a VL that comprises the amino acid sequence of SEQ ID NO: 8.

In some embodiments, the antibody or antigen-binding portion has a heavy chain CDR3 (HCDR-3) amino acid sequence of SEQ ID NO: 3.

In some embodiments, the antibody or antigen-binding portion has heavy chain CDR1-3 (HCDR1-3) comprising the amino acid sequences of SEQ ID NOs: 1-3 respectively (i.e., has HCDR-1 comprising SEQ ID NO: 1, HCDR-2 comprising SEQ ID NO: 2, and HCDR-3 comprising SEQ ID NO: 3).

In some embodiments, the antigen-binding protein comprises a heavy chain variable domain (VH) amino acid sequence that is at least 80%, 85%, 90%, 91%, 92%, 93%, 94%, 95%, 96%, 97%, 98%, or 99% identical to the amino acid sequence of SEQ ID NO: 7. In some of these embodiments the HCDR1 to HCDR3 have the amino acid sequences according to SEQ ID NO: 1 to 3, respectively, i.e. the sequence variations are outside the HCDR1 to HCDR3.

In some embodiments, the antigen-binding protein, in particular antibody or antigen-binding portion has a VH comprising the amino acid sequence of SEQ ID NO: 7.

In some embodiments, the antigen-binding protein, in particular antibody has an HC amino acid sequence that is at least 80%, 85%, 90%, 91%, 92%, 93%, 94%, 95%, 96%, 97%, 98%, or 99% identical to the amino acid sequence of SEQ ID NO: 9 or 10. In some of these embodiments the HCDR1 to HCDR3 have the amino acid sequences according to SEQ ID NO: 1 to 3, respectively, i.e. the sequence variations are outside the HCDR1 to HCDR3.

In some embodiments, the antibody comprises a HC amino acid sequence of SEQ ID NO: 9 or 10.

In some embodiments, the antibody or antigen-binding portion has a light chain CDR3 (LCDR-3) amino acid sequence of SEQ ID NO: 6.

In some embodiments, the antibody or antigen-binding portion has light chain CDR1-3 (LCDR1-3) comprising the amino acid sequences of SEQ ID NOs: 4-6, respectively (i.e., has LCDR-1 comprising SEQ ID NO: 4, LCDR-2 comprising SEQ ID NO: 5, and LCDR-3 comprising SEQ ID NO: 6).

In some embodiments, the antigen-binding protein, in particular antibody or antigen-binding portion has a light chain variable domain (VL) amino acid sequence that is at least 80%, 85%, 90%, 91%, 92%, 93%, 94%, 95%, 96%, 97%, 98%, or 99% identical to the amino acid sequence of SEQ ID NO: 8. In some of these embodiments the LCDR1 to LCDR3 have the amino acid sequences according to SEQ ID NO: 4 to 6, respectively, i.e. the sequence variations are outside the LCDR1 to LCDR3.

In some embodiments, the antigen-binding protein, in particular antibody or antigen-binding portion has a VL comprising the amino acid sequence of SEQ ID NO: 8.

In some embodiments, the antigen-binding protein, in particular antibody has an LC amino acid sequence that is at least 80%, 85%, 90%, 91%, 92%, 93%, 94%, 95%, 96%, 97%, 98%, or 99% identical to the amino acid sequence of SEQ ID NO: 11. In some of these embodiments the LCDR1 to LCDR3 have the amino acid sequences according to SEQ ID NO: 4 to 6, respectively, i.e. the sequence variations are outside the LCDR1 to LCDR3.

In some embodiments, the antigen-binding protein has an LC amino acid sequence of SEQ ID NO: 11.

In certain embodiments, the antigen-binding protein comprises any one of the above-described heavy chains and any one of the above-described light chains.

In some embodiments, the antibody or antigen-binding portion of the present disclosure comprises the HCDR1-3 and LCDR1-3 amino acid sequences of SEQ ID NOs: 1-6, respectively. In other words, the antibody or antigen-binding portion comprises
the HCDR-1 amino acid sequence of SEQ ID NO: 1;
the HCDR-2 amino acid sequence of SEQ ID NO: 2;
the HCDR-3 amino acid sequence of SEQ ID NO: 3;
the LCDR-1 amino acid sequence of SEQ ID NO: 4;
the LCDR-2 amino acid sequence of SEQ ID NO: 5; and
the LCDR-3 amino acid sequence of SEQ ID NO: 6.

In some embodiments, the antigen-binding protein, in particular antibody or antigen-binding portion of the present disclosure comprises a VH and a VL that are 80%, 85%, 90%, 91%, 92%, 93%, 94%, 95%, 96%, 97%, 98%, or 99% identical (e.g., 90% identical) to the amino acid sequences of SEQ ID NOs: 7 and 8, respectively. In some of these embodiments the HCDR1 to HCDR3 and LCDR1 to LCDR3 have the amino acid sequences according to SEQ ID NO: 1 to 6, respectively, i.e. the sequence variations are outside the HCDR1 to HCDR3 and LCDR1 to LCDR3.

The percent identity of two amino acid sequences (or of two nucleic acid sequences) may be obtained by, e.g., BLAST® using default parameters (available at the U.S. National Library of Medicine's National Center for Biotechnology Information website). In some embodiments, the length of a reference sequence aligned for comparison purposes is at least 60% (e.g., at least 70%, at least 80%, at least 90%, or 100%) of the reference sequence. For example, if a sequence is indicated to be at least 90% identical to a given SEQ ID NO such as SEQ ID NO: 7, said sequence is aligned with the sequence of SEQ ID NO: 7 preferably over the whole length of SEQ ID NO: 7, and the percent identity is calculated with respect to the whole length of SEQ ID NO: 7, which example is an alignment over 100% of the length of the reference sequence.

In some embodiments, the antigen-binding protein, in particular antibody or antigen-binding portion of the present disclosure comprises a VH and a VL that comprise the amino acid sequences of SEQ ID NOs: 7 and 8, respectively (i.e., comprises a VH that comprises the amino acid sequence of SEQ ID NO: 7 and a VL that comprises the amino acid sequence of SEQ ID NO: 8).

In some embodiments, the antigen-binding protein, in particular antibody of the present invention comprises
a) an HC comprising the amino acid sequence of SEQ ID NO: 9 or a sequence at least 80%, 85%, 90%, 91%, 92%, 93%, 94%, 95%, 96%, 97%, 98%, or 99% identical to SEQ ID NO: 9, and an LC comprising the amino acid sequence of SEQ ID NO: 11 or a sequence at least 80%, 85%, 90%, 91%, 92%, 93%, 94%, 95%, 96%, 97%, 98%, or 99% identical to SEQ ID NO: 11; or
b) an HC comprising the amino acid sequence of SEQ ID NO: 10 or a sequence at least 80%, 85%, 90%, 91%, 92%, 93%, 94%, 95%, 96%, 97%, 98%, or 99% identical to SEQ ID NO: 10, and an LC comprising the amino acid sequence of SEQ ID NO: 11 or a sequence at least 80%, 85%, 90%, 91%, 92%, 93%, 94%, 95%, 96%, 97%, 98%, or 99% identical to SEQ ID NO: 11.

According to more specific embodiments, the antigen-binding protein of the present invention, in particular antibody comprises:
a) an HC comprising the amino acid sequence of SEQ ID NO: 9 and an LC comprising the amino acid sequence of SEQ ID NO: 11; or
b) an HC comprising the amino acid sequence of SEQ ID NO: 10 and an LC comprising the amino acid sequence of SEQ ID NO: 11.

According to a particularly preferred embodiment of the present invention, the antigen-binding protein is an antibody or an antigen-binding fragment thereof.

The class of an antibody obtained by the methods described herein may be changed or switched with another class or subclass. In some embodiments of the present disclosure, a nucleic acid molecule encoding VL or VH is isolated using methods well known in the art such that it does not include nucleic acid sequences encoding CL or CH, respectively. The nucleic acid molecules encoding VL or VH then are operatively linked to a nucleic acid sequence encoding a CL or CH, respectively, from a different class of immunoglobulin molecule. This may be achieved using a vector or nucleic acid molecule that comprises a CL or CH sequence, as described above. For example, an antibody that was originally IgM may be class switched to IgG. Further, the class switching may be used to convert one IgG subclass to another, e.g., from $IgG_1$ to $IgG_2$. A κ light chain constant region can be changed, e.g., to a λ light chain constant region, or vice-versa. An exemplary method for producing an antibody of the present disclosure with a desired Ig isotype comprises the steps of isolating a nucleic acid molecule encoding the heavy chain of an antibody and a nucleic acid molecule encoding the light chain of an antibody, obtaining the variable domain of the heavy chain, ligating a coding sequence for the variable domain of the heavy chain with a coding sequence for the constant region of a heavy chain of the desired isotype, expressing the light chain and the heavy chain encoded by the ligated sequence in a cell, and collecting the antibody with the desired isotype.

The antibody of the present disclosure can be an IgG, an IgM, an IgE, an IgA, or an IgD molecule, but is typically of human IgG isotype, e.g., of human IgG subclass $IgG_1$, $IgG_{2a}$ or $IgG_{2b}$, $IgG_3$, or $IgG_4$. In preferred embodiments, the antibody is of human $IgG_1$ subclass.

In certain preferred embodiments, the antibody of the present disclosure is monospecific.

In some embodiments, the antigen-binding protein, in particular antibody may comprise at least one mutation in the Fc region. For example, in some embodiments, the antibody is of isotype subclass $IgG_1$ and comprises at least one mutation in the Fc region that enhances lysis of antibody-coated target cells by cells, such as natural killer (NK) cells (antibody-dependent cell-mediated cytotoxicity, or ADCC). In certain embodiments, the antigen-binding protein, in particular antibody may be, e.g., an NK cell engager. In certain embodiments, the mutation(s) are at one or more of positions 239 and 332 according to the Eu numbering scheme of the Fc region. The mutation at position 239 is preferably S239D. The mutation at position 332 is preferably I332E. In particular embodiments, the Fc region comprised in the antigen binding protein, in particular antibody comprises both, the S239D and the I332E mutation.

In some embodiments, the antibody may comprise at least one mutation in the Fc region to enhance stability (e.g., thermal stability). For example, the antibody may comprise at least one heavy chain comprising an engineered intrachain disulfide bond mediated by a pair of cysteines, e.g., substituting for an arginine (R) at amino acid position 292 (R292C) and a valine (V) at amino acid position 302 (V302C) according to the Eu numbering scheme. The cysteines may be substituted on one heavy chain or both heavy chains.

In certain embodiments, the antibody has mutations in the Fc domain to both 1) alter effector function, and 2) enhance stability. In some embodiments, the Fc domain may contain any mutation or combination of mutations described in PCT Patent Publication WO 2022/249146, which is incorporated herein by reference in its entirety. For example, the antibody heavy chain may comprise 1) mutations at positions 239 (e.g., S239D) and/or 332 (e.g., I332E), and 2) a pair of cysteine substitutions that forms an intrachain disulfide bond, e.g., R292C and V302C (Eu numbering scheme). The mutations of 1) may be on the same or a different heavy chain than the mutations of 2). In some embodiments, the mutations of 1) and 2) are on one heavy chain. In some embodiments, the mutations of 1) are on one heavy chain and the mutations of 2) are on a different heavy chain. In some embodiments, the mutations of 1) and 2) are on both heavy chains. A combination of the S239D/I332E/R292C/V302C quadruple mutation is also called "DE-DSB" mutations herein. In particular embodiments, the antibody has a heavy chain amino acid sequence of SEQ ID NO: 10.

In some embodiments, an antibody described herein with any Fc mutation or combination of Fc mutations described herein (e.g., the DE-DSB mutations) has enhanced binding to FcγRIIIa (CD16a; highly expressed on NK cells), enhanced in vivo stability (e.g., enhanced serum half-life and/or decreased clearance), enhanced NK cell engagement, or any combination thereof (e.g., all three), compared to the same antibody with a wildtype Fc domain. As used herein, the term "in vivo stability" refers to the ability of an antibody described herein to remain intact (e.g., limited degradation and/or unfolding) and functional (e.g., retained binding activity), and to retain a sufficiently high concentration in serum to elicit a measurable activity (e.g., target tumor cell killing).

In some embodiments, the antigen-binding protein, in particular antibody may be afucosylated. In certain embodiments, the afucosylated antigen-binding protein, in particular antibody has enhanced ADCC compared to the same antibody without afucosylation. An antigen-binding protein, in particular antibody as described herein may be prepared with an afucosylated Fc domain according to any method known in the art. For example, the antigen-binding protein, in particular antibody may be generated according to a method disclosed in Pereira et al., MAbs (2018) 10(5):693-711. In some embodiments, an antigen-binding protein, in particular antibody with an afucosylated Fc domain may be generated using cell engineering, e.g., by knockdown of the FUT8 gene, which codes for an enzyme responsible for the core fucosylation of IgG Fc (Yamane-Ohnuki et al., *Biotechnol Bioeng.* (2004) 87:614-22). In some embodiments, an antigen-binding protein, in particular antibody with an afucosylated Fc domain may be generated using a heterologous enzyme that redirects fucose synthesis to deplete the fucose pool inside the cell (GlymaxX® technology, ProBioGen). In some embodiments, an antigen-binding protein, in particular antibody with an afucosylated Fc domain may be generated by adding to the cell culture one or more fucosylation inhibitor molecules such as kifunensine (Krahn et al., *PHASCI* (2017) 96:428-39). In certain embodiments, the antigen-binding protein, in particular antibody is afucosylated using GlymaxX® technology (ProBioGen).

In any of the embodiments described herein, the antigen-binding protein, in particular antibody may have any Fc mutations described herein to 1) alter effector function, and/or 2) enhance stability (e.g., DE-DSB mutations), and additionally may be afucosylated. According to a further embodiment, an antigen-binding protein, in particular antibody having an FC region comprising the Fc mutations described herein, such as the DE-DSB mutations, does not comprise an afucosylated Fc region.

In some embodiments, an antigen-binding protein, in particular antibody described herein, or a binding protein comprising said antibody or an antigen-binding portion thereof, has at least one (e.g., 1, 2, 3, 4, 5, 6, 7, 8, 9, 10, 11, 12, 13, 14, 15, 16, 17, 18, 19, 20, or all 21) of the following properties:

a) binds, preferably specifically to cells that express human GPRC5D;
b) binds, preferably specifically to cells that express cynomolgus GPRC5D;
c) binds, preferably specifically to cells that express human FcγRIIIa;
d) binds, preferably specifically to cells that express cynomolgus FcγRIIIa;
e) binds, preferably specifically to human GPRC5D as set forth in SEQ ID NO: 12 having an N-terminal deletion of up to 20 amino acids, such as an N-terminal deletion of 1, 2, 3, 4, 5, 6, 7, 8, 9, 10, 11, 12, 13, 14, 15, 16, 17, 18, 19 or 20 amino acids;
f) binds, preferably specifically to SEQ ID NO: 15;
g) binds, preferably specifically to SEQ ID NO: 16;
h) binds, preferably specifically to SEQ ID NO: 17;
i) promotes NK cell engagement;
j) promotes NK cell degranulation;
k) induces NK cell activation;
l) induces primary plasma cell depletion;
m) promotes lysis of cancer cells (e.g., multiple myeloma cancer cells) in the presence of NK cells;

n) induces low or no release of cytokines (such as IFN-γ, IL-6, and/or TNF-α) by peripheral blood mononuclear cells (PBMCs) in the presence of GPRC5D-expressing cells (e.g., multiple myeloma cells); for example, with an increase in cytokines of no more than 1-fold, 2-fold, 3-fold, 4-fold, or 5-fold;

o) is quantifiable in plasma for at least 28 days in vivo (e.g., when administered to cynomolgus monkeys at a single IV or SC dose of, for example, 25 mg/kg);

p) has a terminal elimination half-life of at least nine days in vivo (e.g., when administered to cynomolgus monkeys at a single IV dose of, for example, 25 mg/kg);

q) does not result in elevation of IFN-γ, TL-8, and TNFα levels in vivo (e.g., when administered to cynomolgus monkeys at a single IV or SC dose of, for example, 25 mg/kg);

r) inhibits tumor growth in vivo (e.g., for multiple myeloma tumors);

s) binds, preferably specifically to a GPRC5D dimer;

t) shows cross-reactivity in mice; and u) shows cross-reactivity in cynomolgus monkeys.

Where an antibody comprises Fc mutations and/or glycosylation patterns that enhance the Fc domain's binding affinity for FcγRIIIa on NK cells, the antibody is also termed herein an NK cell engager. In some preferred embodiments, the NK cell engager herein is an anti-GPRC5D IgG$_1$ with the DE-DSB mutations described herein. In other preferred embodiments, the NK cell engager herein is an anti-GPRC5D IgG$_1$ with an afucosylated Fc domain. In further preferred embodiments, the NK cell engager herein is an anti-GPRC5D IgG$_1$ with the DE-DSB mutations and/or with an afucosylated Fc domain. A particularly preferred antigen-binding protein of the invention is thus an antibody comprising 1) an HC comprising the amino acid sequence of SEQ ID NO: 9 and an LC comprising the amino acid sequence of SEQ ID NO: 11, or 2) an HC comprising the amino acid sequence of SEQ ID NO: 10 (DE-DSB mutations) and an LC comprising the amino acid sequence of SEQ ID NO: 11. According to a particularly preferred embodiment, the Fc domain of the antibody of 1) is afucosylated.

In some embodiments, an anti-GPRC5D antigen-binding protein, in particular antibody or antigen-binding portion thereof described herein, or a binding protein comprising said antibody or antigen-binding portion, may inhibit tumor growth and/or induce tumor growth regression in vivo. In some embodiments, an anti-GPRC5D antigen-binding protein, in particular antibody or antigen-binding portion thereof or a binding protein described herein may slow down or reverse metastasis in a cancer patient. In some embodiments, an anti-GPC5D antigen-binding protein, in particular antibody or antigen-binding portion thereof or a binding protein described herein may decrease or eliminate cancer relapse in a cancer patient. In some embodiments, an anti-GPRC5D antigen-binding protein, in particular antibody or antigen-binding portion thereof or a binding protein described herein may prolong survival of a cancer patient. In certain embodiments, the cancer patient has multiple myeloma. Any combination of the above properties is also contemplated.

A binding protein of the present disclosure may be an anti-GPRC5D antibody or antigen-binding portion thereof described herein, or may comprise the anti-GPRC5D antibody or antigen-binding portion derivatized or linked to another molecule (e.g., another peptide or protein). In general, the antibodies or antigen-binding portions thereof are derivatized or linked such that GPRC5D binding is not affected adversely by the derivatization or linking. Accordingly, the binding proteins of the present disclosure are intended to include both intact and modified forms of the anti-GPRC5D antibodies or antigen-binding portions described herein. For example, the antibody or antibody portion of the present disclosure can be functionally linked (by chemical coupling, genetic fusion, noncovalent association or otherwise) to one or more other molecular entities, such as another antibody (e.g., a bispecific antibody), a label (e.g., a radioactively or fluorescently detectable marker), or a therapeutic agent (e.g., a cytotoxin or therapeutically useful radio-isotope).

In some embodiments, the binding protein is a fusion protein, wherein the anti-GPRC5D antibody or antigen-binding portion thereof is linked to another polypeptide (e.g., an Fc polypeptide that dimerizes to form an Fc domain). In certain embodiments, only the variable domains of the anti-GPRC5D antibody are linked to the polypeptide. In certain embodiments, the VH domain of an anti-GPRC5D antibody is linked to a first polypeptide, while the VL domain of an anti-GPRC5D antibody is linked to a second polypeptide that associates with the first polypeptide in a manner such that the VH and VL domains can interact with each other to form an antigen-binding site. In some embodiments, the VH domain is separated from the VL domain by a linker such that the VH and VL domains can still interact with each other (e.g., single-chain antibodies). The VH-linker-VL antibody (e.g., an scFv) is then linked to the polypeptide of interest (e.g., an Fc polypeptide). In an scFv, the VH can be N-terminal or C-terminal to the VL, and the linker between them can be a flexible linker such as a Gly/Ser-rich linker. For example, the linker may contain one or more (e.g., 2, 3, 4, or 5) GGGGS (SEQ ID NO: 13) motifs.

In some embodiments, the binding protein is a bispecific binding molecule. In certain embodiments, the bispecific binding molecule additionally has the binding specificity of another, distinct anti-GPRC5D antibody or an antibody that targets a different protein, such as a cancer antigen, another cell surface molecule whose activity mediates a disease condition such as cancer, or a cell surface molecule on an immune cell (e.g., a NK cell or a T cell). In some embodiments, the bispecific binding molecule binds GPRC5D and CD3. In some embodiments, the binding protein is a bispecific T cell engager.

In some embodiments, the binding protein is a chimeric antigen receptor (CAR). Such a CAR may be used in CAR-T therapy, in which T cells are engineered to express the CAR targeting GPRC5D.

In some embodiments, the binding protein is a fusion antibody or an immunoadhesin.

The antigen-binding protein of the invention can be, for example, a single chain antigen-binding protein, double chain antigen-binding protein, or an antigen-binding protein comprising more than two polypeptide chains.

The present invention specifically provides an anti-GPRC5D IgG$_1$ comprising an HC comprising the amino acid sequence of SEQ ID NO: 10 (DE-DSB mutations) and an LC comprising the amino acid sequence of SEQ ID NO: 11. The present invention further specifically provides an anti-GPRC5D IgG$_1$ comprising the amino acid sequence of SEQ ID NO: 9 and an LC comprising the amino acid sequence of SEQ ID NO: 11, wherein the Fc domain is afucosylated.

The antigen-binding protein of the present invention preferably shows cross-reactivity in mice and/or in monkeys, in particular in cynomolgus monkey. According to a particularly preferred embodiment, the antigen-binding protein exhibits this cross-reactivity if in an antibody format or in an antibody fragment format such as the anti-GPRC5D IgG$_1$ described herein. This cross-reactivity can be particularly advantageous in assays and pre-clinical testing, such as in vitro and in vivo testing, e.g. in or with samples of respective animals.

The antigen-binding protein as described herein is particularly suitable for use as a medicament. According to a preferred embodiment, the medicament is for use in treating cancer, preferably multiple myeloma, non-Hodgkin's lymphoma, renal cancer, breast cancer, ovarian cancer, or pancreatic cancer. According to a particularly preferred embodiment, the cancer is multiple myeloma. For example, the cancer may be smoldering (asymptomatic) multiple myeloma or active (symptomatic) multiple myeloma. The multiple myeloma may be hyperdiploid (HMM) or non-hyperdiploid or hypodiploid. The myeloma subtype may be, e.g., IgG, IgA, IgM, IgE, or IgD myeloma. Further preferred forms of myeloma include light chain myeloma, non-secretory myeloma, solitary plasmacytoma, multiple solitary plasmacytoma, extramedullary myeloma, and monoclonal gammopathy of undetermined significance (MGUS). According to a particularly preferred embodiment, the cancer is a GPRC5D-positive cancer.

II. Making of Antibodies and Binding Proteins

The antigen-binding protein of the present invention, in particular the antibodies and antigen-binding portions thereof, or binding proteins comprising said antibodies or antigen-binding portions, may be produced recombinantly using isolated nucleic acid molecules such as expression constructs. Respective variable polypeptide chains such as heavy and light chains may be encoded by nucleotide sequences on the same or different isolated nucleic acid molecules. Biomolecules (e.g., nucleic acid or polypeptide) molecules referred to herein as "isolated" or "purified" are those that (1) have been separated away from the biomolecules (e.g., nucleic acids of the genomic DNA or cellular RNA, or polypeptides, of their source of origin; and/or (2) do not occur in nature. The encoding sequences for each polypeptide chain may be cloned into a single vector or cloned into separate vectors. The present invention therefore also provides one or more nucleic acid molecules encoding the antigen-binding protein of the present invention. According to one embodiment, the nucleic acid molecule(s) encoding the antigen-binding protein of the invention is DNA or RNA, preferably mRNA. The nucleic acid molecule(s) of the invention encode one or more polypeptide chains of the antigen-binding protein. A nucleic acid encoding more than one of the peptide chains can be a polycistronic nucleic acid. A respective RNA is preferably obtained by in-vitro transcription.

Nucleic acids such as RNA encoding the antigen-binding protein according to the invention may be introduced into T cells or other cells with lytic potential, in particular into lymphoid cells. The invention thus also involves introduction, i.e. transfection, of one or more nucleic acid molecules encoding the antigen-binding protein of the present invention into cells such as T cells in vitro or in vivo. According to the invention, it is preferred to administer the nucleic acid molecule(s) encoding the antigen-binding protein in naked form or in a carrier. Respective carriers such as lipid carriers contemplated for use in the present invention include any substances or vehicles with which nucleic acid molecules such as RNA can be associated, e.g. by forming complexes with the nucleic acid or forming vesicles in which the nucleic acid is enclosed or encapsulated. This advantageously results in increased stability of the nucleic acid compared to naked nucleic acids. In particular, stability of the nucleic acid in blood may be increased. For example, nanoparticulate RNA formulations with defined particle size, such as lipoplexes from RNA and liposomes, e.g. lipoplexes comprising DOTMA and DOPE or DOTMA and Cholesterol, can be used.

Nucleic acid molecules may, according to the invention, be present alone or in combination with other nucleic acids, which may be homologous or heterologous. In preferred embodiments, a nucleic acid is functionally linked to one or more expression control sequences which may be homologous or heterologous with respect to said nucleic acid. The term "homologous" means that the nucleic acids are also functionally linked naturally, and the term "heterologous" means that the nucleic acids are not functionally linked naturally. A nucleic acid and an expression control sequence are "functionally" linked to one another, if they are covalently linked to one another in such a way that expression or transcription of said nucleic acid is under the control or under the influence of said expression control sequence. The antigen-binding protein of the present invention, in particular the antibodies or antigen-binding portions thereof or binding proteins may be produced in, e.g., mammalian host cells, using appropriate expression constructs. Suitable host cells in accordance with the present invention can be identified by the skilled person. Mammalian cell lines available as hosts for expression include many immortalized cell lines available from the American Type Culture Collection (ATCC). These include, inter alia, Chinese hamster ovary (CHO) cells, NS0 cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Other cell lines that may be used are insect cell lines, such as Sf9 or Sf21 cells, and yeast cell lines. Cell lines may be selected based on their expression levels. The antigen-binding proteins may be isolated and purified from the host cell culture using well known methods, such as centrifugation, ultracentrifugation, protein A, protein G, protein A/G, or protein L purification, and/or ion exchange chromatography.

Host cells used to produce the antigen-binding proteins, in particular the antibodies, antigen-binding portions, or binding proteins are also termed "recombinant host cells". A "recombinant host cell" (or simply "host cell"), as used herein, means a cell into which a recombinant expression construct has been introduced. By definition, a recombinant host cell does not occur in nature. A protein produced from the expression construct is a recombinant protein.

The present invention also provides an immune effector cell comprising the antigen-binding protein, the nucleic acid molecule(s), or the vector(s) according to the present invention. Immune effector cells used in connection with the present invention are preferably selected from the group consisting of a T cell, a Natural Killer (NK) cell, lymphokine-activated killer (LAK) cells, and a cytotoxic T lymphocyte (CTL). Upon activation/stimulation, each of these cytotoxic lymphocytes triggers the destruction of target cells. According to one embodiment, the immune effector cell is a human immune effector cell.

III. Pharmaceutical Compositions and Use

Another aspect of the present disclosure is a pharmaceutical composition comprising as an active ingredient (or as the sole active ingredient) the antigen-binding protein, in particular the antibody or antigen-binding portion thereof or the binding protein of the present invention, the isolated nucleic acid molecule(s), the vector(s), or the host cell(s) of the present invention. The pharmaceutical composition may additionally comprise one or more pharmaceutically acceptable excipients. A "pharmaceutically acceptable excipient" may include appropriate solvents, dispersion media, antibacterial and antifungal agents, isotonic agents, and the like. Examples of pharmaceutically acceptable excipients are water and saline (e.g., phosphate-buffered saline).

The pharmaceutical compositions herein may be used in the treatment of cancer, e.g., GPRC5D-positive cancer. In some embodiments, the cancer may be selected from, for example, multiple myeloma, non-Hodgkin's lymphoma, renal cancer, breast cancer, ovarian cancer, and pancreatic cancer. In particular embodiments, the cancer is multiple myeloma. For example, the cancer may be smoldering (asymptomatic) multiple myeloma or active (symptomatic) multiple myeloma. The multiple myeloma may be hyperdiploid (HMM) or non-hyperdiploid or hypodiploid. The myeloma subtype may be, e.g., IgG, IgA, IgM, IgE, or IgD myeloma. In some embodiments, the antibodies or antigen-binding portions thereof or binding proteins of the present disclosure are used for treatment of light chain myeloma, non-secretory myeloma, solitary plasmacytoma, multiple solitary plasmacytoma, extramedullary myeloma, and monoclonal gammopathy of undetermined significance (MGUS).

A "therapeutically effective amount" is an amount of the binding protein (e.g., anti-GPRC5D antibody or antigen-binding portion thereof) or a pharmaceutical composition comprising it that will relieve to some extent one or more of the symptoms of the disease being treated. A therapeutically effective amount of an anti-cancer therapeutic may, for example, result in delayed tumor growth, elimination of cancer cells, tumor shrinkage, increased survival, slowed or decreased metastasis, or other clinical endpoints desired by healthcare professionals.

In some embodiments, the antibody or antigen-binding portion thereof or binding protein may be co-administered or formulated with another medication/drug for the treatment of cancer. The additional therapeutic treatment may comprise, e.g., an immunostimulatory agent, a vaccine, a chemotherapeutic agent, an anti-neoplastic agent, an anti-angiogenic agent, a corticosteroid, and/or radiation therapy. In some embodiments, the additional therapeutic treatment may comprise a different anti-cancer antibody.

The pharmaceutical compositions herein may be delivered to the patient through parenteral administration, e.g., intravenous infusion.

IV. Diagnostic Use

The antigen-binding proteins, in particular antibodies and antigen-binding portions or binding proteins of the present disclosure also are useful in diagnostic processes (e.g., in vitro or ex vivo). For example, the antigen-binding proteins, antibodies or antigen-binding portions thereof, or binding proteins can be used to detect and/or measure the level of GPRC5D in a biological sample from a patient (e.g., a tumor biopsy, a tissue sample, or a blood sample). Suitable detection and measurement methods include immunological methods such as flow cytometry, enzyme-linked immunosorbent assays (ELISA), chemiluminescence assays, radioimmunoassays, and immunohistochemistry. The present disclosure further encompasses kits (e.g., diagnostic kits) comprising the antigen-binding proteins, antibodies, or antigen-binding portions thereof, or binding proteins, the nucleic acid molecule(s), or the host cell(s) described herein.

V. Treatments

The present invention further provides the antigen-binding protein, in particular antibodies or antigen-binding portions thereof, the isolated nucleic acid molecule(s), the vector(s), the host cell(s), or the pharmaceutical composition according to the invention for use in medicine or as a medicament, preferably for use in treating cancer.

Likewise, the present invention provides the use of the antigen-binding protein, the isolated nucleic acid molecule(s), the vector(s), the host cell(s), or the pharmaceutical composition according to the invention for the preparation of a medicament, preferably wherein the medicament is for treating cancer.

The present invention also provides a method of treating a disease, comprising administering to a subject a therapeutically effective amount of the antigen-binding protein, the isolated nucleic acid molecule(s), the vector(s), the host cell(s), or the pharmaceutical composition according to the invention. The disease is preferably cancer.

According to the present invention, the cancer is preferably selected from the group consisting of multiple myeloma, non-Hodgkin's lymphoma, renal cancer, breast cancer, ovarian cancer, or pancreatic cancer multiple myeloma may be hyperdiploid (HMM) or non-hyperdiploid or hypodiploid. The myeloma subtype may be, e.g., IgG, IgA, IgM, IgE, or IgD myeloma. Further preferred forms of myeloma include light chain myeloma, non-secretory myeloma, solitary plasmacytoma, multiple solitary plasmacytoma, extramedullary myeloma, and monoclonal gammopathy of undetermined significance (MGUS). According to a particularly preferred embodiment, the cancer is a GPRC5D-positive cancer.

The proteins and compositions described herein may be administered via any conventional route, such as by parenteral administration including by injection or infusion. Administration is preferably parenterally, e.g. intravenously, intraarterially, subcutaneously, intradermally or intramuscularly.

Compositions suitable for parenteral administration usually comprise a sterile aqueous or nonaqueous preparation of the active compound, which is preferably about isotonic to the blood of the recipient.

The proteins and compositions described herein are preferably administered in therapeutically effective amounts.

In further embodiments the present invention also relates to:

1. A binding protein comprising an antigen-binding portion of an antibody that comprises HCDR1-3 and LCDR1-3 amino acid sequences of SEQ ID NOs: 1-6, respectively.

2. The binding protein of item 1, wherein said antibody comprises a heavy chain variable domain (VH) amino acid sequence and a light chain variable domain (VL) amino acid sequence that are at least 90% identical to the amino acid sequences of SEQ ID NOs: 7 and 8, respectively.

3. The binding protein of item 2, wherein said antibody comprises a VH comprising SEQ ID NO: 7 and a VL comprising SEQ ID NO: 8.

4. The binding protein of any one of items 1-3, wherein the antibody is of human IgG isotype.

5. The binding protein of item 4, wherein the antibody is of human IgG1 isotype subclass.

6. The binding protein of any one of items 1-5, wherein said antibody comprises a heavy chain (HC) amino acid sequence and a light chain (LC) amino acid sequence that are at least 90% identical to the amino acid sequences of SEQ ID NOs: 9 and 11, respectively.

7. A binding protein comprising an antibody that comprises a heavy chain (HC) comprising SEQ ID NO: 9 and a light chain (LC) comprising SEQ ID NO: 11.

8. The binding protein of any one of items 1-6, wherein the antibody comprises at least one Fc domain mutation.

9. The binding protein of item 8, wherein the antibody comprises at least one Fc domain mutation that enhances binding of the antibody to human FcγRIIIa.

10. The binding protein of item 8, wherein the Fc domain mutation is at position 239, optionally S239D, or 332, optionally I332E, wherein the residues are numbered according to Eu numbering.

11. The binding protein of item 8, wherein the antibody comprises Fc domain mutations at positions 239 and 332, optionally S239D and I332E, wherein the residues are numbered according to Eu numbering.

12. The binding protein of any one of items 8-11, wherein the antibody comprises at least one Fc domain mutation that enhances antibody stability.

13. The binding protein of any one of items 1-11, wherein the antibody comprises a pair of Fc domain mutations to cysteines, optionally wherein the mutations occur at positions 292 and 302, optionally wherein the mutations are R292C and V302C, wherein the residues are numbered according to Eu numbering.

14. The binding protein of any one of items 8-13, wherein said antibody comprises a heavy chain (HC) amino acid sequence and a light chain (LC) amino acid sequence that are at least 90% identical to the amino acid sequences of SEQ ID NOs: 10 and 11, respectively.

15. A binding protein comprising an antibody that comprises a heavy chain comprising SEQ ID NO: 10 and a light chain comprising SEQ ID NO: 11.

16. The binding protein of any one of items 1-15, wherein said antibody is afucosylated.

17. The binding protein of any one of items 1-16, wherein said binding protein is a fusion protein.

18. The binding protein of any one of items 1-17, wherein said binding protein is a bispecific or multispecific binding molecule.

20. Isolated nucleic acid molecule(s) that encode the binding protein of any one of items 1-18.

21. Vector(s) comprising the isolated nucleic acid molecule(s) of item 20, wherein the vector(s) optionally comprise an expression control sequence.

22. A host cell comprising the isolated nucleic acid molecule(s) of item 20.

19. A pharmaceutical composition comprising the binding protein of any one of items 1-18 and a pharmaceutically acceptable excipient.

23. A method for producing a binding protein, comprising
providing a host cell according to item 22,
culturing said host cell under conditions suitable for expression of the binding protein, and
isolating the resulting binding protein from the culture.

24. A method for treating cancer in a human patient in need thereof, comprising administering to said patient a therapeutically effective amount of the binding protein of any one of items 1-18 or the pharmaceutical composition of item 19.

25. The method of item 24, wherein the cancer is multiple myeloma, non-Hodgkin's lymphoma, renal cancer, breast cancer, ovarian cancer, or pancreatic cancer.

26. The method of item 24, wherein the cancer is multiple myeloma.

27. The binding protein of any one of items 1-18 or the pharmaceutical composition of item 19, for use in treating a human in need thereof in a method of any one of items 24-26.

28. Use of the binding protein of any one of items 1-18 for the manufacture of a medicament for treating a human patient in need thereof in a method of any one of items 24-26.

29. An antigen-binding protein comprising two variable domains, the first variable domain comprising a HCDR1 of SEQ ID NO: 1, a HCDR2 of SEQ ID NO: 2 and a HCDR3 of SEQ ID NO: 3, and the second variable domain comprising a LCDR1 of SEQ ID NO: 4, a LCDR2 of SEQ ID NO: 5 and a LCDR3 of SEQ ID NO: 6.

30. The antigen-binding protein of item 29, comprising a heavy chain variable domain (VH) amino acid sequence at least 90% identical to the amino acid sequence of SEQ ID NO: 7, and a light chain variable domain (VL) amino acid sequence at least 90% identical to the amino acid sequence of SEQ ID NO: 8.

31. The antigen-binding protein of item 29 or 30, wherein the antigen-binding protein is an antibody, preferably of human IgG isotype, more preferably wherein the antibody is of human $IgG_1$ isotype subclass.

32. The antigen-binding protein of any one of items 29-31, comprising a heavy chain (HC) amino acid sequence and a light chain (LC) amino acid sequence that are at least 90% identical to the amino acid sequences of SEQ ID NOs: 9 and 11, respectively.

33. The antigen-binding protein of any one of items 29-32, wherein the antigen-binding protein is an antibody comprising at least one Fc domain mutation.

34. The antigen-binding protein of item 33, wherein the antibody comprises at least one Fc domain mutation that enhances binding of the antibody to human FcγRIIIa, preferably wherein the Fc domain mutation is at position 239, optionally S239D, and/or position 332, optionally I332E, wherein the residues are numbered according to EU numbering.

35. The antigen-binding protein of item 33 or 34, wherein the antibody comprises at least one Fc domain mutation that enhances antibody stability.

36. The antigen-binding protein of item 33, wherein the antibody comprises a pair of Fc domain mutations to cysteines, optionally wherein the mutations are at positions 292 and 302, optionally wherein the mutations are R292C and V302C, wherein the residues are numbered according to EU numbering.

37. The antigen-binding protein of any one of items 33-36, wherein said antibody comprises a heavy chain (HC) amino acid sequence and a light chain (LC) amino acid sequence that are at least 90% identical to the amino acid sequences of SEQ ID NOs: 10 and 11, respectively.

38. The antigen-binding protein of any one of items 29-37, wherein the antigen-binding protein is an afucosylated antibody.

39. The antigen-binding protein of any one of items 29-38, wherein said antigen-binding protein is a fusion protein.

40. The antigen-binding protein of any one of items 29-39, wherein said antigen-binding protein is bispecific or multispecific.

41. Isolated nucleic acid molecule(s) that encode the antigen-binding protein of any one of items 29-40.

42. Vector(s) comprising the isolated nucleic acid molecule(s) of item 41, wherein the vector(s) optionally comprise an expression control sequence.

43. Host cell(s) comprising the isolated nucleic acid molecule(s) of item 41 or the vector(s) of item 42.

44. A pharmaceutical composition comprising the antigen-binding protein of any one of items 29-40, the isolated nucleic acid molecule(s) of item 41, the vector(s) of item 42, or the host cell(s) of item 43, and a pharmaceutically acceptable excipient.

45. The antigen-binding protein according to any one of items 29-40, the isolated nucleic acid molecule(s) of item 41, the vector(s) of item 42, the host cell(s) of item 43, or the pharmaceutical composition according to item 44, for use as a medicament, preferably for use in treating cancer, more preferably wherein the cancer is multiple myeloma, non-Hodgkin's lymphoma, renal cancer, breast cancer, ovarian cancer, or pancreatic cancer.

46. A method for producing an antigen-binding protein, comprising providing the host cell(s) according to item 43, culturing said host cell(s) under conditions suitable for expression of the antigen-binding protein, and isolating the resulting antigen-binding protein from the culture.

47. A method for treating cancer in a patient in need thereof, comprising administering to said patient a therapeutically effective amount of the antigen-binding protein of any one of items 29-40 or the pharmaceutical composition of item 44.

48. The method of item 47, wherein the cancer is multiple myeloma, non-Hodgkin's lymphoma, renal cancer, breast cancer, ovarian cancer, or pancreatic cancer.

49. Use of the antigen-binding protein of any one of items 29-40, the isolated nucleic acid molecule(s) of item 41, the vector(s) of item 42, or the host cell(s) of item 43, for the manufacture of a medicament for treating a patient in need thereof, preferably wherein the patient has cancer, more preferably wherein the cancer is multiple myeloma, non-Hodgkin's lymphoma, renal cancer, breast cancer, ovarian cancer, or pancreatic cancer.

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. Throughout this specification and embodiments, the words "have" and "comprise," or variations such as "has," "having," "comprises," or "comprising," will be understood to imply the inclusion of a stated integer or group of integers but not the exclusion of any other integer or group of integers. As used herein, the term "approximately" or "about" as applied to one or more values of interest refers to a value that is similar to a stated reference value. In certain embodiments, the term refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context.

According to the present disclosure, back-references in the dependent claims are meant as short-hand writing for a direct and unambiguous disclosure of each and every combination of claims that is indicated by the back-reference. Any compound disclosed herein can be used in any of the treatment method here, wherein the individual to be treated is as defined anywhere herein. Further, headers herein are created for ease of organization and are not intended to limit the scope of the claimed invention in any manner.

In order that this invention may be better understood, the following examples are set forth. These examples are for purposes of illustration only and are not to be construed as limiting the scope of the invention in any manner.

EXAMPLES

Example 1: Generation of GPRC5D Binders and Preparation of Antibodies Engineered for Enhanced ADCC Activity GPRC5D binders were generated by phage display, followed by sequencing and screening in IgG format. Screening for specific binding to GPRC5D-expressing stable cell lines was measured by FACS. Several GPRC5D binders were identified, including clone 11.

Once the specific binders were identified, we investigated different "Fc enhanced" formats to increase affinity towards CD16a for enhanced ADCC functions. Specifically, the IgGs were converted into two formats: 1) DE-DSB (S239D/I332E mutations to the Fc region with R292C/V302C mutations to engineer a disulfide bond to stabilize the molecule; see, e.g., PCT Publication WO 2022/249146), and 2) afucosylated formats (GlymaxX® technology, Probiogen). Clone 11 in DE-DSB format is also referred as 11-DE-DSB, and clone 11 in afucosylated format is also referred to as 11-afuco.

An antibody directed to an irrelevant small molecule target was prepared in the different formats to serve as an isotype control (IC). The isotype control in different formats is referred to as IC-wt-IgG$_1$, IC-afuco and IC-DE-DSB.

As references for comparison, the VH and VL sequences of different anti-GPRC5D antibodies ("Benchmark 1" or "BM1", "Benchmark 2" or "BM2", "Benchmark 3" or "BM3" and "Benchmark 4" or "BM4") were used to prepare comparative antibodies. The BM1, BM2, BM3 and BM4 sequences are publicly available sequences for anti-GPRC5D portions of GPRC5D binding proteins. The comparative antibodies were prepared in wildtype IgG$_1$ format ("BM1 IgG$_1$ wt" or "BM2 IgG$_1$ wt," respectively), in afucosylated IgG$_1$ format ("BM1-afuco" and "BM2-afuco," respectively) and in DE-DSB format ("BM1-DE-DSB" and "BM2-DE-DSB," respectively). Both, BM1 and BM2 were selected as preferred benchmark because they are full competitors to the herein identified GPRC5D binder (clone 11) while BM3 and BM4 were only partial competitors.

Example 2: Assessment of Binding to FcγR by Surface Plasmon Resonance (SPR)

The interaction of the antibodies with human Fc receptors was analysed by SPR using a Biacore™ T200 instrument in the following test conditions:

Immobilization of anti-His antibodies on a CM5 sensor chip via amine coupling for seven Fcγ receptors: huFcγRI, huFcγRIIa_H131, huFcγRIIa_R131, huFcγRIIb/c, huFcγRIIIa_V158, huFcγRIIIa_F158, huFcγRIIIb, or use of biotin CAPture for the huFcRn analysis Capture of each of the Fc receptors Affinity constant determination by single cycle kinetics (SCK) at concentrations ranging from 0.6 nM to 2000 nM Interaction with huFcRn was studied at pH5.9 and pH7.4

Table 2.1 shows the K$_D$ values (mean of two replicates) of the recited antibodies for huFcγRIIIa (F158 and V158 polymorphs). Affinity to both polymorphs of FcγRIIIa was improved with the DE-DSB and afuco formats compared to wildtype IgG$_1$.

TABLE 2.1

Binding of anti-GPRC5D antibodies to huFcγRIIIa

| | huFcγRIIIa_F158 | | | huFcγRIIIa_V158 | | |
|---|---|---|---|---|---|---|
| | NormB | KD (M) | Fold change vs BM1 IgG$_1$ wt | NormB | KD (M) | Fold change vs BM1 IgG$_1$ wt |
| 11-DE-DSB | 45 | 2.27E−08 | 10 | 38 | 1.22E−08 | 4 |
| 11-afuco | 37 | 2.90E−08 | 8 | 34 | 4.93E−09 | 10 |
| BM1-afuco | 41 | 2.13E−08 | 11 | 36 | 3.57E−09 | 13 |
| BM1 IgG$_1$ wt | 16 | 2.35E−07 | 1 | 26 | 4.80E−08 | 1 |

Table 2.2 shows K$_D$ values (mean of two replicates) of the recited antibodies for huFcγRIIA (H167 and R167 polymorphs). No impact on affinity was observed for the DE-DSB and afuco formats compared to wildtype.

TABLE 2.2

Binding of anti-GPRC5D antibodies to huFcγRIIa

| | huFcγRIIa_H167 | | | huFcγRIIa_R167 | | |
|---|---|---|---|---|---|---|
| | NormB | KD (M) | Fold change vs BM1 IgG$_1$ wt | NormB | KD (M) | Fold change vs BM1 IgG$_1$ wt |
| 11-DE-DSB | 15 | 2.58E−06 | 1 | 2 | NB | NA |
| 11-afuco | 13 | 2.13E−06 | 1 | 2 | NB | NA |
| BM1-afuco | 8 | NB | NA | −4 | NB | NA |
| BM1 IgG$_1$ wt | 16 | 1.83E−06 | 1 | 1 | NB | NA |

NB = Non-Binder
NA = Non-Applicable

Table 2.3 shows K$_D$ values (mean of two replicates) of the recited antibodies for huFcγRI. No impact on affinity was observed for the DE-DSB and afuco formats compared to wildtype.

TABLE 2.3

Binding of anti-GPRC5D antibodies to huFcγRI

| | huFcγRI | | |
|---|---|---|---|
| | NormB | KD (M) | Fold change vs BM1 IgG$_1$ wt |
| 11-DE-DSB | 29 | 4.99E−10 | 2 |
| 11-afuco | 24 | 1.17E−09 | 1 |
| BM1-afuco | 28 | 9.22E−10 | 1 |
| BM1 IgG$_1$ wt | 25 | 1.03E−09 | 1 |

Table 2.4 shows K$_D$ values (mean of two replicates) of the recited antibodies for huFcRn, at pH5.9 and pH7.4. No impact on affinity was observed for the DE-DSB and afuco formats compared to wildtype.

TABLE 2.4

Binding of anti-GPRC5D antibodies to huFcRn

| | huFcRn | | | | |
|---|---|---|---|---|---|
| | NormB pH 6 | KD (M) pH 5.9 | Fold change vs BM1 IgG1 wt | NormB pH 7.4 | KD (M) pH 7.4 |
| 11-DE-DSB | 94 | 9.82E−07 | 1 | 27 | NB |
| 11-afuco | 103 | 4.08E−07 | 1 | 5 | NB |
| BM1-afuco | 84 | BAD FIT | NA | 6 | NB |
| BM1 IgG$_1$ wt | 96 | 5.91E−07 | 1 | 9 | NB |

NB = Non-Binder
NA = Non-Applicable

Table 2.5 shows K$_D$ values (mean of two replicates) of the recited antibodies for huFcγRIIIb. Affinity to FcγRIIIb was improved with the DE-DSB and afuco formats compared to wildtype IgG$_1$.

TABLE 2.5

Binding of anti-GPRC5D antibodies to huFcγRIIIb

| | huFcγRIIIb | | |
|---|---|---|---|
| | NormB | KD (M) | Fold change vs BM1 IgG$_1$ wt |
| 11-DE-DSB | 35 | 5.29E−08 | 34 |
| 11-afuco | 33 | 1.83E−07 | 10 |
| BM1-afuco | 32 | BAD FIT | NA |
| BM1 IgG$_1$ wt | 21 | 1.82E−06 | 1 |

NA = Non-Applicable

Example 3: Cellular Binding of ADCC-Enhanced Antibodies to HEK Cells Overexpressing Human and Cynomolgus FcγRIIIa The antibodies were tested using FACS for their ability to bind cells that express human or cynomolgus FcγRIIIa on their surface. The cell lines used were recombinant stable HEK293 T cells expressing human FcγRIIIa V158 and cynomolgus FcγRIIIa to assess cynomolgus cross-reactivity.

Flow cytometry binding assays were performed with a MACSQuant16 (Miltenyi Biotech) Flow Cytometer using 96-well plates.

For dose-response curves, cells were incubated with a serial dilution of the antibodies (from 0.0001 μg/mL to 100 μg/mL) for 1 h at 4° C. After one washing step in PBS buffer, the cells were incubated with the secondary detection antibody diluted at 1/1000 following manufacturer's recommendations (goat anti human IgG (H+L) conjugated with A488 fluorochrome; Jackson ImmunoResearch, cat. no. 109-546-088) for 30 min at 4° C. followed by two washing steps. For live/dead cell viability assessment, cells were stained according to manufacturer's protocol using DAPI staining solution (4',6-diamino-2-phenylindole, dihydrochloride, Miltenyi Biotech, cat. no. 130-111-170).

Analyses were performed with VenturiOne® Software. Cells were first gated in FSC/SSC. From the resulting cell population, single cells and following viable cells were gated. Binding was analyzed as median fluorescence intensity (MFI) of the secondary antibody.

The apparent K$_D$ was determined for each molecule by drawing an appropriate non-linear regression curve using the one site-specific binding four parameters model with GraphPad Prism Software (FIG. 1).

Table 3.1 shows FACS data for the binding of the antibodies to cynomolgus and human FcγRIIIa-expressing HEK293 T cells. Comparator anti-GPRC5D antibody Benchmark 2 (BM2) was introduced in $IgG_1$ wildtype format as a reference. The mean of three experiments is reported.

TABLE 3.1

Binding of anti-GPRC5D antibodies to HEK293 cells expressing human or cynomolgus FcγRIIIa

|  | HEK293 T human FcγRIIIa V158 | | HEK293 T cyno FcγRIIIa | |
| --- | --- | --- | --- | --- |
|  | Apparent KD (nM) | Fold change vs $IgG_1$ wt | Apparent KD (nM) | Fold change vs $IgG_1$ wt |
| 11-DE-DSB | 1.22 | 28 | 1.4 | 26 |
| 11-afuco | 1.04 | 33 | 0.76 | 48 |
| BM2 $IgG_1$ wt | 34.04 | 1 | 36.5 | 1 |

Clone 11 in both formats (DE-DSB and afuco) showed similar affinity for human and cynomolgus FcγRIIIa (from 0.76 to 1.4 nM). Affinity to both human and cynomolgus FcγRIIIa is improved in both formats compared to wildtype $IgG_1$ format (from 26- to 48-fold increase).

Example 4: Binding of ADCC-Enhanced Antibodies to Multiple Myeloma MM.1R Cell Line and to HEK Cells Overexpressing Human GPRC5D (hGPRC5D)

Binding to Cell Lines

FACS analyses were performed to determine the ability of the ADCC-enhanced antibodies to bind to cells that express GPRC5D on their surface. The cell lines used were:
  multiple myeloma cell line MM.1R (purchased from ATCC—the American Type Culture Collection),
  recombinant stable Flp-In™_293 cells expressing human and cynomolgus GPRC5D to assess cynomolgus cross-reactivity,
  stable HEK FITR cells expressing human GPRC5D (full-length or truncated with an N-terminal deletion of the first 15 or 20 residues) to document GPRC5D binding domains, and
  FreeStyle™ 293-F cells expressing human GPRC5A/GPRC5D chimeras where the N-terminal domain and extracellular loops of GPRC5D were substituted by those of GPRC5A, to document GPRC5D binding domains.

Binding to the REC-1 cell line (purchased from ATCC), negative for GPRC5D expression, was also studied to assess the specificity of the recited antibodies.

Flow cytometry binding assays were performed with an iQue Screener Flow Cytometer using 384-well plates.

For dose-response-curves, cells were incubated with a serial dilution of the antibodies at several concentrations for 1 h at 4° C. After three washing steps, the cells were incubated with the secondary detection antibody (Goat Anti human IgG A488) for 30 min at 4° C. followed by three washing steps. For live/dead cell discrimination, cells were stained with DAPI according to the manufacturer's protocol.

Figure 2:
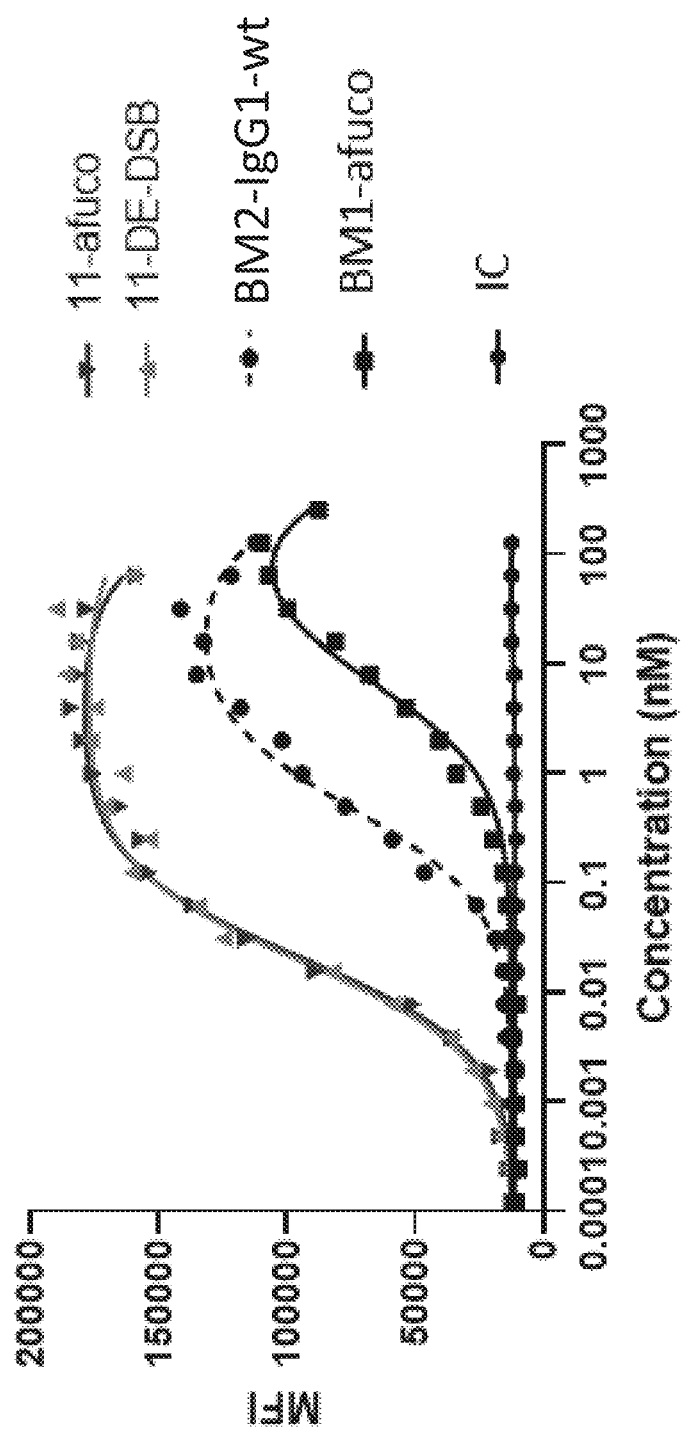
FIG. 2 is a line graph depicting the median fluorescence intensity (MFI) for antibody binding at different concentrations to MM.1R (a MM cell line which expresses GPRC5D), as assessed by FACS. 11-afuco: clone 11 in afucosylated format. 11-DE-DSB: clone 11 in DE-DSB format. BM1-afuco: Benchmark 1 antibody in afucosylated format. BM2-IgG$_1$-wt: Benchmark 2 antibody in IgG$_1$ wildtype format. IC: IgG$_1$ isotype control.

Analyses were performed with Forecyt® Software. Cells were first gated in FSC (forward scatter)/SSC (side scatter). From the resulting cell population, single live cells were gated. Binding was analyzed as median fluorescence intensity (MFI) of the secondary antibody. Curves and apparent $K_D$ ("App$K_D$") calculations were generated using GraphPad Prism Software (FIG. 2).

Table 4.1 presents FACS data for binding of the recited antibodies to cynomolgus and human GPRC5D-expressing Flp-In™-293 cells. Non-transfected Flp-In™-293 cells were used to evaluate binding specificity for GPRC5D. Isotype control $IgG_1$ in wildtype format ("IC-$IgG_1$-wt") was used as a negative control. BM1 and BM2 were introduced as references.

TABLE 4.1

Binding of anti-GPRC5D antibodies to human and cynomolgus GPRC5D

|  | Apparent $K_D$ (nM) | | |
| --- | --- | --- | --- |
|  | Flp-In ™-293 huGPRC5D | Flp-In ™-293 cyGPRC5D | Flp-In ™-293 |
| 11-afuco | 2.2 | 1.3 | NB |
| BM2-$IgG_1$-wt | 4.4 | >10 | NB |
| BM1-afuco | 0.8 | 4.6 | NB |
| BM3-$IgG_1$-wt | 5.8 | NB | NB |
| IC-$IgG_1$-wt | NB | NB | NB |

NB = No Binding

The 11-afuco, BM1-afuco, BM2-$IgG_1$-wt and BM3-$IgG_1$-wt antibodies all bound to human GPRC5D expressed on Flp-In™-293 cells. 11-afuco, BM1-afuco and BM2-$IgG_1$-wt antibodies also bound to cynomolgus GPRC5D-expressed on Flp-In™-293 cells, with the BM2-$IgG_1$-wt antibody binding at the lowest affinity. BM3-$IgG_1$-wt did not bind to cynomologous GPRC5D expressed on Flp-In™_293 cells.

Table 4.2 presents FACS data for binding of the recited antibodies to truncated variants of human GPRC5D expressed in HEK FITR cells. IC-$IgG_1$-wt was used as a negative control. BM1, BM2 and BM3 were introduced as references.

TABLE 4.2

Binding of anti-GPRC5D antibodies to truncated variants of GPRC5D

|  | Apparent $K_D$ (nM) | | |
| --- | --- | --- | --- |
|  | HEK FITR hGPRC5D (Full Length) | HEK FITR hGPRC5D (aa16-aa330) | HEK FITR hGPRC5D (aa21-aa330) |
| 11-afuco | 1.3 | 0.8 | 1.0 |
| BM2-$IgG_1$-wt | 0.9 | 0.9 | 1.1 |
| BM1-afuco | 1.0 | NB | NB |
| BM3-$IgG_1$-wt | 2.5 | NB | NB |
| IC-$IgG_1$-wt | NB | NB | NB |

NB = No Binding

These results highlight differences in how the 11-afuco antibody binds to GPRC5D compared to the BM1-afuco antibody.

Table 4.3 presents FACS data for binding of the recited antibodies to cells expressing GPRC5D/GPRC5A chimeric proteins. IC-$IgG_1$-wt was used as negative control. BM1 and BM2 were introduced as references. SEQ: SEQ ID NO.

TABLE 4.3

Binding of anti-GPRC5D antibodies to GPRC5D/GPRC5A chimeric proteins

| | | MFI | | | | |
|---|---|---|---|---|---|---|
| | hGPRC5D | hGPRC5D-GPRC5A chimera (Nter) SEQ: 15 | hGPRC5D-GPRC5A chimera (aa85-aa93) SEQ: 16 | hGPRC5D-GPRC5A chimera (aa145-aa167) SEQ: 17 | hGPRC5D-GPRC5A chimera (aa226-aa239) SEQ: 18 | non transfected FreeStyle™ 293-F |
| 11-DE-DSB | 587 493 | 217 763 | 507 810 | 289 111 | 497 561 | 18 091 |
| 11-afuco | 600 694 | 147 291 | 483 366 | 248 171 | 526 500 | 14 527 |
| BM2-afuco | 900 821 | 156 546 | 54 632 | 19 919 | 373 870 | 11 911 |
| BM1-afuco | 717 740 | 20 861 | 195 703 | 696 229 | 288 061 | 15 635 |
| IC-IgG$_1$-wt | 27 418 | 24 667 | 29 669 | 32 504 | 29 760 | 16 933 |

These results highlight differences in how the 11 antibodies (DE-DSB and afuco) bind to GPRC5D compared to the BM1-afuco and BM2-afuco antibodies.

Table 4.4 presents FACS data for binding of the recited antibodies to multiple myeloma MM.1R cells positive for GPRC5D. BM1, BM2 and BM3 were introduced as references.

TABLE 4.4

Binding of anti-GPRC5D antibodies to multiple myeloma cells

| | Apparent KD (pM) MM.1R | | | |
|---|---|---|---|---|
| | N = 1 | N = 2 | N = 3 | mean |
| 11-DE-DSB | 36 | 18 | 19 | 24 |
| 11-afuco | 35 | 17 | 24 | 25 |
| BM1-afuco | 19370 | 6935 | 11000 | 12435 |
| BM2-IgG$_1$-wt | 869 | 365 | 426 | 553 |
| BM3-IgG$_1$-wt | 630 | | | 630 |

These results demonstrate that the 11-DE-DSB and 11-afuco antibodies bind to GPRC5D expressed on MM.1R cells with markedly higher affinity than the BM1-afuco, BM2-IgG$_1$-wt or BM3-IgG$_1$-wt antibodies.

Example 5: In Vitro Short-Term ADCC Activity Against MM Cell Lines with Different GPRC5D Density To determine the number of GPRC5D molecules per cell, a flow cytometry-based GPRC5D receptor assay was used to quantify GPRC5D surface expression and subsequently select MM cell lines that would be suitable for downstream analysis of GPRC5D antibodies. MM.1R and EJM cell lines were chosen in a panel of MM cell lines for their GPRC5D expression at high and medium levels, respectively.

Briefly, for GPRC5D density determination, the CELL-QUANT Calibrator (BioCytex, cat. no. 7208) was used following manufacturer's recommendations. MM cells were incubated with a mouse anti-human GPRC5D antibody at 1/500 (monoclonal mouse IgG2B clone no. 571961, R&D Systems). After two consecutive washing steps in reagent R1, cells were labelled with anti-mouse IgG FITC secondary antibody (Reagent 3 in the BioCytex kit, cat. no. 7208) diluted at 1/10 in R1 reagent. In parallel, calibration beads were added to wells dedicated to calibration and treated to be in the same staining conditions as the cells. The 96-well plate was then incubated for 20 min at 4° C., protected from light.

After incubation and washing steps followed by centrifugation, cells were resuspended in reading buffer before reading with MACSQuant® Analyzer 10 (Miltenyi Biotec).

To determine GPRC5D density on MM cell lines (based on FITC fluorescence), the calibration bead information was used to generate a linear calibration curve. GPRC5D density per cell was calculated using the following formula:

$$\text{GPRC5D density} = 10^{(\log(FITC\ GPRC5D)*a+b)} - 10^{(\log(FITC\ isotype)*a+b)}$$

The calculation of GPRC5D density per cell for the panel of MM cell lines revealed that the MM.1R cell line had the highest level of GPRC5D density (around 30,500 antigens per cell) and the EJM cell line had a medium level of GPRC5D density (around 8,500 antigens per cell) at the cell surface compared to other MM cell lines used in the panel.

The list of all tested MM cell lines and their GPRC5D densities are shown in Table 5.1 (data shown are based on a mean of six to seven experiments).

TABLE 5.1

GPRC5D density in MM cell lines

| MM Cell line Name | Cell Bank | GPRC5D antigen per cell |
|---|---|---|
| H929 | ATCC | 3,238 |
| U266 | DSMZ | 455 |
| OPM2 | DSMZ | 7,664 |
| MM.1R | ATCC | 30,526 |
| JJN3 | DSMZ | 3,292 |
| KMS12BM | DSMZ | 0 |
| L363 | DSMZ | 2,040 |
| RPMI 8226 | ATCC | 421 |
| LP1 | DSMZ | 402 |
| MOLP8 | DMSZ | 1,748 |
| KMS11 | JCRB | 0 |
| EJM | DSMZ | 8,560 |

To measure the short-term functionality of the anti-GPRC5D enhanced ADCC antibodies, an in vitro NK cell cytotoxicity assay was performed. The anti-GPRC5D ADCC-enhanced engineered antibodies in different Fc formats (Fc-afucosylated, Fc-DE-DSB) were evaluated for their ability to promote lysis of MM tumor cells in the presence of NK cells purified from healthy donors. Two additional anti-GPRC5D antibodies were tested in parallel as benchmarks (BM1 and BM2).

In detail, human NK cells were purified from healthy donor buffy coats, provided by the Etablissement Français du Sang (EFS, the French blood service, Rungis). Peripheral mononuclear cells (PBMC) were isolated from buffy coats by Ficoll density gradient centrifugation. Human NK cells were purified from PBMC with a bead-based negative selection kit from Miltenyi Biotec (MACSxpress® Cell Isolation kit, cat. no. 130-098-185). MM.1R and EJM MM cell lines were purchased from ATCC. Cells were cultured in complete RPMI medium (RPMI-1640 containing 10% FBS, 2 mM L-glutamine). For cytotoxic assays, target tumor cells were alternatively loaded with calcein (Invitrogen cat. no. C3100MP) following provider's recommendation. All antibodies and isotype controls (ICs) were tested in a range of concentrations from 0.00001 to 100 µg/mL. All tested antibodies and corresponding ICs were distributed in the appropriate wells of a round-bottomed 96-well plate. Then, human NK cells (effector cells, ~100,000 cells) from healthy donors (fresh or allowed to rest overnight) and labeled tumor cells (target cells, ~10,000 cells) were added to obtain an E:T ratio (Effector:Target cell ratio) of 10:1. In some wells, TRITON X-100 (Sigma-Aldrich) was added as positive control for tumor cell lysis as it induces 100% of cell lysis. After 2 h of co-incubation at 37° C. and 5% $CO_2$, the supernatant was transferred to black 96-well plates and the amount of calcein released was assessed using the TECAN Infinite® 1000 counter. The percent specific lysis was calculated with the following formula:

Specific lysis (%)=(Treated cells−cells alone)/(Triton treated cells−cells alone)×100

The EC50 was determined for each molecule by drawing an appropriate non-linear regression curve (choice of "log (agonist) vs. response–variable slope (four parameters)" model) with GraphPad Prism Software. The results are expressed in AFU=arbitrary fluorescent units.

Figure 3:
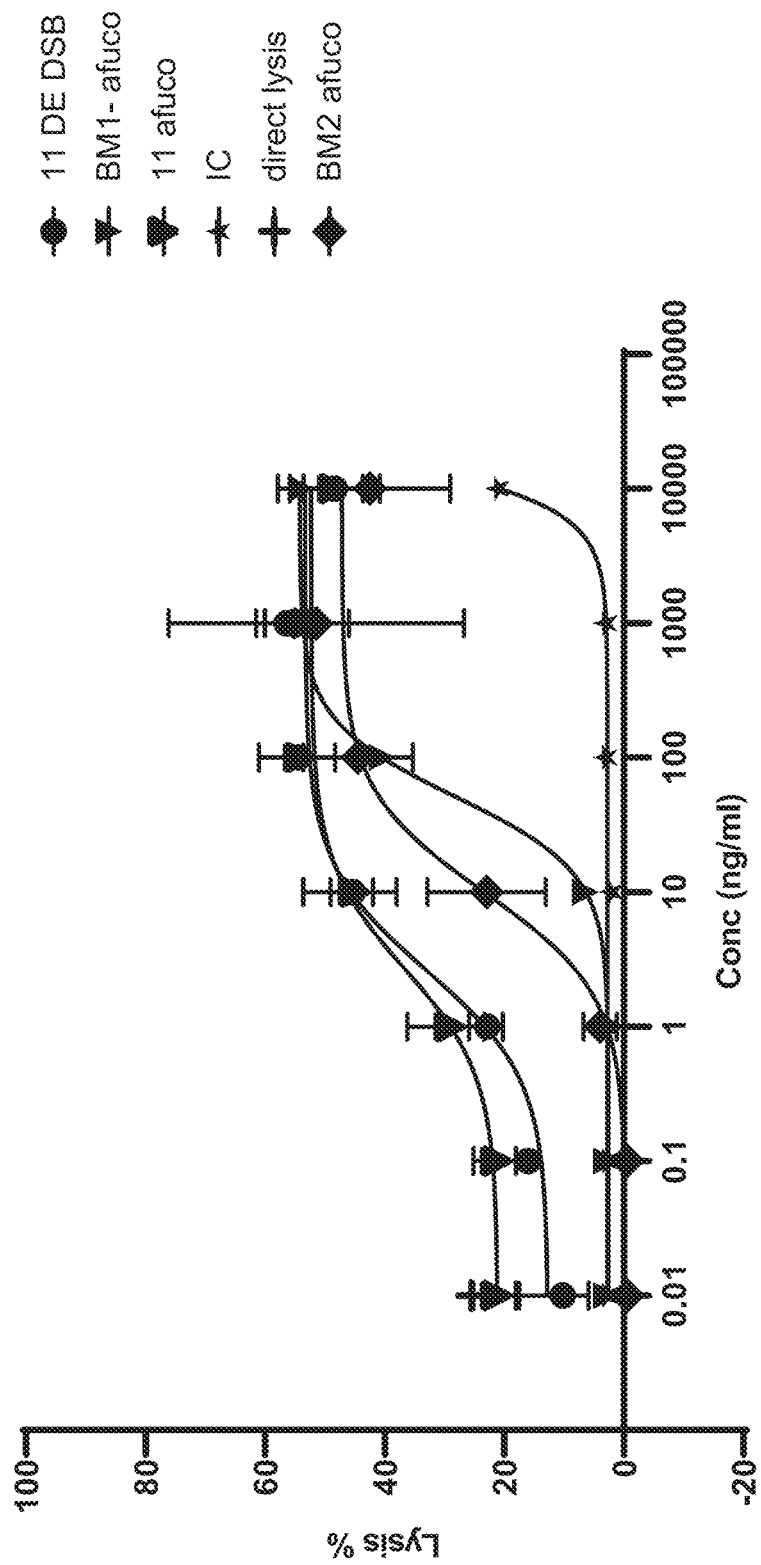
FIG. 3 is a line graph showing antibody dependent cellular cytotoxicity (ADCC) activity of different concentrations of clone 11 in afucosylated ("afuco") and DE-DSB formats against MM.1R cells, as assessed by percent of lysis (calcein release read-out). Isotype control IgG$_1$ DE-DSB (IC) was used as a negative control. Benchmark 1 and 2 antibodies in afucosylated format (BM1 afuco and BM2 afuco, respectively) were also assessed as references. Data shown are from one representative experiment out of five.

Table 5.2 presents the ADCC activity of the recited antibodies against MM.1R MM cells (FIG. 3). Calcein release read-out was used to evaluate lysis percentage. BM1 afuco and BM2 afuco were introduced as benchmark references.

TABLE 5.2

| ADCC activity of anti-GPRC5D antibodies against MM.1R cells | | | | |
|---|---|---|---|---|
| | 11 DE-DSB | 11 afuco | BM2-afuco | BM1-afuco |
| Number of values | 4 | 5 | 5 | 4 |
| relEC50 Median ng/ml (pM) | 6.0 (40.1) | 5.4 (36) | 22.3 (154) | 249.5 (1,663) |
| 95% CI of median | | | | |
| Actual confidence level | 87.50% | 93.75% | 93.75% | 87.50% |
| Lower confidence limit | 2.6 | 0.3 | 10.1 | 51.8 |
| Upper confidence limit | 10.6 | 11.1 | 45.3 | 1,151 |

Clone 11 in DE-DSB and afucoslated formats shows high picomolar ADCC activity against MM MM1.R cells in the presence of NK cells (EC50 of 40.1 and 36 µM, respectively). This activity is superior to the activity found with the anti-GPRC5D benchmarks BM2-afuco and BM1-afuco (relEC50 (of 154 and 1,663 pM, respectively).

Figure 4:
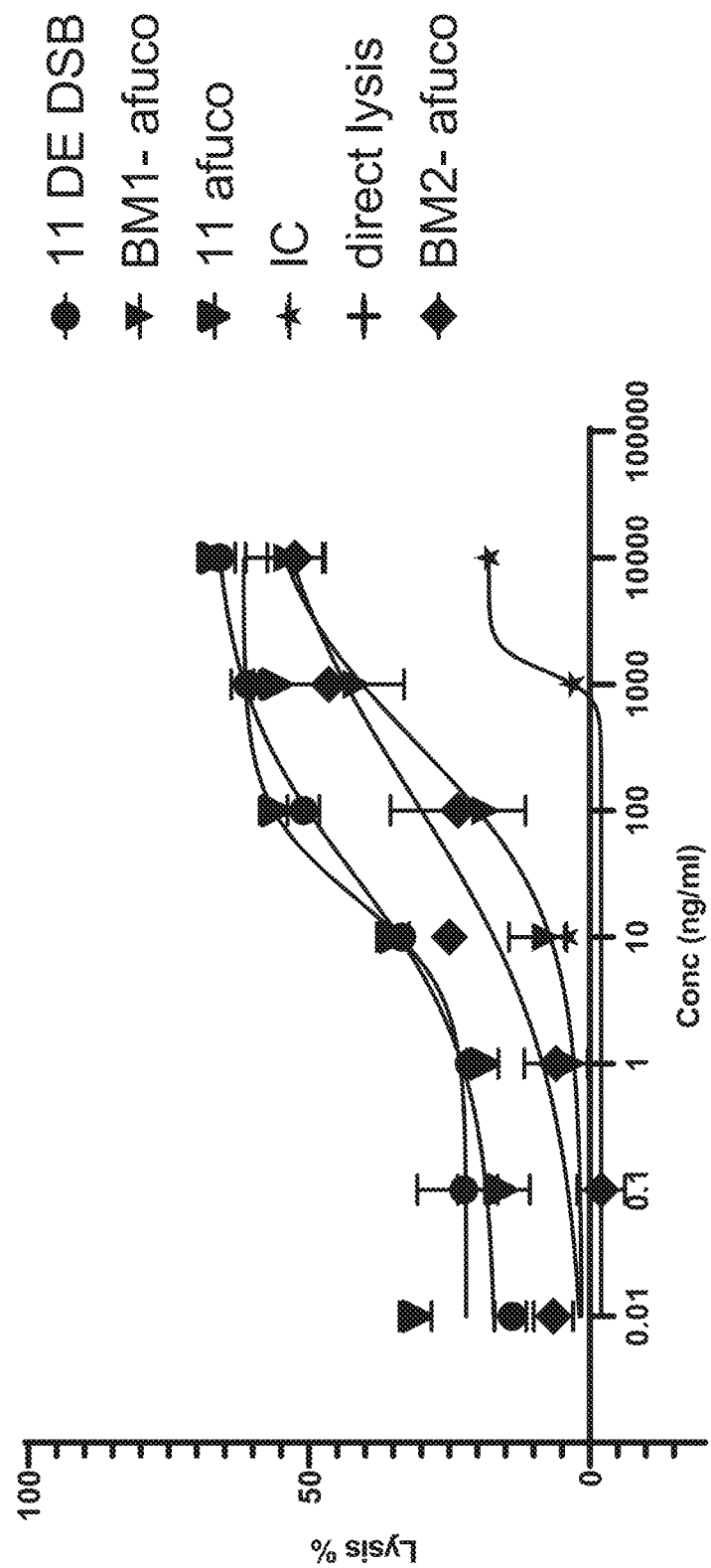
FIG. 4 is a line graph showing the ADCC activity of different concentrations of clone 11 in afucosylated ("afuco") and DE-DSB formats against EJM, a MM cell line, as assessed by percent of lysis (calcein release read-out). Isotype control IgG$_1$ DE-DSB (IC) was used as a negative control. Benchmark 1 and 2 antibodies in afucosylated format (BM1 afuco and BM2 afuco, respectively) were also assessed as references. Data shown are from one representative experiment out of five.

Table 5.3 presents the ADCC activity of the recited antibodies against EJM MM cells (FIG. 4). Calcein release read-out was used to evaluate lysis percentage. BM1 afuco and BM2 afuco were introduced as benchmark references.

TABLE 5.3

| ADCC activity of anti-GPRC5D antibodies against EJM cells | | | | |
|---|---|---|---|---|
| | 11 DE-DSB | 11 afuco | BM2-afuco | BM1-afuco |
| Number of values | 4 | 5 | 4 | 3 |
| relEC50 Median | 37.5 | 20.5 | 70.9 | 502.4 |

TABLE 5.3-continued

| ADCC activity of anti-GPRC5D antibodies against EJM cells | | | | |
|---|---|---|---|---|
| | 11 DE-DSB | 11 afuco | BM2-afuco | BM1-afuco |
| ng/ml (pM) | (259) | (141) | (489) | (3,460) |
| 95% CI of median | | | | |
| Actual confidence level | 87.50% | 93.75% | 87.50% | 75.00% |
| Lower confidence limit | 26.55 | 14.24 | 16.7 | 347.5 |
| Upper confidence limit | 57.21 | 128.7 | 130 | 974.2 |

Clone 11 in DE-DSB and afucosylated formats shows high picomolar ADCC activity against EJM cells in the presence of NK cells (EC50 of 259 and 141 pM, respectively). This activity is superior to the activity found with the anti-GPRC5D benchmarks BM2-afuco and BM1-afuco (relEC50 of 489 and 3,460 pM, respectively).

Example 6: In Vitro Long-Term ADCC Activity Against MM.1R MM Cell Lines

To assess the long-term functionality of the anti-GPRC5D enhanced ADCC antibodies, an in vitro NK cell cytotoxicity assay was performed over a period of four days using the Incucyte® S3 Live-Cell Analysis Instrument (Sartorius). The anti-GPRC5D ADCC-enhanced engineered antibodies in different Fc formats (Fc-afucosylated, Fc-DE-DSB) were evaluated for their ability to promote lysis of MM tumor cells in the presence of NK cells purified from healthy donors. Two additional anti-GPRC5D antibodies were tested in parallel as benchmarks (BM1 and BM2).

Briefly, human NK cells were purified from healthy donor buffy coats, provided by the Etablissement Français du Sang (EFS, the French blood service, Rungis). Peripheral mononuclear cells (PBMC) were isolated from buffy coats by Ficoll density gradient centrifugation. Human NK cells were purified from PBMC with a bead-based negative selection kit from Miltenyi Biotec (MACSxpress Whole Blood NK Cell Isolation kit; cat. no. 130-127-695). Purified human NK cells were incubated overnight in complete RPMI medium (RPMI-1640 containing 10% FBS, 2 mM L-glutathione). MM.1R MM cell lines were purchased from ATCC. An MM.1R-RFP (red fluorescent protein) stable cell line was established by infection with a third-generation lentivirus HIV-based, VSV-G pseudotyped lentiviral, coding for RFP (mKate2 Lentivirus Reagent; Sartorius; cat. no. 4625). The selection of MM.1R-RFP cells was performed through the addition of puromycin dihychloride hydrate (Thermo Scientific, Denmark, cat. no. 10781691) at a final concentration of 1 µg/mL in the complete RPMI culture medium (RPMI-1640 containing 10% FBS, 2 mM L-glutamine). For cytotoxicity assays, all antibodies were tested in a range of concentrations from 0.00001 to 100 µg/mL. The diluted molecules, the labeled target cells (6,000 cells) and the rested human NK cells (18,000 cells) from healthy donors were successively added to each well of black 384-well plates to obtain a 3:1 E:T ratio (Effector:Target cell ratio). The plates were incubated at 37° C., 5% $CO_2$ in the Incucyte® S3 Live-Cell Analysis Instrument (Sartorius) taking pictures every four hours for four days (phase and red image channels; 20× magnification). The results are expressed in Red Object Count Per Image Normalized to 0d0h0m (%). The percentage of specific lysis was calculated with the following formula:

Specific lysis (%)=(untreated cells without NK-Treated cells with NK)/(untreated cells withoutNK)×100

The relative EC50 was determined for each molecule by drawing an appropriate non-linear regression curve (choice of "log(agonist) vs. response–variable slope (four parameters)" model) with GraphPad Prism Software.

Table 6.1 indicates the ADCC activity of the recited antibodies against MM.1R MM cells. Incucyte imaging read-out was used to evaluate lysis percentage. BM1 afuco and BM2 afuco were introduced as benchmark references.

TABLE 6.1

ADCC activity of anti-GPRC5D antibodies against MM.1R over four days

|  | 11 DE-DSB | 11 afuco | BM2-afuco | BM1-afuco |
|---|---|---|---|---|
| Number of values | 3 | 3 | 3 | 3 |
| relEC50 median ng/ml (pM) | 0.87 (6) | 0.50 (3.45) | 0.96 (6.62) | 25.40 (175) |
| 95% CI of median |  |  |  |  |
| Actual confidence level | 75.00% | 75.00% | 75.00% | 75.00% |
| Lower confidence limit | 0.83 | 0.42 | 0.08 | 22.21 |
| Upper confidence limit | 0.88 | 0.93 | 0.99 | 29.80 |

Figure 5:
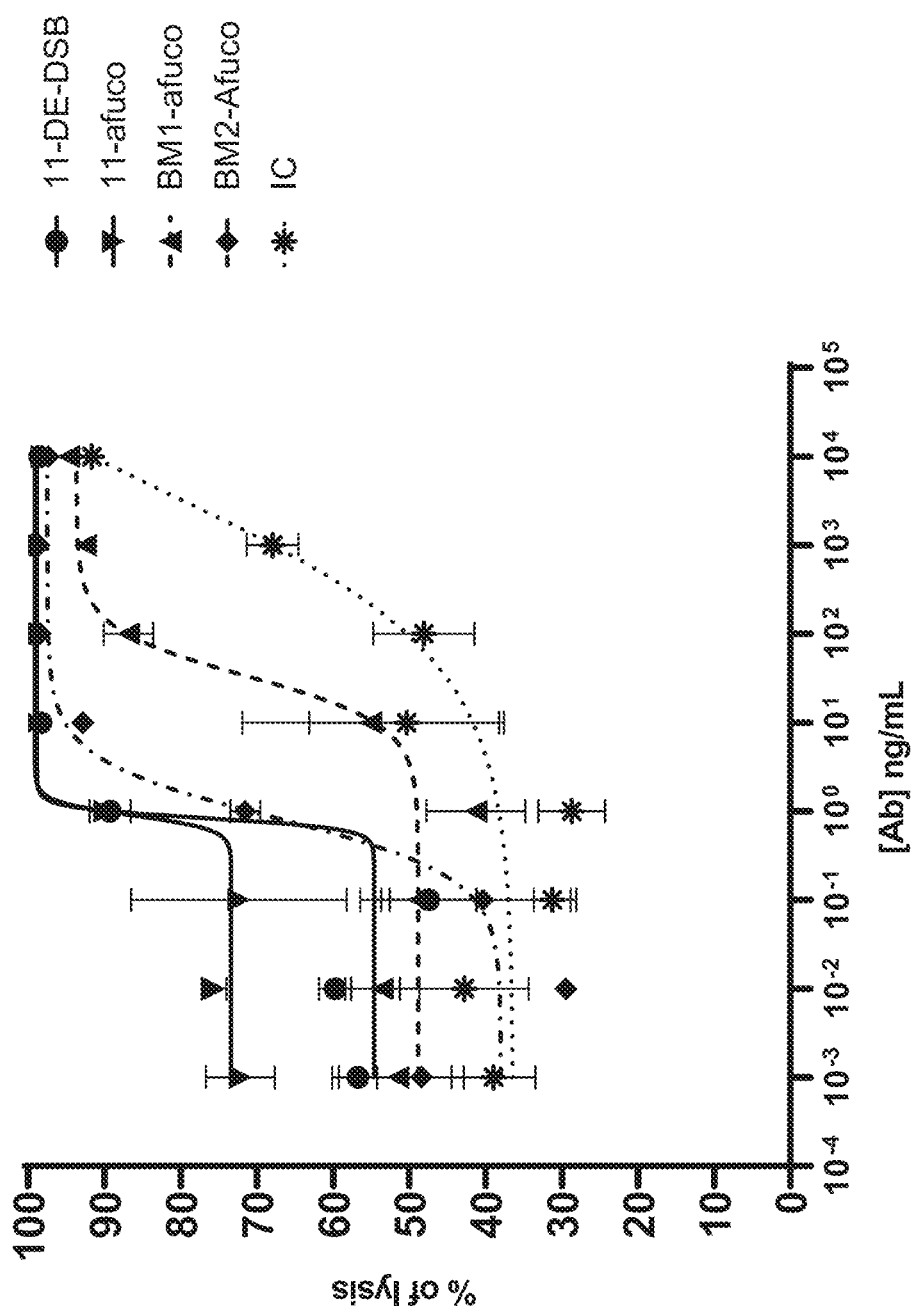
FIG. 5 is a line graph showing the ADCC activity at Day 4 of different concentrations of clone 11 in afucosylated ("afuco") and DE-DSB formats against MM.1R MM cells as assessed by percent lysis (Incucyte imaging read-out). Isotype control IgG$_1$ DE-DSB (IC) was used as a negative control. Benchmark 1 and 2 antibodies in afucosylated format (BM1 afuco and BM2 afuco, respectively) were also assessed as references. Data shown are from one representative experiment out of two.
Figure 6:
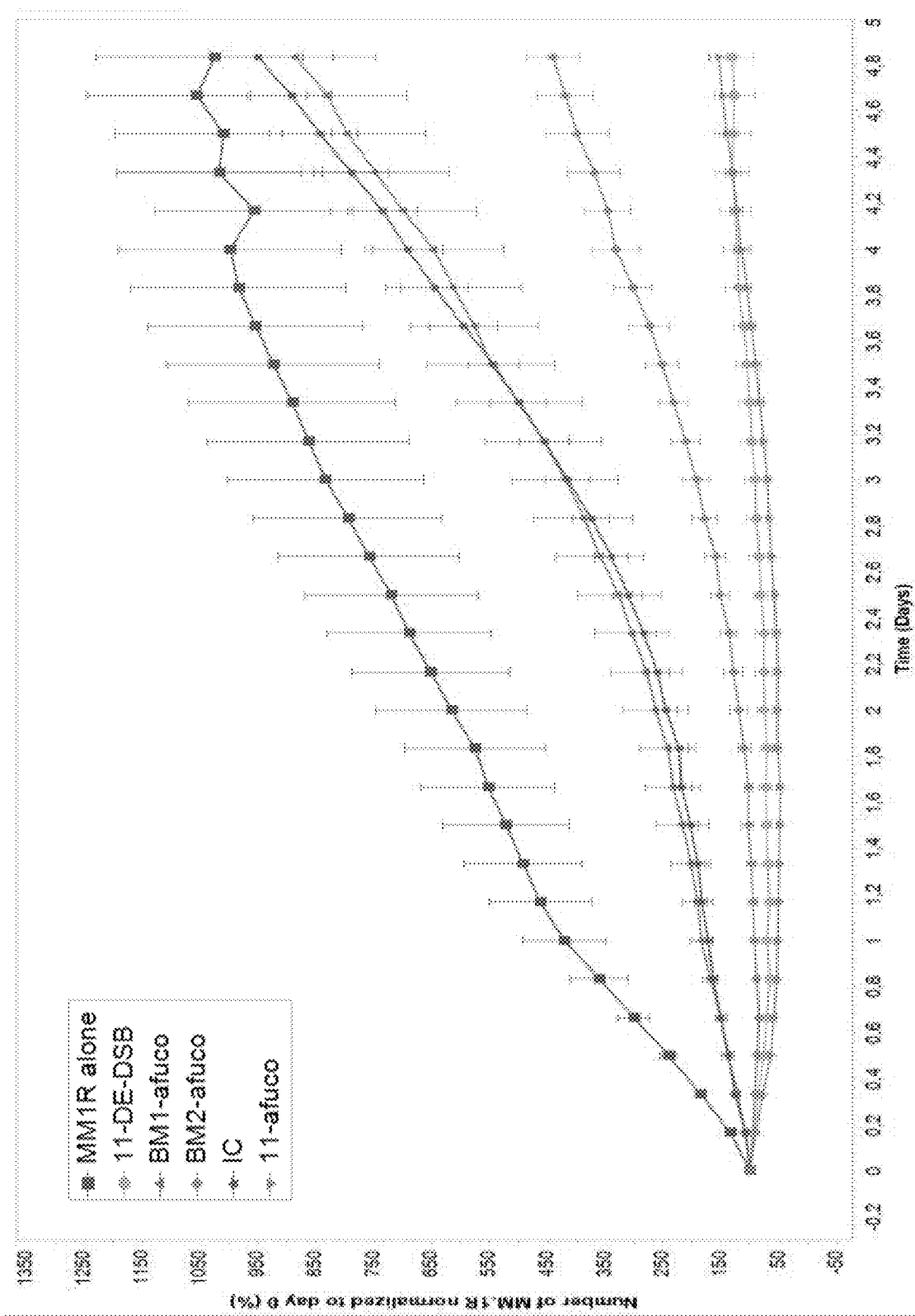
FIG. 6 is a line graph depicting the ADCC activity of clone 11 in afucosylated ("afuco") and DE-DSB formats against MM.1R MM cells as assessed by MM.1R count normalized to Day 0 measured over four days. Isotype control IgG$_1$ DE-DSB (IC) was used as a negative control. Benchmark 1 and 2 antibodies in afucosylated format (BM1 afuco and BM2 afuco, respectively) were also assessed as references. Data shown are from one representative experiment after overnight incubation in the presence of NK cells and 1 ng/mL of antibodies.

Clone 11 in DE-DSB and afucosylated formats shows high picomolar ADCC activity against MM.1R cells in presence of NK cells after four days of incubation time (EC50 median of 6 and 3.5 pM respectively) (FIG. 5). In both DE-DSB and afucosylated formats, Clone 11 shows a higher cytotoxic activity against MM.1R cells over four days than the BM1-afuco and BM2-afuco antibodies (FIG. 6). Anti-GPRC5D antibody BM2 in afucosylated format shows similar activity (relEC50 median of 6.6 pM). Anti-GPRC5D antibody BM1 in afucosylated format shows lower cytotoxic activity with a relEC50 median of 175 pM.

Example 7: Cytokine Release in a MM.1R Co-Culture in a PBMC Setting

This experiment evaluated the in vitro effect of clone 11 in DE-DSB format on the release of cytokines by peripheral blood mononuclear cells (PBMC) in the presence of a GPRC5D and BCMA positive cell line (MM.1R multiple myeloma cells).

Briefly, for the cytokine release assay, PBMCs were isolated from healthy human donor buffy coats (provided by the Etablissement Français du Sang (EFS, the French blood service, Rungis) using Ficoll density gradient centrifugation. The MM.1R multiple myeloma cell line was purchased from ATCC. Cells were cultured in complete RPMI medium (RPMI-1640 containing 10% FBS, 2 mM L-glutamine). An anti-BCMAXCD3 T-cell engager was used as a positive control, as BCMA is expressed on MM.1R cells. Clone 11 in DE-DSB format and the controls were tested at 20 nM and 20 pM. The target cells (10,000 cells) and the human PBMC cells (500,000 cells) from healthy donors were successively seeded in each 96-well plates to obtain a 50:1 E:T ratio (Effector:Target cell ratio). The tested molecule and positive controls were added in co-culture. After overnight co-incubation at 37° C., 5% $CO_2$, the plate was centrifuged at 300 g for 5 min. Then 100 µL of supernatant/well were collected to perform the cytokine release analysis. For the analysis, the Human Proinflammatory I (4-Plex) Kit V-PLEX was used (Mesoscale MSD, cat. no. K15052D-1) following provider's recommendations. IFNγ, IL-6, and TNFα cytokines were quantified in the same well. The calibration curves used to calculate the concentration for each analyte were established by fitting the signal from the calibrators to a four-parameter logistic model. Analyte concentrations (pg/mL) were determined from the ECL signals by back-fitting to the calibration curve.

Table 7.1 presents data on cytokine release induced by clone 11 in DE-DSB format from human PBMCs in the presence of GPRC5D positive MM.1R cells (mean of five experiments). Isotype control IgG$_1$ DE-DSB (IC) was used as a negative control. Anti-BCMAXCD3 TCE was introduced as a positive control.

TABLE 7.1

Cytokine release induced by anti-GPRC5D antibodies

|  | IFNγ | | | | IL-6 | | | | TNF-α | | | |
|---|---|---|---|---|---|---|---|---|---|---|---|---|
|  | Mean pg/mL | SD | N | FC | Mean pg/mL | SD | N | FC | Mean pg/mL | SD | N | FC |
| Untreated baseline | 29 | 18 | 5 |  | 14 | 14 | 4 |  | 214 | 195 | 5 |  |
| IC 100 nM | 27 | 13 | 3 | 0.9 | 9 | 1 | 2 | 0.6 | 233 | 310 | 3 | 1.1 |
| 11 DE-DSB 100 nM | 90 | 21 | 3 | 3.1 | 17 | 3 | 3 | 1.2 | 486 | 474 | 4 | 2.3 |
| 11 DE-DSB 20 nM | 75 | 31 | 5 | 2.6 | 12 | 8 | 4 | 0.9 | 457 | 617 | 5 | 2.1 |
| CD3-BCMA TCE 100 nM | 1223 | 712 | 3 | 42 | 36 | 27 | 3 | 2.6 | 2650 | 2839 | 4 | 12 |
| CD3-BCMA | 733 | 432 | 5 | 25 | 51 | 39 | 4 | 1.8 | 1396 | 1619 | 5 | 6.5 |

TABLE 7.1-continued

| Cytokine release induced by anti-GPRC5D antibodies ||||||||||||
| --- | --- | --- | --- | --- | --- | --- | --- | --- | --- | --- | --- |
| IFNγ |||| IL-6 |||| TNF-α ||||
| Mean pg/mL | SD | N | FC | Mean pg/mL | SD | N | FC | Mean pg/mL | SD | N | FC |
| TCE 20 nM | | | | | | | | | | | |

FC: fold change vs. baseline

Figure 7:
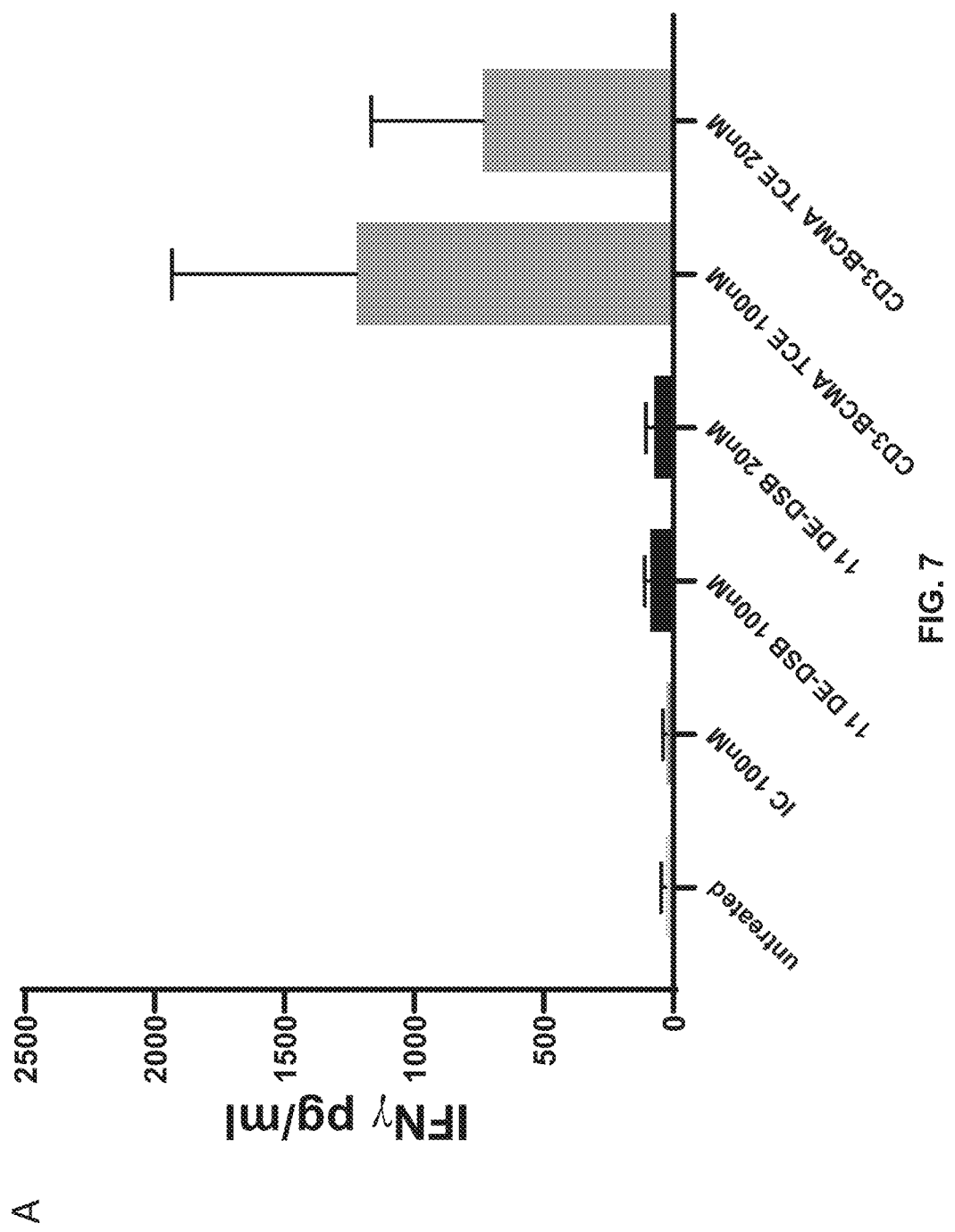
FIG. 7 is a set of histograms showing release of the cytokines IFNγ (Panel A), IL-6 (Panel B), and TNFα (Panel C) as induced by clone 11 in DE-DSB format in a PBMC setting in the presence of MM.1R MM cells. Isotype control IgG$_1$ DE-DSB (IC) was used as a negative control. A CD3-BCMA T cell engager ("TCE") was assessed as a comparator. Mean of four to five experiments is represented.
Figure 7:
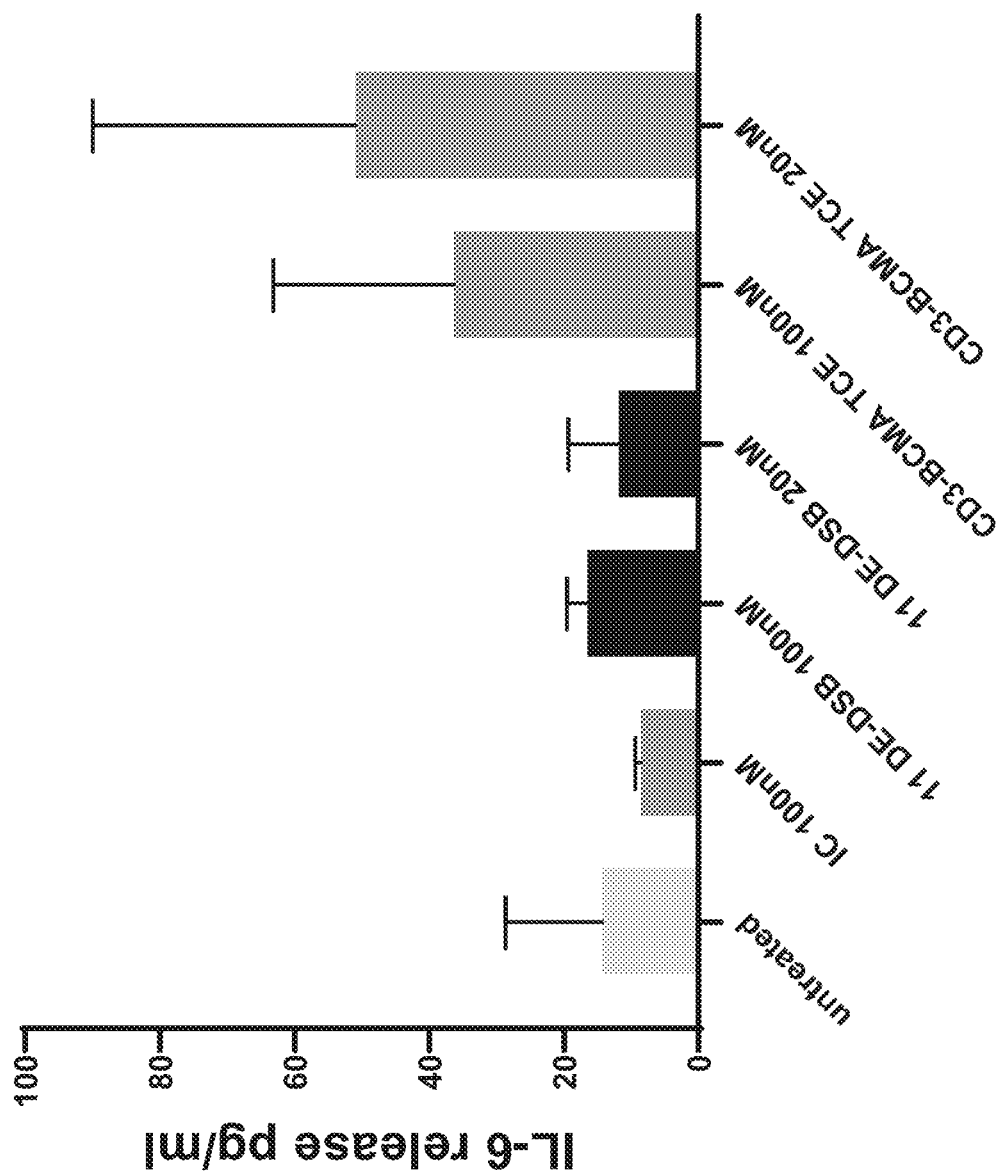
Figure 7:
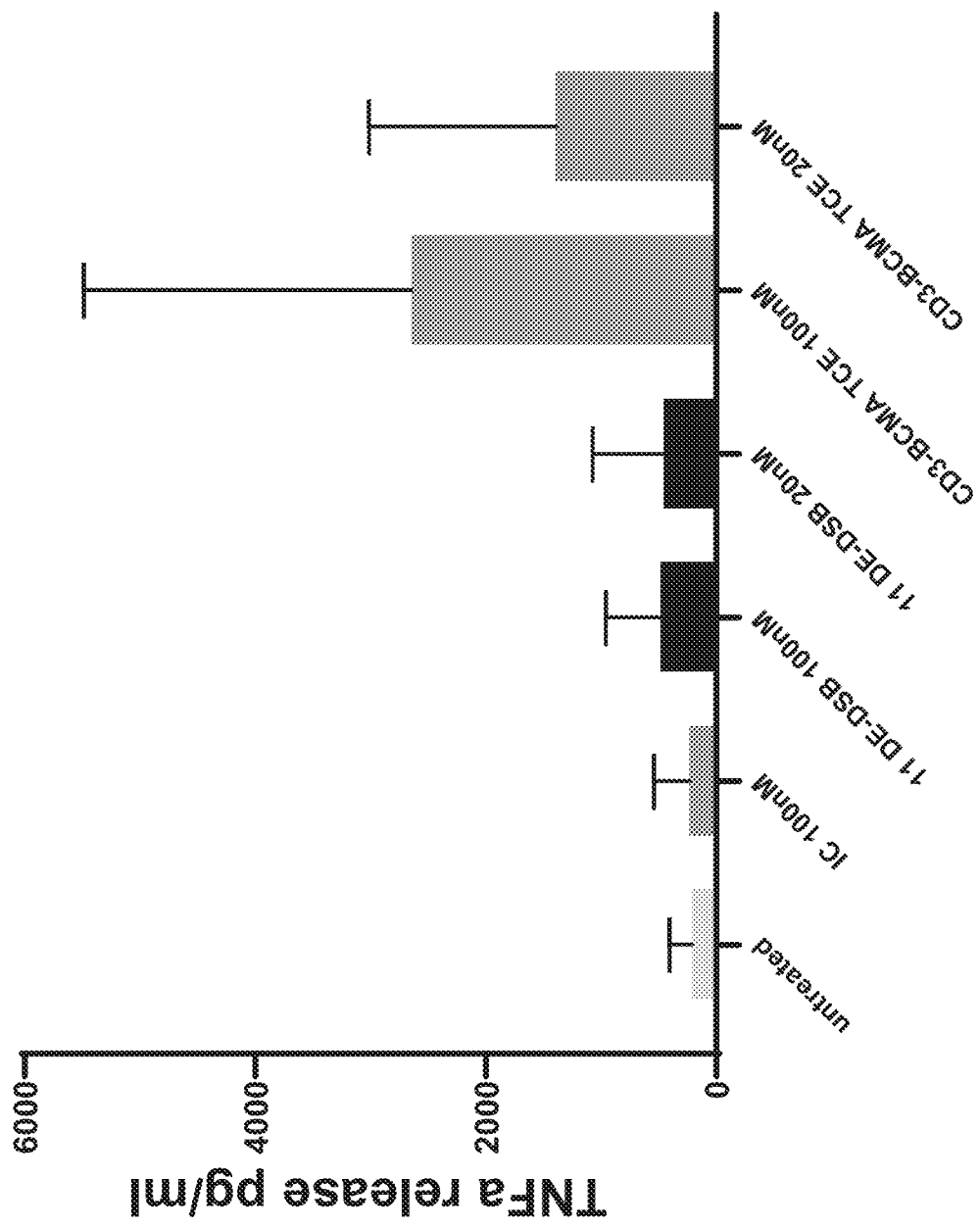

Clone 11 in DE-DSB and afucosylated formats induced minimal cytokine release in human PBMC in the presence of GPRC5D expressing MM.1R cells, with a fold increase from 1 to 3 compared to the baseline level of IFNγ, IL-6 and TNFα. This induction is much lower than the cytokine release induced by the anti-BCMA TCE (from 1.8 to 42 fold-change) (FIG. 7).

Example 8: In Vivo Activity of Anti-GPRC5D Antibodies Against MM.1R Multiple Myeloma Cells Implanted in NK Humanized hIL15tg-NOG Mice The in vivo efficacy of the anti-GPRC5D antibodies was evaluated in hIL15tg-NOG immunodeficient mice reconstituted with human NK cells and engrafted with disseminated human MM.1R cells. The hIL15tg-NOG mouse strain harboring the human IL15 gene has been used to allow a robust development of human NK cells in the mouse microenvironment. NK humanization of mice was performed by intravenous adoptive transfer of pre-amplified human NK (10 million) after sub-lethal irradiation (for more details on NK humanized murine models, see Rettman et al., *Cancer Res* (2022) 82 (12_Supplement): Abstract 4247, and Rettman et al., *Cancer Res* (2023) 83 (7_Supplement): Abstract 2940).

NK humanized mice were intravenously inoculated with tumor cells on Day 0. Treatments were administered intraperitoneally (IP) on Days 1, 4, and 7 post tumor implantation. The anti-GPRC5D antibodies BM1-afuco, 11-DE-DSB, and 11-afuco were administered at 10 mg/kg. The control group was treated with wildtype IgG$_1$ isotype control ("IC IgG wt") at 10 mg/kg.

Mice were checked and adverse clinical reactions noted. Individual mice were weighed daily until the end of the experiment (Day 110). Mice were euthanized when turning moribund according to predefined criteria in order to avoid animal suffering. Clinical signs related to the pathology and considered as critical were limb paralysis, ascites, palpable internal tumor mass, morbidity, and weight loss superior or equal to 20%.

The primary efficacy endpoints were the median survival time (MST) in days, the percent increased lifespan (% ILS), and the long-term survivor rate (in %).

Individual days of death (if any) of each mouse were reported. MST was determined for each group and the ratio ILS was calculated and expressed as percentage:

$$\% \text{ ILS} = 100 \times (T-C)/C$$

where T=MST of the treated group and C=MST of the control group.

A dose is considered as therapeutically active when % ILS is superior to 25%, and highly active when % ILS is superior to 50% (Johnson et al., *Br J Cancer* (2001) 84(10):1424-31).

Long term survivor rate is defined as the number of mice with survival duration superior or equal to two times the MST of the control group on the total number of mice in the group expressed in percentage.

The group treated by the IgG wildtype isotype control exhibited an MST of 53 days and no long-term survivors.

The BM1-afuco antibody induced statistically significant activity at a dose of 10 mg/kg in disseminated human MM cell line, MM.1R, implanted in NK humanized hIL15tg-NOG mice, with an ILS superior to 100% and 50% of long-term survivors compared to control.

The 11-afuco antibody induced statistically significant activity at a dose of 10 mg/kg in disseminated human MM cell line, MM.1R, implanted in NK humanized hIL15tg-NOG mice, with an ILS superior to 100% and 61% of long-term survivors compared to control.

The 11-DE-DSB antibody induced statistically significant activity at a dose of 10 mg/kg in disseminated human MM cell line, MM.1R, implanted in NK humanized hIL15tg-NOG mice, with an ILS superior to 100% and 72% of long-term survivors compared to control.

Figure 8:
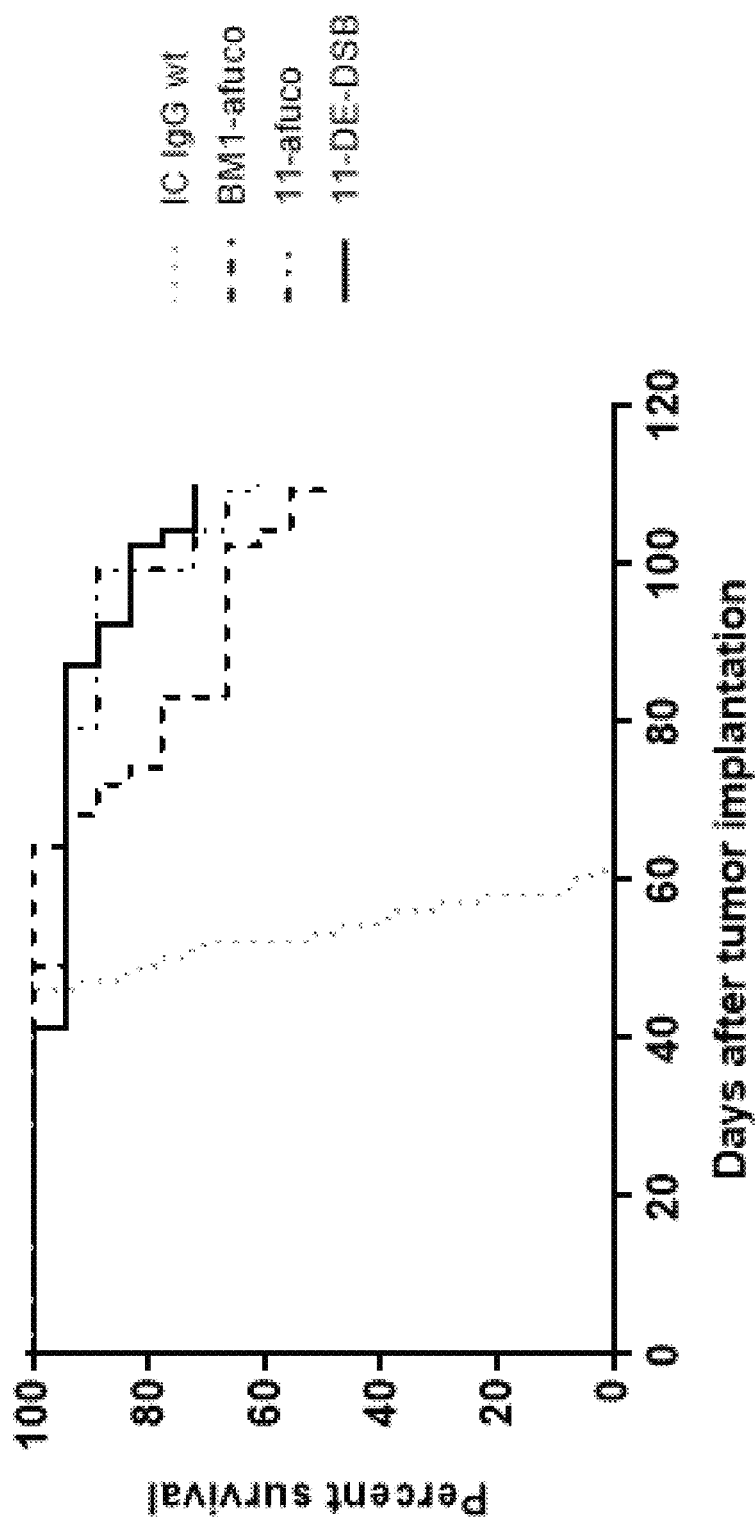
FIG. 8 is a Kaplan-Meier plot indicating survival rates of NK humanized hIL15tg-NOG mice implanted with disseminated human MM.1R cells, after treatment with clone 11 in afucosylated ("afuco") and DE-DSB formats as well as the Benchmark 1 antibody in afucosylated format (BM1-afuco). Isotype control IgG$_1$ wildtype (IC IgG wt) was used as a negative control

In conclusion, all tested anti-GPRC5D antibodies showed a robust activity at 10 mg/kg against disseminated human MM cell line, MM.1R, implanted in NK humanized hIL15tg-NOG mice (FIG. 8).

Table 8.1 presents data on the in vivo activity of the recited anti-GPRC5D antibodies against disseminated human MM cell line MM.1R implanted in NK humanized hIL15tg-NOG mice.

TABLE 8.1

In vivo activity of anti-GPRC5D antibodies against implanted MM.1R cells

| Group | Long term survivors (%) | MST (days) | ILS (%) | Biological comments |
| --- | --- | --- | --- | --- |
| IC IgG wt (Control group) | 0% | 53 | na | na |
| BM1-afuco | 50% | 109.5 | >100% | Highly active |
| 11-afuco | 61% | >110 | >100% | Highly active |
| 11-DE-DSB | 72% | >110 | >100% | Highly active |

MST: Median Survival Time in days;
ILS: Increased Lifespan in percent;
na: not applicable

Example 9: ADCC-Enhanced Fc Engineered GPRC5D NKCEs Demonstrate Favorable Elimination Half-Life This example evaluates the pharmacokinetic (PK) profile and parameters of clone 11 in DE-DSB (11-DE-DSB) and afucosylated (11-afuco) formats as natural killer cell engagers (NKCEs) after a single intravenous (2.5 mg/kg) administration to female huFcRn Tg32 transgenic mice.

Materials and Methods

The mice experiments were performed in transgenic Tg32 (B6. Cg-Fcgrttm, 1Dcr Tg (FCGRT)32Dcr/DcrJ) mice derived from C57BL/6 mice and purchased from the Jackson Laboratory (Bar Harbor, Maine). FcRn−/− hFcRn (line 32) Tg mice carry a null mutation for the mouse gene and a transgene expressing the hFcRn α-chain transgene under the control of its natural human promoter. Three Tg32 homozygous naïve adult female mice (mean body weight of 23.7 g) were used at study start.

For the dosing regimen, 11-DE-DSB and 11-afuco (1.5 mg/mL) were prepared respectively in 10 mM His, 150 mM NaCl, pH6 and DPBS buffer diluted in the same buffer extemporaneously and administered as single intravenous doses of 2.5 mg/kg into the tail vein with a dose volume of 10 mL/kg. Animals were evaluated using a serial sampling approach 0.083, 4, 24, 72, 168, 336, 504 and 672 hours across the study duration of 28 days. At each time point, blood samples (~20 µL—serial sampling) were withdrawn from the saphenous vein into K3-EDTA collecting devices. Immediately after collection, blood samples were placed on wet ice and then centrifuged. 4 µL of plasma was then diluted into 396 µL PBS/0.5% BSA (phosphate buffer saline/0.05% Tween20/0.5% bovine serum albumin).

For analysis, concentrations of 11-DE-DSB and 11-afuco were determined in plasma using an exploratory LBA (Ligand Binding Assay) method. Both compounds were captured by donkey anti-huIgGFc biotinylated bound on the streptavidin-wells of an MSD plate. Detection was carried out using goat anti-hu IgG-sulfo tag before reading by chemiluminescence. The Lower Limit of Quantification (LLOQ) value was 0.2 µg/mL.

Statistical Analysis

Individual plasma concentration values of 11-DE-DSB and 11-afuco NKCEs (expressed in µg/mL) were summarized by descriptive statistics (mean, standard deviation (SD) and coefficient of variation (CV %)) and tabulated by sampling time. All results were reported with three significant figures, except CV % with no decimal place.

Individual PK parameters were summarized by descriptive statistics as described above. Individual and mean values were expressed with three significant figures (except $t_{max}$ and $t_{last}$ rounded appropriately to the time value, with only the median and the range [min-max]values reported).

Results

No clinical signs or symptoms were observed during the study.

Mean and individual values (N=3) of plasma concentrations (µg/mL) of 11-DE-DSB NKCEs obtained after a single IV (2.5 mg/kg) administration to female huFcRn Tg32 mice are reported below in Table 9.1.

TABLE 9.1

Plasma concentrations of 11-DE-DSB in huFcRn Tg32 mice

| Animal ID | Time (day) | | | | | | | | |
|---|---|---|---|---|---|---|---|---|---|
| | 0.0035 | 0.17 | 1 | 3 | 7 | 10 | 14 | 21 | 28 |
| | Concentrations (µg/mL) | | | | | | | | |
| F7 | 62.1 | 29.3 | 21.5 | 16.3 | 12.0 | 7.98 | BLQ* | BLQ* | BLQ* |
| F8 | 59.5 | 31.6 | 18.4 | 15.6 | 10.6 | 9.69 | 5.88 | 0.550* | BLQ* |
| F9 | 60.1 | 27.6 | 19.1 | 17.3 | 10.5 | 6.31 | 4.57 | 2.86 | 2.26 |
| Mean | 60.6 | 29.5 | 19.7 | 16.4 | 11.0 | 7.99 | 5.23 | 2.86 | 2.26 |
| SD | 1.36 | 2.01 | 1.63 | 0.854 | 0.839 | 1.69 | NA | NA | NA |
| CV % | 2 | 7 | 8 | 5 | 8 | 21 | NA | NA | NA |

*aberrant values rejected from descriptive statistics and PK analyses

Mean and individual values (N=3) for pharmacokinetic parameters of 11-DE-DSB in plasma after a single intravenous (2.5 mg/kg) administration are presented below in Table 9.2.

TABLE 9.2

Pharmacokinetic parameters of 11-DE-DSB in female huFcRn Tg32 mice

| Animal ID | $C_0$ (µg/mL) | $AUC_{last}$ (day * µg/mL) | $t_{last}$ (day) | AUC (day * µg/mL) | $AUC_{extr\,ap}$ (%) | CL (mL/day/kg) | $V_{SS}$ (mL/kg) | $t_{1/2z}$ (day) |
|---|---|---|---|---|---|---|---|---|
| F7 | 63.1 | 153 | 10 | 229 | 33.2 | NC | NC | NC |
| F8 | 60.3 | 176 | 14 | 246 | 28.3 | NC | NC | NC |
| F9 | 61.1 | 210 | 28 | 249 | 15.8 | 10.0 | 139 | 12.1 |
| Mean | 61.5 | 180 | 14 | 242 | NA | 10.0 | 139 | 12.1 |
| SD | 1.44 | 28.4 | [10-28] | 10.6 | NA | NA | NA | NA |
| CV % | 2 | 16 | — | 4 | NA | NA | NA | NA |

After 2.5 mg/kg intravenous administration, 11-DE-DSB NKCE concentrations were quantifiable in plasma up to 28 days (last sampling time). Plasma clearance was estimated to 10.0 mL/day/kg and volume of distribution at steady state was 139 mL/kg leading to a terminal elimination half-life ($t_{1/2}$) around 12 days.

Mean and individual values (N=3) of plasma concentrations (µg/mL) of 11-afuco NKCEs obtained after a single IV (2.5 mg/kg) administration to female huFcRn Tg32 mice are reported below in Table 9.3.

TABLE 9.3

Plasma concentrations of 11-afuco in huFcRn Tg32 mice

| Animal ID | Time (day) | | | | | | | | |
|---|---|---|---|---|---|---|---|---|---|
| | 0.0035 | 0.17 | 1 | 3 | 7 | 10 | 14 | 21 | 28 |
| | | | | Concentrations (μg/mL) | | | | | |
| F1 | 118 | 51.7 | 11.9* | 25.4 | 22.2 | 19.1 | 14.2 | 9.69 | 8.58 |
| F2 | 87.4 | 45.3 | 30.9 | 32.6 | 21.8 | 19.7 | 18.0 | 8.88 | 4.07 |
| F3 | 94.6 | 41.5 | 33.8 | 28.6 | 20.9 | 19.4 | 19.7 | 9.21 | 4.13 |
| Mean | 100 | 46.2 | 32.4 | 28.9 | 21.6 | 19.4 | 17.3 | 9.26 | 5.59 |
| SD | 16.0 | 5.15 | NA | 3.61 | 0.666 | 0.300 | 2.82 | 0.407 | 2.59 |
| CV % | 16 | 11 | NA | 12 | 3 | 2 | 16 | 4 | 46 |

Mean and individual values (N=3) for pharmacokinetic parameters of 11-afuco NKCEs in plasma after a single intravenous (2.5 mg/kg) administration are presented below in Table 9.4.

TABLE 9.4

Pharmacokinetic parameters of 11-afuco in female huFcRn Tg32 mice.

| Animal ID | $C_0$ (μg/mL) | $AUC_{last}$ (day * μg/mL) | $t_{last}$ (day) | AUC (day * μg/mL) | $AUC_{extr\ ap}$ (%) | CL (mL/day/kg) | $V_{SS}$ (mL/kg) | $t_{1/2z}$ (day) |
|---|---|---|---|---|---|---|---|---|
| F1 | 120 | 495 | 28 | 676 | 26.8 | 3.70 | 75.2 | 14.7 |
| F2 | 88.6 | 492 | 28 | 542 | 9.21 | 4.61 | 56.7 | 8.50 |
| F3 | 96.3 | 491 | 28 | 543 | 9.60 | 4.61 | 58.5 | 8.74 |
| Mean | 102 | 493 | 28 | 587 | NA | 4.3 | 63.5 | 10.6 |
| SD | 16.4 | 2.1 | [28-28] | 77.3 | NA | 0.526 | 10.2 | 3.49 |
| CV% | 16 | 0 | — | 13 | NA | 12 | 16 | 33 |

After 2.5 mg/kg intravenous administration, 11-afuco NKCE concentrations were quantifiable in plasma up to 28 days (last sampling time). Plasma clearance was estimated to 4.30±0.525 mL/day/kg and volume of distribution at steady state was 63.5±10.2 mL/kg leading to a terminal elimination half-life ($t_{1/2}$) around 11 days.

Example 10: Combined Exploratory Pharmacokinetic (PK) and Safety Study Following Single Intravenous Infusion or Subcutaneous Administration of 11-DE-DSB NKCEs in Cynomolgus Monkeys The objective of this exploratory (non-GLP) study was to determine the pharmacokinetics (PK) and tolerability/toxicity profile of 11-DE-DSB when administered to cynomolgus monkeys as 1) a single dose by 30-min intravenous (IV) infusion, and 2) a single dose by a subcutaneous (SC) injection, followed by a four-week observation period.

A total of eight female cynomolgus monkeys (*Macaca fascicularis*, ~31 to 33 months of age at the initiation of the dosing) were included in the study. The study design is described in Table 10.1 below.

TABLE 10.1

Dosing regimen for PK and tolerability/toxicity profile study in cynomolgus monkeys

| Group | Test Item | Dosing Regimen | Dose Level (mg/kg) | Concentration (mg/mL) | Volume (mL/kg) | Animal ID No. Female |
|---|---|---|---|---|---|---|
| 1 | Control article [a] | 30-min IV infusion | 0 | 0 | 2.5 | 1-2 |
| 2 | 11-DE-DSB [b] | 30-min IV infusion | 5 | 2 | 2.5 | 3-4 |
| 3 | 11-DE-DSB [b] | 30-min IV infusion | 25 | 10 | 2.5 | 5-6 |
| 4 | 11-DE-DSB [b] | SC bolus | 25 | 10 | 2.5 | 7-8 |

Abbreviations:
IV: intravenous;
SC: subcutaneous
[a] Control group: animals received 10 mM Histidine pH 6, 150 mM NaCl.
[b] A stock solution of 11-DE-DSB was provided at a concentration of 10.75 mg/mL in 10 mM histidine buffer pH6, 150 mM NaCl.

Animals were dosed on the basis of the most recent body weight.

The intravenous infusion was performed on the saphenous vein using an intravenous catheter, the subcutaneous injection on the back of the animal (interscapular area in one injection point). The intravenous infusion was performed using a calibrated syringe pump. After administration, injection sites were carefully observed, and a local compression was performed during a time sufficient to prevent bleeding.

The evaluated parameters included mortality, clinical signs, body weight, food consumption, body temperature, examination of injection sites, hematology, coagulation, and clinical chemistry (including CRP). Blood was also collected for PK evaluation and plasma cytokine levels. At the end of the four-week observation period, all monkeys were returned to the animal colony.

PK Evaluation

Figure 9:
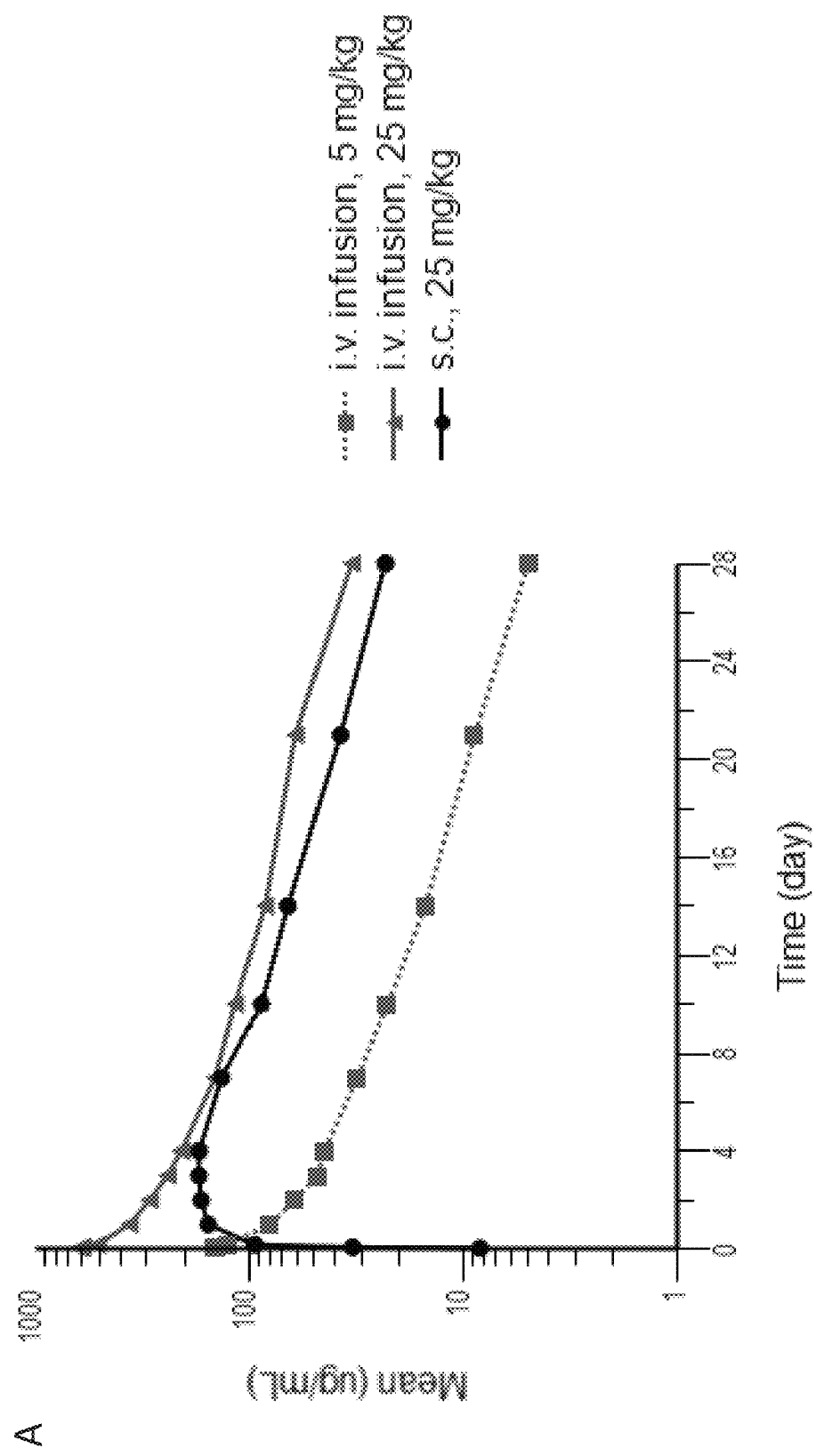
FIG. 9 is a pair of line graphs showing mean (Panel A) and individual (Panel B) pharmacokinetic (PK) profiles after a single 30-minute intravenous infusion at 5 mg/kg or 25 mg/kg, or subcutaneous administration at 25 mg/kg, of clone 11 in DE-DSB format to female cynomolgus monkeys.
Figure 9:
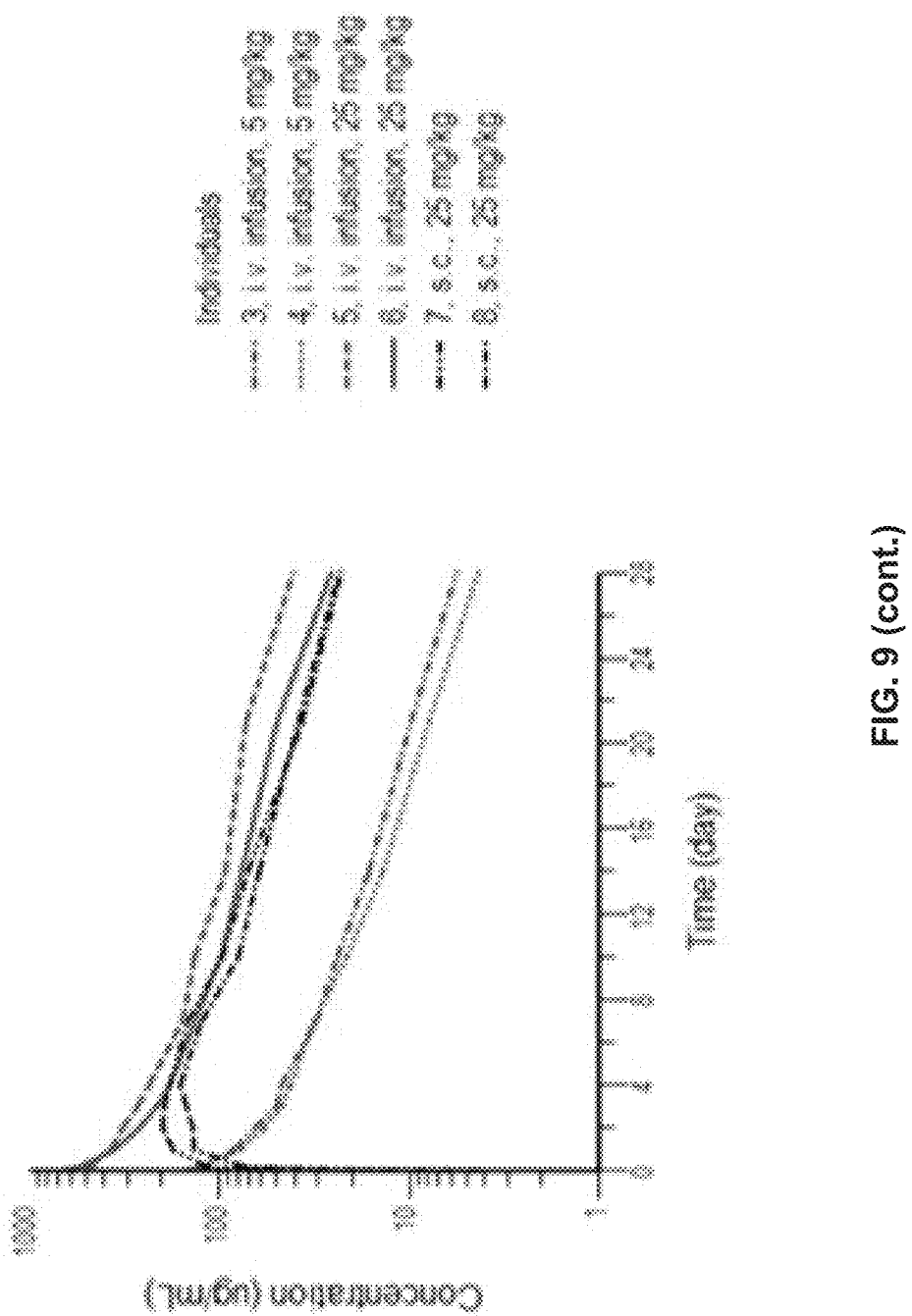

Blood samples (0.4 mL in a K2-EDTA sampling tube) were collected from the femoral, saphenous and/or cephalic vein (the vein used for infusion was not used for blood collection purposes), according to the following scheduled days and sampling timepoints:

eters (dose proportionality and bioavailability). Mean was calculated on plasma concentrations for each sampling timepoint and for PK parameters (FIG. 9).

Table 10.2 presents data on individual and mean (n=2) PK parameters in plasma observed after 30-minute intravenous infusion or subcutaneous administration of 11-DE-DSB to female cynomolgus monkeys.

TABLE 10.2

| Route | Dose (mg/kg) | ID | $C_{max}$ (μg/mL) | $t_{max}$ (day) | $AUC_{last}$ (day * μg/mL) | $t_{last}$ (day) | AUC (day * μg/mL) | CL (mL/day/kg) | $V_{SS}$ (mL/kg) | $t_{1/2z}$ (day) |
|---|---|---|---|---|---|---|---|---|---|---|
| 30-min IV infusion | 5 | 3 | 146 | 0.02 | 714 | 28 | 784 | 6.38 | 67.7 | 8.62 |
| | | 4 | 147 | 0.06 | 652 | 28 | 700 | 7.15 | 67.1 | 7.52 |
| | | Mean | 147 | 0.04 | 683 | 28 | 742 | 6.76 | 67.4 | 8.07 |
| 30-min IV infusion | 25 | 5 | 584 | 0.02 | 3790 | 28 | 4450 | 5.62 | 79.1 | 11.2 |
| | | 6 | 658 | 0.02 | 3100 | 28 | 3440 | 7.27 | 82.7 | 9.25 |
| | | Mean | 621 | 0.02 | 3440 | 28 | 3940 | 6.44 | 80.9 | 10.2 |
| SC | 25 | 7 | 199 | 2 | 2480 | 28 | 2760 | NC | NC | 8.49 |
| | | 8 | 161 | 4 | 2110 | 28 | 2460 | NC | NC | 10.2 |
| | | Mean | 180 | 3 | 2300 | 28 | 2610 | NA | NA | 9.37 |

Abbreviations:
AUC: Area under the concentration versus time curve calculated using the trapezoidal method from time 0 to infinity;
$AUC_{last}$: Area under the concentration versus time curve calculated using the trapezoidal method from time 0 to the real time $t_{last}$;
CL: Total body clearance after a single intravenous administration of a drug from the matrix;
ID: animal ID;
inf.: Infusion;
NC: not calculable;
NA: not applicable;
$C_{max}$: Maximum observed concentration;
t1/2z: Apparent terminal half-life;
$t_{last}$: Time of last measurable concentration;
$t_{max}$: Time of maximum observed concentration;
$V_{SS}$: Volume of distribution at the steady state after single intravenous dose.

| Group | Scheduled days | Timepoints |
|---|---|---|
| 1, 2, and 3 (IV groups) | Day 1 | 0.5 (end of infusion), 1.5, 4, 24, 48, 72, 96, 168, 240, 336, 504, and 672 hours after the start of the infusion (i.e., 0.021, 0.063, 0.17, 1, 2, 3, 4, 7, 10, 14, 21 and 28 days) |
| 4 (SC group) | Day 1 | 0.5, 1.5, 4, 24, 48, 72, 96, 168, 240, 336, 504, and 672 hours after the injection (i.e., 0.021, 0.063, 0.17, 1, 2, 3, 4, 7, 10, 14, 21 and 28 days) |

Blood samples from control animals (Group 1) were discarded just after sampling.

After collection, each blood sample was centrifuged at approximately 4° C. at 1500 g, for 10 min. The plasma samples obtained (at least 150 μL) were transferred into labeled polypropylene tubes and frozen at approximately −80° C. until analysis.

An exploratory immunoassay method was used for the quantification of 11-DE-DSB in cynomolgus monkey plasma samples. The method consists of a stepwise sandwich format. The capture was made using biotinylated goat anti-human IgG Monkey Ads immobilized on the streptavidin bead columns within Gyrolab Bioaffy discs (CD200) containing microstructures. The detection was made using goat anti-human IgG Monkey Ads AlexaFluor® 647. The on-column fluorescence measurement was performed within the Gyrolab platform. The range of quantification was from 200 ng/mL (lower limit of quantification, LLOQ) up to 500 000 ng/mL (upper limit of quantification, ULOQ) using a minimum required dilution (MRD) of 1/100.

WinNonLin software (Phoenix 64 v8.2 Pharsight, Certara Inc.) was used for PK evaluation of the determined plasma concentrations of 11-DE-DSB and for additional PK param- Regardless of the dose and the route of administration, 11-DE-DSB was quantifiable up to the last sampling time (Day 28).

After IV administration, mean clearance was around 6.6 mL/day/kg and mean volume of distribution around 74 mL/kg, leading to a terminal elimination half-life of around 9 days.

After 30-minute intravenous infusion at 5 and 25 mg/kg, exposure increased in proportion with the dose increase.

After subcutaneous administration at 25 mg/kg, bioavailability was around 65%.

Evaluation of Cytokines

Blood samples (0.5 mL in a K2-EDTA sampling tube) were collected from the femoral, saphenous and/or cephalic vein (the vein used for infusion was not used for blood collection purposes) on Day 1, before treatment, 4, 24, and 48 hours after the start of dosing.

The assessment of IFNγ, IL-6, IL-8 and TNFα in monkey plasma samples was performed using an exploratory ECLIA (ElectroChemiluminescent ImmunoAssay) method from Mesoscale Discovery (U-PLEX Proinflam Combo 1 (NHP) SECTOR assay kit, cat. no. K15070K-2).

All variations were expressed as compared to baseline values (i.e., before treatment values). Due to the analytical variability, cytokine increases were considered potentially compound-related when values were more than 2-fold higher than the corresponding pretest value and higher than the highest value observed in the control group. The grading was applied as followed: 3 to 10-fold changes: very minimal increase; 11 to 100-fold changes: minimal increase; 101 to 1000-fold changes: moderate increase; and, ≥1001-fold changes: marked increase.

Table 10.3 presents data on individual plasma cytokine levels (pg/mL) and fold change versus baseline after 30-minute intravenous infusion or subcutaneous administration of 11-DE-DSB to female cynomolgus monkeys.

TABLE 10.3

| Route | Dose (mg/kg) | ID | TP | IFNγ pg/mL | FC | IL-6 pg/mL | FC | IL-8 pg/mL | FC | TNFα pg/mL | FC |
|---|---|---|---|---|---|---|---|---|---|---|---|
| 30-min IV infusion | 0 | 1 | Day 1 - BT | 7.18 | 1 | 0.51 | 1 | 0.58 | 1 | 0.82 | 1 |
| | | | Day 1 - 4 hours | 7.18 | 1 | 0.51 | 1 | 0.58 | 1 | 0.82 | 1 |
| | | | Day 1 - 24 hours | 7.18 | 1 | 0.51 | 1 | 0.58 | 1 | 0.82 | 1 |
| | | | Day 1 - 48 hours | 7.18 | 1 | 0.51 | 1 | 0.58 | 1 | 0.82 | 1 |
| | | 2 | Day 1 - BT | 7.18 | 1 | 4.63 | 1 | 0.58 | 1 | 0.82 | 1 |
| | | | Day 1 - 4 hours | —[a] | — | —[a] | — | —[a] | — | —[a] | — |
| | | | Day 1 - 24 hours | 7.18 | 1 | 3.83 | 1 | 0.58 | 1 | 0.82 | 1 |
| | | | Day 1 - 48 hours | 7.18 | 1 | 5.86 | 1 | 0.58 | 1 | 0.82 | 1 |
| 30-min IV infusion | 5 | 3 | Day 1 - BT | 7.18 | 1 | 0.51 | 1 | 0.58 | 1 | 0.82 | 1 |
| | | | Day 1 - 4 hours | 7.18 | 1 | 1.49 | 3 | 0.58 | 1 | 0.82 | 1 |
| | | | Day 1 - 24 hours | 7.18 | 1 | 1.06 | 2 | 0.58 | 1 | 0.82 | 1 |
| | | | Day 1 - 48 hours | 7.18 | 1 | 0.85 | 2 | 0.58 | 1 | 0.82 | 1 |
| | | 4 | Day 1 - BT | 7.18 | 1 | 0.74 | 1 | 0.98 | 1 | 0.82 | 1 |
| | | | Day 1 - 4 hours | 7.18 | 1 | 2.04 | 3 | 0.58 | 1 | 0.82 | 1 |
| | | | Day 1 - 24 hours | 7.18 | 1 | 0.51 | 1 | 0.58 | 1 | 0.82 | 1 |
| | | | Day 1 - 48 hours | 7.18 | 1 | 0.55 | 1 | 2.49 | 3 | 0.82 | 1 |
| 30-min IV infusion | 25 | 5 | Day 1 - BT | 7.18 | 1 | 0.51 | 1 | 0.58 | 1 | 0.82 | 1 |
| | | | Day 1 - 4 hours | 7.18 | 1 | 1.28 | 3 | 0.58 | 1 | 0.82 | 1 |
| | | | Day 1 - 24 hours | 7.18 | 1 | 1.29 | 3 | 0.58 | 1 | 0.82 | 1 |
| | | | Day 1 - 48 hours | 7.18 | 1 | 1.31 | 3 | 0.58 | 1 | 0.82 | 1 |
| | | 6 | Day 1 - BT | 7.18 | 1 | 15.11 | 1 | 0.58 | 1 | 0.82 | 1 |
| | | | Day 1 - 4 hours | 7.18 | 1 | 12.81 | 1 | 0.58 | 1 | 0.82 | 1 |
| | | | Day 1 - 24 hours | 7.18 | 1 | 5.19 | 0 | 0.58 | 1 | 0.82 | 1 |
| | | | Day 1 - 48 hours | 7.18 | 1 | 2.97 | 0 | 0.58 | 1 | 0.82 | 1 |
| SC | 25 | 7 | Day 1 - BT | 7.18 | 1 | 0.51 | 1 | 0.58 | 1 | 0.82 | 1 |
| | | | Day 1 - 4 hours | 7.18 | 1 | 11.91 | 23 | 0.58 | 1 | 0.82 | 1 |
| | | | Day 1 - 24 hours | 7.18 | 1 | 2.56 | 5 | 0.58 | 1 | 0.82 | 1 |
| | | | Day 1 - 48 hours | 7.18 | 1 | 1.79 | 4 | 0.58 | 1 | 0.82 | 1 |
| | | 8 | Day 1 - BT | 7.18 | 1 | 0.51 | 1 | 0.58 | 1 | 0.82 | 1 |
| | | | Day 1 - 4 hours | 7.18 | 1 | 17.24 | 34 | 0.58 | 1 | 0.82 | 1 |
| | | | Day 1 - 24 hours | 7.18 | 1 | 7.10 | 14 | 0.58 | 1 | 0.82 | 1 |

TABLE 10.3-continued

| Route | Dose (mg/kg) | ID | TP | IFNγ pg/mL | FC | IL-6 pg/mL | FC | IL-8 pg/mL | FC | TNFα pg/mL | FC |
|---|---|---|---|---|---|---|---|---|---|---|---|
| | | | Day 1 - 48 hours | 7.18 | 1 | 1.30 | 3 | 0.58 | 1 | 0.82 | 1 |

Abbreviations:
BT: before treatment;
FC: fold change;
ID: animal ID;
IV: intravenous;
SC: subcutaneous;
TP: timepoint;
—: no data.
[a] No result reported due to insufficient plasma volume for cytokine analysis.
Values below LLOQ replaced with the corresponding LLOQ values:
IFN-γ: 7.18 pg/mL,
IL 6: 0.51 pg/mL,
IL 8: 0.58 pg/mL, and
TNF-α: 0.82 pg/mL.

No noteworthy cytokine elevation was observed following a single IV dose of 11-DE-DSB up to 25 mg/kg or a single SC dose of 11-DE-DSB at 25 mg/kg. Only transient very minimal to minimal IL-6 increase was observed four hours after 11-DE-DSB administration and returning close to baseline within approximately 24 hours after 11-DE-DSB administration. No 11-DE-DSB-related changes in IFN-γ, IL-8 and TNFα levels were observed in any animals at any dose during the study.

The administration of 11-DE-DSB to female cynomolgus monkeys at 5 or 25 mg/kg by 30-min IV infusion and at 25 mg/kg by SC route was clinically well tolerated. No 11-DE-DSB-related clinical signs, including any related to nails and tongue observation, body temperature, body weight and clinical observation of the animals, were reported. Good local and general tolerance were reported. There were no changes in hematology and clinical chemistry that were considered as 11-DE-DSB-related.

Therefore, under these study conditions, the highest doses tested of 25 mg/kg of 11-DE-DSB as a single 30-minute IV infusion ($C_{max}$ and AUC corresponding values of 621 µg/mL and 3 940 day*µg/mL for 11-DE-DSB) and as a single SC injection ($C_{max}$ and AUC corresponding values of 180 µg/mL and 2 610 day*µg/mL for 11-DE-DSB) were well tolerated and did not induce any adverse effects.

Example 11: Anti-GPRC5D Antibodies Ex Vivo Activity and Mediated NK Cell Activation in Primary NDMM Patient Samples Bone marrow (BM) and peripheral blood samples containing multiple myeloma cells and autologous immune effector cells were obtained from untreated newly diagnosed patients with multiple myeloma (MM) to assess the cumulative impact of an anti-GPRC5D-antibody ex vivo. The tumoral plasma cells (PC) number and NK cell number were determined for each samples by flow cytometry as defined as $SS^{low}/FS^{high}/CD45^{low}/CD138^+/CD38^+/CD56^{+/-}$ for plasma cells and $CD45^+/CD3^-/CD56^+/CD16^{+/-}$. The Effector:Target (E:T) ratio was calculated as NK concentration/PC concentration. Receptor density of GPRC5D on tumoral plasma cells from BM was determined using a mouse anti-human GPRC5D clone 571932 (R&DSystem) and a murine Ig calibrator kit (Biocytex) following provider's recommendations. Remained BM sample's volume was divided to perform killing assays and NK cell activation and degranulation assays.

BM samples containing tumoral plasma cells (PC) and autologous effector NK cells were incubated with negative isotype control isotype (anti-TNP-DE-DSB) or anti-GPRC5D ADCC-enhanced 11-DE-DSB at 0.01 and 1 µg/ml. At the end of the overnight incubation, cells were stained with the panels of antibodies as shown in Table 11.1 to determine 1) the remaining viable plasma cells, 2) the NK cell activation, and 3) the CD107a NK cell degranulation.

Table 11.1 shows the panel of antibodies used for anti-GPRC5D antibodies ex vivo activity and mediated NK cell activation in primary NDMM patient samples.

TABLE 11.1

| Determination of NK/PC ratio at Day 0 | Determination of PC killing | NK cells activation assay | CD107a NK cells degranulation |
|---|---|---|---|
| CD45 PB | CD45 PB450 | eFluor780 (Viability marker) | CD107a PE |
| CD138 APC | CD138 APC | CD138 APC Fire750 | eFluor 780 (Viability marker) |
| CD38 FITC | CD38 FITC | CD3 APC Fire750 | CD45 BV510 |
| CD56 APC AF750 | CD56 APC AF750 | CD45 BV510 | CD3 PerCP |
| CD3 PE | CD3 PE | CD56 BV421 | CD56 BV421 |
| CD16 BV510 | CD19 BV510 | CD16 FITC | CD16 FITC |
| CD107a | PI (Viability marker) Counting beads PE | CD69 PE Cy5.5 | |

Flow cytometric data were analyzed with FlowJo software. Myeloma cell death was assessed by disappearance of $CD45^{low}/CD138^+/CD38^+/CD56^{+/-}$ cells. Lysis % was calculated relative to isotype negative control, normalized to B cell numbers (stable number along the experiment). NK cell degranulation marker on NK cells was assessed by CD107a expression on $CD3^-/CD56^+$ NK cells.

Figure 10:
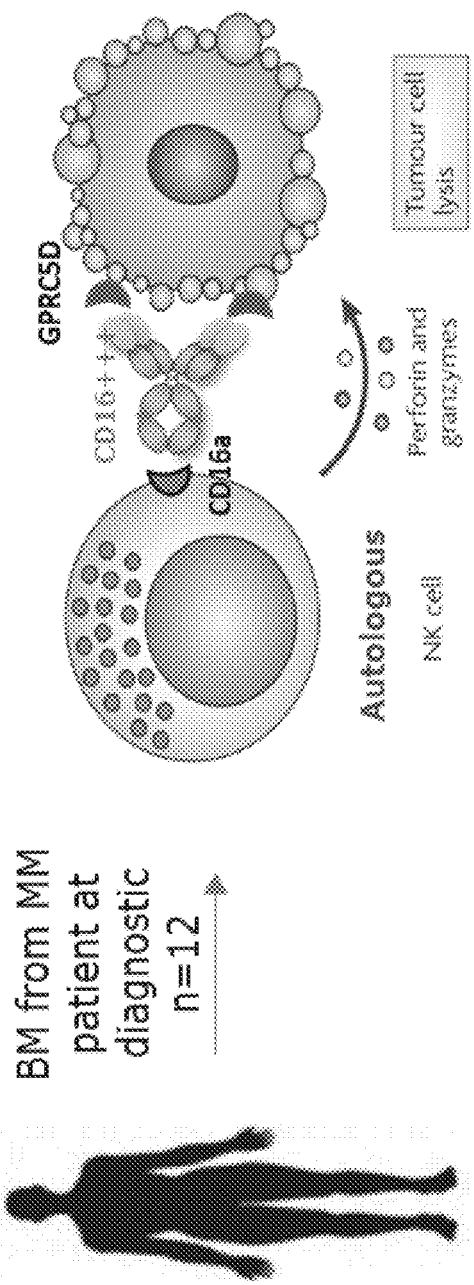
FIG. 10 schematically shows the principle of the ex vivo study on primary newly diagnosed multiple myeloma (NDMM) patient samples of Example 11.

FIG. 10 schematically shows the principle of this ex vivo study. Table 11.2 presents the results of a flow cytometric analysis of bone marrow (BM) cells from NDMM patients showing GPRC5D receptor density (sABC: specific Antigen Binding Capacity) on tumoral plasma cells (PC), NK:PC Effector:Target (E:T) ratio, and PC lysis after ex vivo overnight treatment with 11-DE-DSB.

TABLE 11.2

| BM MM sample ID | GPRC5D sABC | E:T ratio | PC lysis % |
|---|---|---|---|
| #001 | 1184 | 14.3 | 43.4 |
| #002 | 626 | 1.7 | 8.9 |

TABLE 11.2-continued

| BM MM sample ID | GPRC5D sABC | E:T ratio | PC lysis % |
|---|---|---|---|
| #003 | 6242 | 0.1 | 0 |
| #004 | 814 | 27.7 | 27.5 |
| #005 | 2888 | 0.2 | 39.9 |
| #006 | 408 | 0.6 | 5.6 |
| #007 | 3144 | 1.3 | 53.4 |
| #008 | 903 | 2.8 | 47.6 |
| #009 | 156 | 5.0 | 10.9 |
| #010 | 3475 | 5.8 | 58.9 |
| #011 | 491 | 0.2 | 35.2 |
| #012 | 293 | 2.1 | 2.1 |

Figure 11:
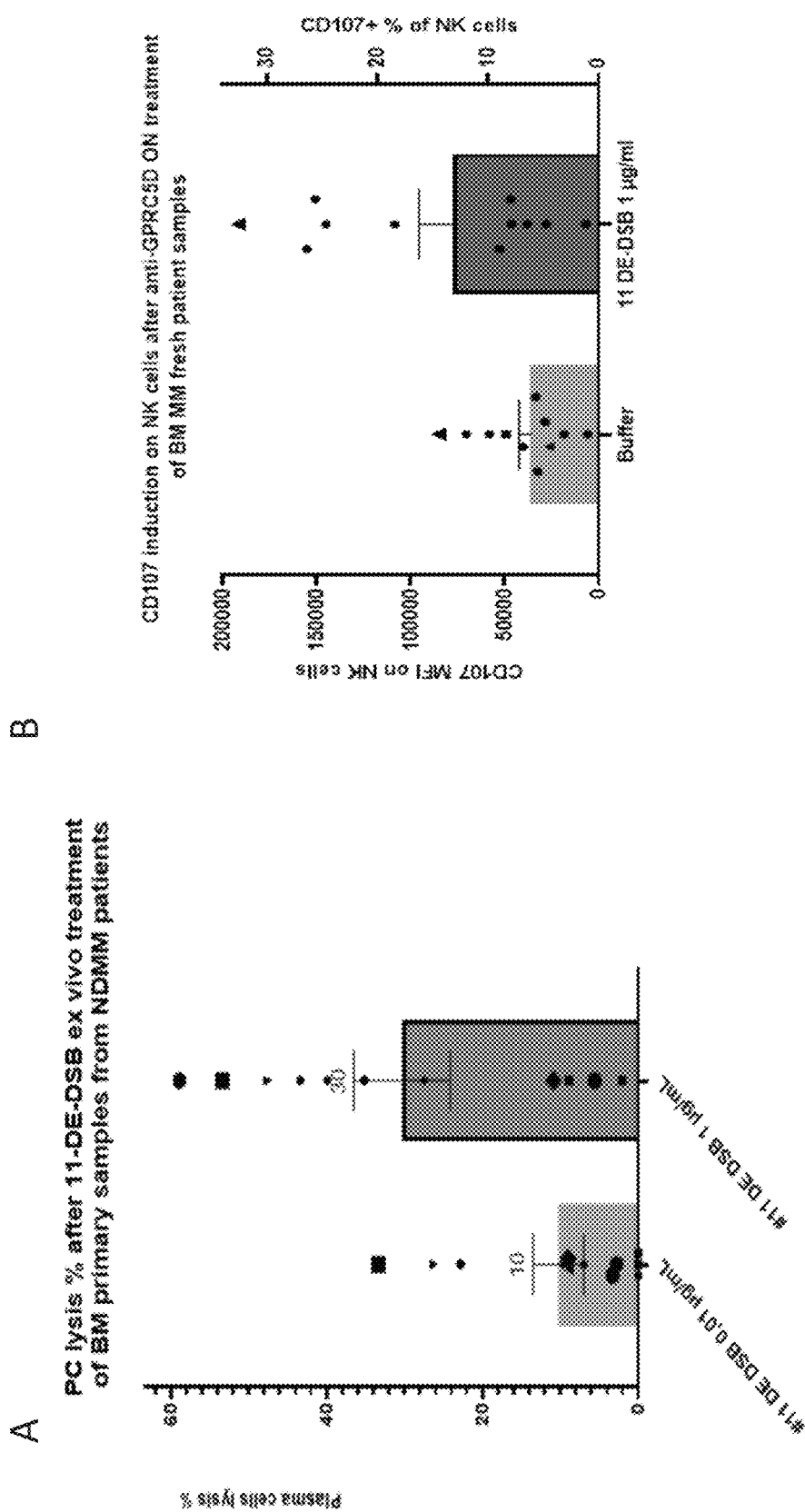
FIG. 11 is a pair of graphs showing plasma cell lysis after 11-DE-DSB ex vivo treatment of bone marrow primary samples from NDMM patients (Panel A) and induction of CD107 on NK cells after anti-GPRC5D overnight treatment of BM MM fresh patient samples (Panel B).

FIG. 11, Panel A graphically shows the results of plasma cell (PC) lysis. FIG. 11, Panel B graphically shows CD107 induction on NK cells after anti-GPRC5D overnight treatment of bone marrow (BM) patient samples.

Flow cytometry analysis of BM MM patient showed a wild range of GPRC5D receptor density and E:T ratio. Analysis of BM MM patient which were treated with anti-GPRC5D ADCC-enhanced 11-DE-DSB antibody showed a lysis of myeloma cells and an increase in activated NK cells as assessed by CD107a expression on CD3$^-$/CD56$^+$ NK cells. These data demonstrate that anti-GPRC5D ADCC-enhanced 11-DE-DSB antibody activates ex vivo NK cells in primary samples from MM patients in an autologous assay with multiple myeloma cells as well as NK cells from the same patient.

Example 12: Competition for Binding to GPRC5D with Benchmark Molecules

The interaction of the antibodies with human GPRC5D on cells was studied by FACS when in competition with benchmark molecules, under the following conditions:
  Benchmark antibodies (human IgG1 format) were labelled with biotin. It was checked that the labelling did not impair binding properties.
  Labelled benchmark antibodies were added to GPRC5D cells at EC80 concentration in the presence of increasing doses of the test antibody (human afucosylated IgG1 format).
  Binding of the benchmark antibodies was measured and level of competition was determined.

TABLE 12.1

Competition level between clone 11 and benchmark antibodies for binding to GPRC5D cells

| | Competition level | | |
|---|---|---|---|
| | BM2-IgG$_1$ wt biotinylated | BM3-IgG$_1$ wt biotinylated | BM4-IgG$_1$ wt biotinylated |
| 11-afuco | full | partial | partial |
| BM1-IgG$_1$ wt | partial | partial | partial |
| BM2-IgG$_1$ wt | full | partial | partial |
| IC | no | no | no |

Example 13: ADCP Macrophages Mediated Phagocytosis Activity Against MM.1R MM Cell Line Antibody dependent cell-mediated phagocytosis (ADCP) activity of the 11-DE-DSB antibody was assessed using MM.1R cells (ATCC ref. CRL-2975) and macrophages derived from monocytes purified from human peripheral blood mononuclear cells (PBMC) isolated from buffy coat of 5 different healthy donors provided by EFS (Etablissement Français du Sang).

Human PBMCs were first isolated from buffy coat of healthy donors from Etablissement Français du Sang (EFS): blood was first collected in a 50 mL falcon tube. 15 mL of Ficoll-Plaque™ PLUS 96% (GE Healthcare #17-1440-02) was added very gently at the bottom of a Sepmate tube, then blood added slowly in the tube before centrifugation at 1300 g for 10 minutes. The PBMC ring was then collected and washed with 50 mL PBS buffer, and another round of centrifugation at 300 g for 5 minutes was performed. The washing process was repeated two times before PBMC staining with anti-CD14 magnetic beads according to manufacturer's instructions (Miltenyi; ref 130-050-201): 15 minutes incubation at 4° C. before positive selection through the AutoMACS pro. Monocytes were collected and then washed with 50 mL PBS. Monocytes were cultured for 7 days in RPMI1640 (Invitrogen #11875-093), 10% FBS (Invitrogen #10500-056), 2% Human inactivated serum (Fisher Bioreagents #14-490E), 50 ng/ml Granulocyte-macrophage colony-stimulating factor (GM-CSF) (Miltenyi #130-093-866) in a T150 flask at 37° C. and 5% CO$_2$. After 7 days culture, monocytes differentiated into macrophages.

To collect macrophages, accutase (ThermoFisher, ref: A1110501) was used to detach cells (15 minutes at 37° C.), then 20 mL of complete culture medium RPMI1640, 10% FBS, 1% L-Glutamine (Invitrogen #25030) was added to stop its activity.

Collected cells were centrifuged at 350 g for 10 minutes followed by a wash in 20 mL PBS and another round of centrifugation at 350 g for 10 minutes.

20×10$^6$ macrophages were resuspended in 2 ml of diluent C (provided in the staining kit #PKH26GL-1KT from Sigma Aldrich) plus 10 µl of PKH26 (Sigma Aldrich #PKH26GL-1KT) for 5 minutes incubation in the dark at 37° C. 10 mL FBS were then added to inactivate the staining process for 1 minute, before completing to 50 mL with RPMI1640 10% FBS. Volume was adjusted to reach 1.5×10$^6$/ml macrophages concentration corresponding to 0.15 cells/100 µl.

20×10$^6$ MM.1R cells were resuspended in 2 ml of diluent C (provided in the staining kit #PKH26GL-1KT from Sigma Aldrich) plus 10 µl of PKH67 (Sigma Aldrich #PKH67GL-1KT) for 5 minutes incubation in the dark at 37° C. 10 mL FBS were then added to inactivate the staining process for 1 minute, before completing to 50 mL with RPMI1640 10% FBS. Volume was adjusted to reach 0.5×10$^6$/ml macrophages concentration corresponding to 0.05 cells/100 µl.

5×10$^4$ MM.1R cells/well were then incubated at 37° C. and 5% CO$_2$ for 15 minutes in a U-bottom 96-well polypropylene plate with the different antibodies at different concentrations, then macrophages were added at a macrophage/tumor cell ratio set at 3:1 (150,000 macrophages versus 50,000 MM.1R) overnight. ADCP assay was performed in the presence of 1 mg/mL human polyclonal IgG (Sigma #14506) to mimic physiological conditions.

The compounds 11-DE-DSB, anti-CD38-IgG1 and an isotype IgG1 DE-DSB were tested at final concentrations ranging from 100 ng/mL to 0.1 µg/mL (1/10 serial dilution in PBS Dulbecco's). ADCP activity of 11-DE-DSB, anti-CD38-IgG1 and an isotype IgG1 DE-DSB was read by flow cytometry. The % of MM.1R cells phagocytized by macrophages has been determined. Dose effect curves were fitted using the 4-parameter logistic model according to Ratkovsky and Reedy (Biometrics. 1986. September; 42(3):575-82). The adjustment was obtained by non-linear regression using the Marquardt algorithm. The relative EC50 corresponds to the concentration which produces half effect between max and min percentage of cell lysis. If the relative EC50 is out of range, relative EC50 is either more than the strongest concentration tested or below the weakest concentration tested, depending on the case. The geometric mean of the $EC50_{rel}$ values was calculated with confidence intervals (CI) at 95% level.

Figure 12:
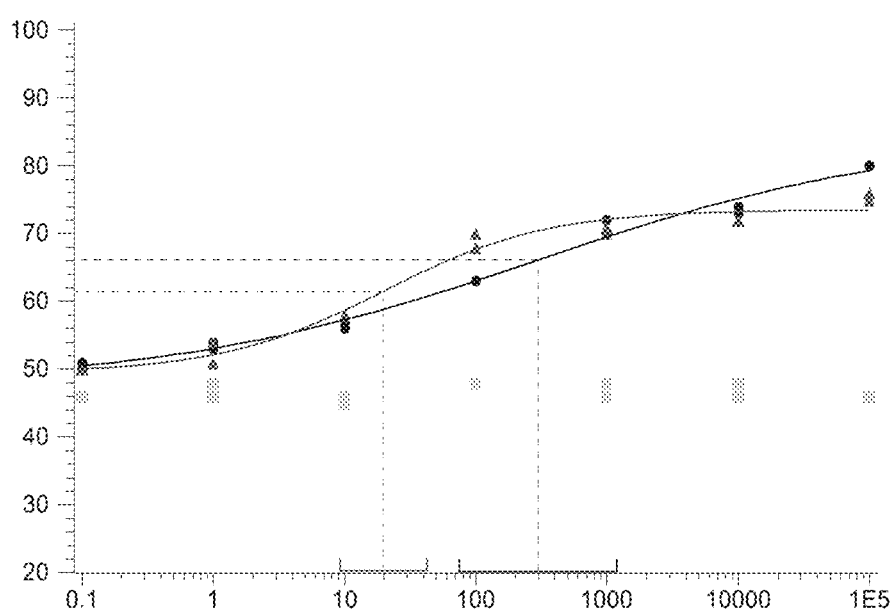
FIG. 12 shows dose-response curves for ADCP activity of 11-DE-DSB against MM.1R cells of five healthy donors. Closed circles: 11-DE-DSB, closed triangles: anti-CD38-IgG1, closed squares: isotype control. X axis: concentration (pM) y axis: % of lysis. Panel A: healthy donor 1, Panel B: healthy donor 2, Panel C: healthy donor 3, Panel D: healthy donor 4, and Panel E: healthy donor 5.
Figure 12:
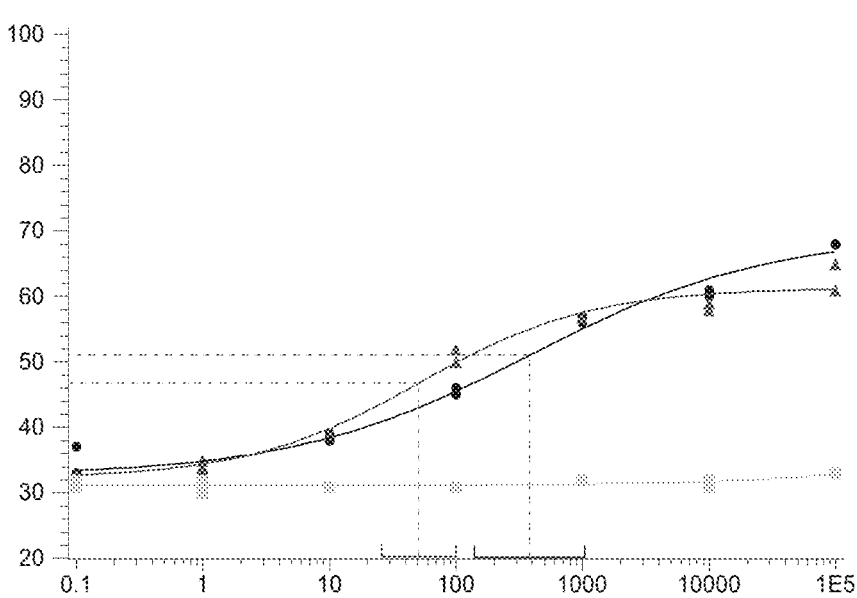
Figure 12:
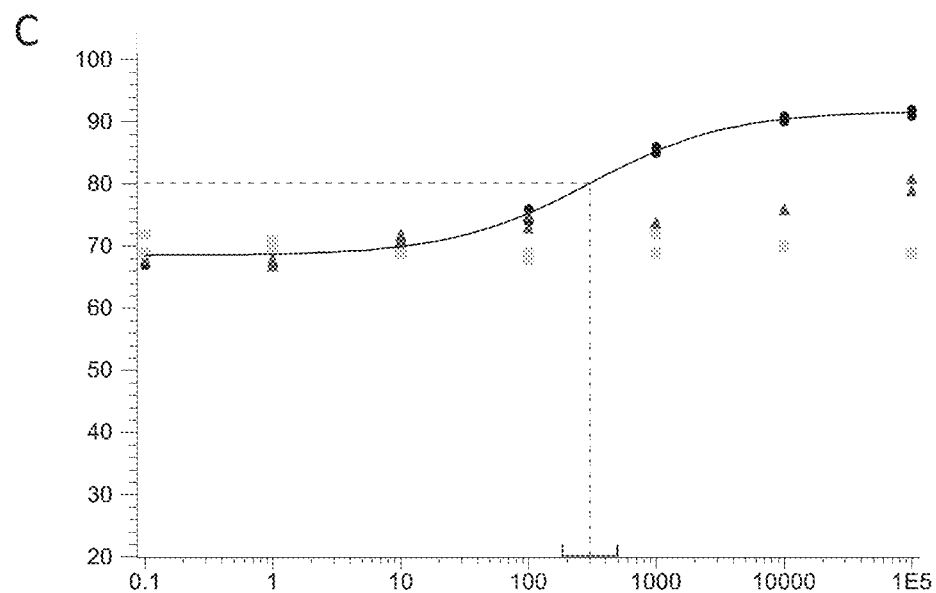
Figure 12:
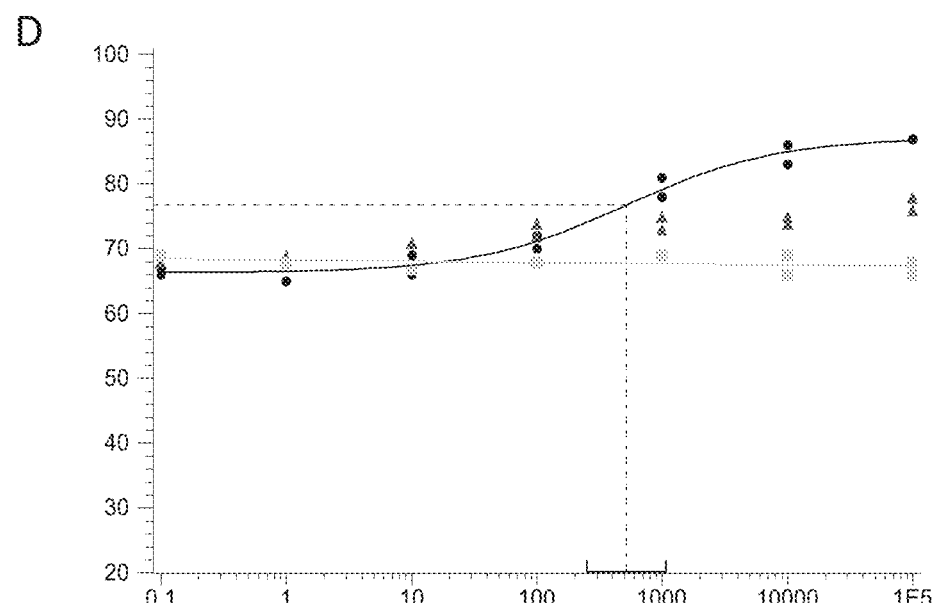
Figure 12:
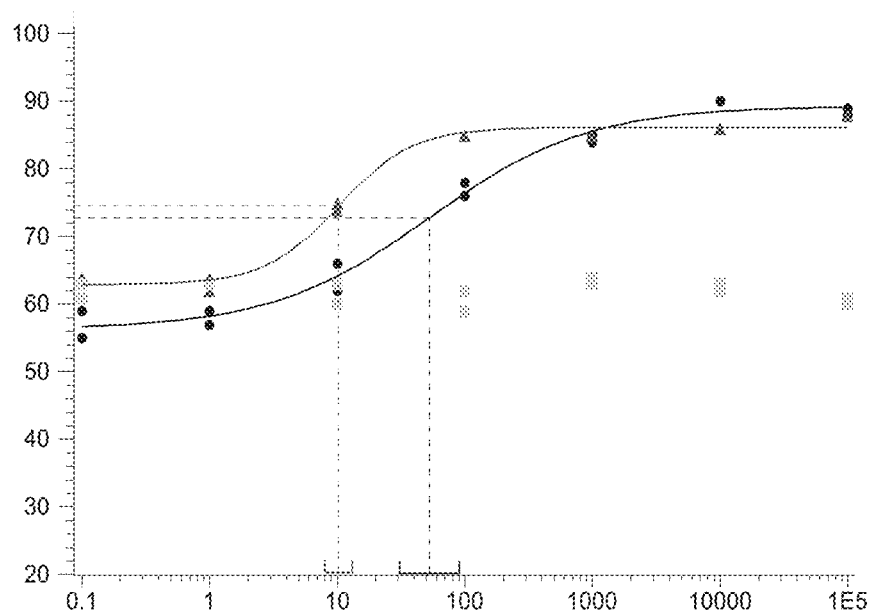

11-DE-DSB exhibited an ADCP activity against MM.1R cell line with a geometric mean of $EC50_{rel}$ of 247.8 pM [CI95% 81.7; 751.1](equivalent to 35.93 ng/mL) (n=5). In the same experiment, anti-CD38-IgG1 exhibited an ADCP activity against MM.1R cell line with a geometric mean of $EC50_{rel}$ of 21.7 pM [CI95% 2.9; 160.2](equivalent to 3.15 ng/ml) (n=3). The isotype control didn't show any ADCP activity. Results are summarized in Table 13.1 and Table 13.2; Dose-response curves of compounds for each donor are described in FIG. 12. In conclusion, 11-DE-DSB induced ADCP against GPRC5D-expressing MM.1R cell line with an EC50rel value of 248 pM [CI95% 82; 751].

TABLE 13.1

ADCP activity of 11-DE-DSB against MM.1R cells (5 healthy donors): $EC50_{rel}$ evaluation

| # Donor | EC50 rel | EC50 rel (LCI95%) | EC50 rel (UCI95%) | EC50 rel (CV) | Top [CI95%] | Bottom [CI95%] | Slope [CI95%] |
|---|---|---|---|---|---|---|---|
| 1 Donor1 | 296.7 | 74.45 | 1183 | 68.5% | 84.73 [75.91; 93.55] | 47.50 [41.84; 53.16] | 0.3044 [0.1382; 0.4707] |
| 2 Donor2 | 380.8 | 138.7 | 1045 | 47.7% | 69.46 [63.12; 75.79] | 32.64 [28.92; 36.36] | 0.4610 [0.2401; 0.6818] |
| 3 Donor3 | 303.1 | 184.7 | 497.3 | 22.5% | 91.81 [89.90; 93.73] | 68.52 [67.11; 69.94] | 0.7992 [0.5254; 1.073] |
| 4 Donor4 | 516.9 | 249.0 | 1073 | 33.7% | 87.16 [84.44; 89.88] | 66.34 [64.66; 68.02] | 0.7251 [0.3770; 1.073] |
| 5 Donor5 | 52.76 | 30.87 | 90.17 | 24.4% | 89.37 [87.11; 91.62] | 56.31 [53.56; 59.07] | 0.6990 [0.4542; 0.9438] |

TABLE 13.2

ADCP activity of 11-DE-DSB, anti-CD38-IgG1 and isotype control against MM.1R cells: $EC50_{rel}$ mean

| Compound | Donor | EC50 (pM) | EC50 geometric mean [CI95%] (pM) |
|---|---|---|---|
| 11-DE-DSB | Donor1 | 296.7 | 2.478E+02 [8.174E+01; 7.511E+02] (n = 5) |
| | Donor2 | 380.8 | |
| | Donor3 | 303.1 | |
| | Donor4 | 516.9 | |
| | Donor5 | 52.76 | |
| anti-CD38-IgG$_1$ | Donor1 | 19.73 | 2.171E+01 [2.942E+00; 1.602E+02] (n = 3) |
| | Donor2 | 50.70 | |
| | Donor3 | N/A | |
| | Donor4 | N/A | |
| | Donor5 | 10.23 | |
| Isotype control | Donor1 | N/A | N/A |
| | Donor2 | >1.000E+05 | |
| | Donor3 | N/A | |
| | Donor4 | <0.1000 | |
| | Donor5 | N/A | |

Sequences

| SEQ | Description | Sequence |
|---|---|---|
| 1 | 11 HCDR-1 | GFTVSSNY |
| 2 | 11 HCDR-2 | IYSGGST |
| 3 | 11 HCDR-3 | ARGFLAFGRYYYGMDV |
| 4 | 11 LCDR-1 | SSNIGSNY |
| 5 | 11 LCDR-2 | RNN |
| 6 | 11 LCDR-3 | AAWDDSLSGDV |
| 7 | 11 VH | EVQLVESGGGLVQPGGSLRLSCAASGFTVSSNYMSWVRQAPGKGLEWV SVIYSGGSTYYADSVKGRFTISRDNSKNTLYLQMNSLRAEDTAVYYCA RGFLAFGRYYYGMDVWGQGTTVTSS |

| SEQ | Description | Sequence |
|---|---|---|
| 8 | 11 VL | QSVLTQPPSASGTPGQRVTISCSGSSSNIGSNYVYWYQQLPGTAPKLL IYRNNQRPSGVPDRESGSKSGTSASLAISGLRSEDEADYYCAAWDDSL SGDVFGGGTKLTVL |
| 9 | 11 HC | EVQLVESGGGLVQPGGSLRLSCAASGFTVSSNYMSWVRQAPGKGLEWV SVIYSGGSTYYADSVKGRFTISRDNSKNTLYLQMNSLRAEDTAVYYCA RGFLAFGRYYYGMDVWGQGTTVTVSSASTKGPSVFPLAPSSKSTSGGT AALGCLVKDYFPEPVTVSWNSGALTSGVHTFPAVLQSSGLYSLSSVVT VPSSSLGTQTYICNVNHKPSNTKVDKKVEPKSCDKTHTCPPCPAPELL GGPSVFLFPPKPKDTLMISRTPEVTCVVVDVSHEDPEVKFNWYVDGVE VHNAKTKPREEQYNSTYRVVSVLTVLHQDWLNGKEYKCKVSNKALPAP IEKTISKAKGQPREPQVYTLPPSRDELTKNQVSLTCLVKGFYPSDIAV EWESNGQPENNYKTTPPVLDSDGSFFLYSKLTVDKSRWQQGNVFSCSV MHEALHNHYTQKSLSLSPG |
| 10 | 11 HC with Fc mutations (DE-DSB) | EVQLVESGGGLVQPGGSLRLSCAASGFTVSSNYMSWVRQAPGKGLEWV SVIYSGGSTYYADSVKGRFTISRDNSKNTLYLQMNSLRAEDTAVYYCA RGFLAFGRYYYGMDVWGQGTTVTVSSASTKGPSVFPLAPSSKSTSGGT AALGCLVKDYFPEPVTVSWNSGALTSGVHTFPAVLQSSGLYSLSSVVT VPSSSLGTQTYICNVNHKPSNTKVDKKVEPKSCDKTHTCPPCPAPELL GGPDVFLFPPKPKDTLMISRTPEVTCVVVDVSHEDPEVKFNWYVDGVE VHNAKTKPCEEQYNSTYRCVSVLTVLHQDWLNGKEYKCKVSNKALPAP EEKTISKAKGQPREPQVYTLPPSRDELTKNQVSLTCLVKGFYPSDIAV EWESNGQPENNYKTTPPVLDSDGSFFLYSKLTVDKSRWQQGNVFSCSV MHEALHNHYTQKSLSLSPG |
| 11 | 11 LC | QSVLTQPPSASGTPGQRVTISCSGSSSNIGSNYVYWYQQLPGTAPKLL IYRNNQRPSGVPDRFSGSKSGTSASLAISGLRSEDEADYYCAAWDDSL SGDVFGGGTKLTVLGQPKAAPSVTLFPPSSEELQANKATLVCLISDFY PGAVTVAWKADSSPVKAGVETTTPSKQSNNKYAASSYLSLTPEQWKSH RSYSCQVTHEGSTVEKTVAPTECS |
| 12 | human GPRC5D | MYKDCIESTGDYFLLCDAEGPWGIILESLAILGIVVTILLLLAFLFLM RKIQDCSQWNVLPTQLLFLLSVLGLEGLAFAFIIELNQQTAPVRYFLF GVLFALCFSCLLAHASNLVKLVRGCVSFSWTTILCIAIGCSLLQIIIA TEYVTLIMTRGMMFVNMTPCQLNVDFVVLLVYVLELMALTFFVSKATF CGPCENWKQHGRLIFITVLESIIIWVVWISMLLRGNPQFQRQPQWDDP VVCIALVTNAWVELLLYIVPELCILYRSCRQECPLQGNACPVTAYQHS FQVENQELSRARDSDGAEEDVALTSYGTPIQPQTVDPTQECFIPQAKL SPQQDAGGV |
| 13 | (Gly4-Ser)n | (GGGGS)$_n$, n = 1 to 35 |
| 14 | human GPRC5A | MATTVPDGCRNGLKSKYYRLCDKAEAWGIVLETVATAGVVTSVAFMLT LPILVCKVQDSNRRKMLPTQFLFLLGVLGIFGLTFAFIIGLDGSTGPT RFFLFGILFSICFSCLLAHAVSLTKLVRGRKPLSLLVILGLAVGFSLV QDVIAIEYIVLTMNRTNVNVESELSAPRRNEDFVLLLTYVLELMALTE LMSSFTFCGSFTGWKRHGAHIYLTMLLSIAIWVAWITLLMLPDEDRRW DDTILSSALAANGWVELLAYVSPEFWLLTKQRNPMDYPVEDAFCKPQL VKKSYGVENRAYSQEEITQGFEETGDTLYAPYSTHEQLNQPPQKEFS IPRAHAWPSPYKDYEVKKEGSEYMPME |
| 15 | human GPRC5D- human GPRC5A chimera (Nterm) | MATTVPDGCRNGLKSKYYRLCDKAEAWGIVLESLAILGIVVTILLLLA FLFLMRKIQDCSQWNVLPTQLLFLLSVLGLFGLAFAFIIELNQQTAPV RYFLFGVLFALCFSCLLAHASNLVKLVRGCVSFSWTTILCIAIGCSLL QIIIATEYVTLIMTRGMMFVNMTPCQLNVDFVVLLVYVLELMALTFFV SKATFCGPCENWKQHGRLIFITVLESIIIWVVWISMLLRGNPQFQRQP QWDDPVVCIALVTNAWVELLLYIVPELCILYRSCRQECPLQGNACPVT AYQHSFQVENQELSRARDSDGAEEDVALTSYGTPIQPQTVDPTQECFI PQAKLSPQQDAGGVEYMPME |
| 16 | human GPRC5D- human GPRC5A chimera (85-93) | MYKDCIESTGDYFLLCDAEGPWGIILESLAILGIVVTILLLLAFLFLM RKIQDCSQWNVLPTQLLFLLSVLGLFGLAFAFIIELDGSTGPTRFFLE GVLFALCESCLLAHASNLVKLVRGCVSFSWTTILCIAIGCSLLQIIIA TEYVTLIMTRGMMFVNMTPCQLNVDFVVLLVYVLELMALTFFVSKATE CGPCENWKQHGRLIFITVLESIIIWVVWISMLLRGNPQFQRQPQWDDP VVCIALVTNAWVELLLYIVPELCILYRSCRQECPLQGNACPVTAYQHS FQVENQELSRARDSDGAEEDVALTSYGTPIQPQTVDPTQECFIPQAKL SPQQDAGGVEYMPME |
| 17 | human GPRC5D- human GPRC5A chimera (145- | MYKDCIESTGDYFLLCDAEGPWGIILESLAILGIVVTILLLLAFLFLM RKIQDCSQWNVLPTQLLFLLSVLGLEGLAFAFIIELNQQTAPVRYFLE GVLFALCESCLLAHASNLVKLVRGCVSFSWTTILCIAIGCSLLQIIIA IEYIVLTMNRTNVNVESELSAPRRNVDFVLLVYVFLMALTFFVSKA TFCGPCENWKQHGRLIFITVLFSIIIWVVWISMLLRGNPQFQRQPQWD |

Sequences

| SEQ | Description | Sequence |
|---|---|---|
| | 167 | DPVVCIALVTNAWVELLLYIVPELCILYRSCRQECPLQGNACPVTAYQ HSFQVENQELSRARDSDGAEEDVALTSYGTPIQPQTVDPTQECFIPQA KLSPQQDAGGVEYMPME |
| 18 | human GPRC5D-human GPRC5A chimera (226-239) | MYKDCIESTGDYFLLCDAEGPWGIILESLAILGIVVTILLLLAFLFLM RKIQDCSQWNVLPTQLLFLLSVLGLFGLAFAFIIELNQQTAPVRYELF GVLFALCESCLLAHASNLVKLVRGCVSFSWTTILCIAIGCSLLQIIIA TEYVTLIMTRGMMFVNMTPCQLNVDFVVLLVYVLFLMALTFFVSKATF CGPCENWKQHGRLIFITVLESIIIWVVWISMLLLPDFDRRWDDPVVCI ALVTNAWVELLLYIVPELCILYRSCRQECPLQGNACPVTAYQHSFQVE NQELSRARDSDGAEEDVALTSYGTPIQPQTVDPTQECFIPQAKLSPQQ DAGGVEYMPME |

SEQ = SEQ ID NO.

The invention claimed is:

1. An anti-G Protein-Coupled Receptor Class C Group 5 Member D (GPRC5D) antigen-binding protein comprising two variable domains, the first variable domain comprising an HCDR1 of SEQ ID NO: 1, an HCDR2 of SEQ ID NO: 2 and an HCDR3 of SEQ ID NO: 3, and the second variable domain comprising an LCDR1 of SEQ ID NO: 4, an LCDR2 of SEQ ID NO: 5 and an LCDR3 of SEQ ID NO: 6.

2. The antigen-binding protein of claim 1, comprising a heavy chain variable domain (VH) amino acid sequence at least 90% identical to the amino acid sequence of SEQ ID NO: 7, and a light chain variable domain (VL) amino acid sequence at least 90% identical to the amino acid sequence of SEQ ID NO: 8.

3. The antigen-binding protein of claim 1, wherein the antigen-binding protein is an antibody, wherein the antibody is of human IgG isotype.

4. The antigen-binding protein of claim 3, wherein the antibody is of human IgG1 isotype subclass.

5. The antigen-binding protein of claim 1, wherein the antigen-binding protein is an antibody comprising at least one Fc domain mutation.

6. The antigen-binding protein of claim 5, wherein the antibody comprises at least one Fc domain mutation that enhances binding of the antibody to human FcγRIIIa.

7. The antigen-binding protein of claim 5, wherein the antibody comprises at least one Fc domain mutation at position 239 and/or position 332 that enhances binding of the antibody to human FcγRIIIa.

8. The antigen-binding protein of claim 7, wherein the antibody comprises
 a) Fc domain mutation S239D (Eu numbering),
 b) Fc domain mutation I332E (Eu numbering), or
 c) a) and b).

9. The antigen-binding protein of claim 5, wherein the antibody comprises at least one Fc domain mutation that enhances antibody stability.

10. The antigen-binding protein of claim 5, wherein the antibody comprises a pair of Fc domain mutations to cysteines.

11. The antigen-binding protein of claim 5, wherein the Fc domain mutations are at positions 292 and 302 (Eu numbering).

12. The antigen-binding protein of claim 11, wherein the Fc domain mutations are R292C and V302C (Eu numbering).

13. The antigen-binding protein of claim 1, wherein the antigen-binding protein is an afucosylated antibody.

14. The antigen-binding protein of claim 1, comprising
 a) a heavy chain (HC) amino acid sequence and a light chain (LC) amino acid sequence that are at least 90% identical to the amino acid sequences of SEQ ID NOs: 9 and 11, respectively; or
 b) an HC amino acid sequence and an LC amino acid sequence that are at least 90% identical to the amino acid sequences of SEQ ID NOs: 10 and 11, respectively.

15. The antigen-binding protein of claim 4, comprising an HC that comprises SEQ ID NO: 9 and an LC that comprises SEQ ID NO: 11.

16. The antigen-binding protein of claim 1, wherein said antigen-binding protein is a fusion protein.

17. The antigen-binding protein of claim 1, wherein said antigen-binding protein is bispecific or multispecific.

18. A pharmaceutical composition comprising the antigen-binding protein of claim 1 and a pharmaceutically acceptable excipient.

19. An antigen-binding protein comprising a heavy chain that comprises SEQ ID NO: 9 and a light chain that comprises SEQ ID NO: 11, wherein the antigen-binding protein is an afucosylated antibody.

20. An antigen-binding protein comprising an antibody that comprises a heavy chain comprising SEQ ID NO: 10 and a light chain comprising SEQ ID NO: 11.

* * * * *

UNITED STATES PATENT AND TRADEMARK OFFICE
CERTIFICATE OF CORRECTION

PATENT NO. : 12,286,475 B2
APPLICATION NO. : 18/790955
DATED : April 29, 2025
INVENTOR(S) : Remy et al.

It is certified that error appears in the above-identified patent and that said Letters Patent is hereby corrected as shown below:

In the Specification

At Column 2, Line 33, replace "1322E" with --I322E--

Column 8, Lines 15-29, should appear as follows:
(SEQ ID NO: 12)
MYKDCIESTG DYFLLCDAEG PWGIILESLA ILGIVVTILL
LLAFLFLMRK IQDCSQWNVL PTQLLFLLSV LGLFGLAFAF
IIELNQQTAP VRYFLFGVLF ALCFSCLLAH ASNLVKLVRG
CVSFSWTTIL CIAIGCSLLQ IIIATEYVTL IMTRGMMFVN
MTPCQLNVDF VVLLVYVLFL MALTFFVSKA TFCGPCENWK
QHGRLIFITV LFSIIIWVVW ISMLLRGNPQ FQRQPQWDDP
VVCIALVTNA WVFLLLYIVP ELCILYRSCR QECPLQGNAC
PVTAYQHSFQ VENQELSRAR DSDGAEEDVA LTSYGTPIQP
QTVDPTQECF IPQAKLSPQQ DAGGV At Column 9, Line 7, replace "lambda (δ)" with --lambda (λ)--

At Column 9, Line 38, replace "αγ and γδ forms" with --αβ and γδ forms--

At Column 14, Line 9, replace "Fc receptors" with --Fcγ receptors--

At Column 16, Lines 57-59, replace "A x light chain constant region can be changed, e.g., to a X light chain constant region, or vice-versa" with --A κ light chain constant region can be changed, e.g., to a λ light chain constant region, or vice-versa--

At Column 19, Line 13, replace "TL-8" with --IL-8--

Page 1 of 4

Signed and Sealed this
Eleventh Day of November, 2025

John A. Squires
*Director of the United States Patent and Trademark Office*

CERTIFICATE OF CORRECTION (continued)
U.S. Pat. No. 12,286,475 B2

At Column 35, Line 50, replace "36 µM" with --36 pM--

At Column 35, Line 53, replace "(relEC50 (of 154 and 1,663 pM, respectively)" with --(relEC50 of 154 and 1,663 pM, respectively)--

At Column 40, Line 59, replace "Example 9: ADCC-Enhanced Fe Engineered" with --Example 9: ADCC-Enhanced Fc Engineered--

At Column 52, Line 57, replace "(Sigma # 14506)" with --(Sigma # I4506)--

At Column 52, Line 60, replace "0.1 µg/mL" with --0.1 pg/mL--

Column 55, Sequence 8 should appear as follows:
QSVLTQPPSASGTPGQRVTISCSGSSSNIGSNYVYWYQQLPGTAPKLL
IYRNNQRPSGVPDRFSGSKSGTSASLAISGLRSEDEADYYCAAWDDSL
SGDVFGGGTKLTVL Column 55, Sequence 9 should appear as follows:
EVQLVESGGGLVQPGGSLRLSCAASGFTVSSNYMSWVRQAPGKGLEWV
SVIYSGGSTYYADSVKGRFTISRDNSKNTLYLQMNSLRAEDTAVYYCA
RGFLAFGRYYYGMDVWGQGTTVTVSSASTKGPSVFPLAPSSKSTSGGT
AALGCLVKDYFPEPVTVSWNSGALTSGVHTFPAVLQSSGLYSLSSVVT
VPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSV
MHEALHNHYTQKSLSLSPG Column 55, Sequence 10 should appear as follows:
EVQLVESGGGLVQPGGSLRLSCAASGFTVSSNYMSWVRQAPGKGLEWV
SVIYSGGSTYYADSVKGRFTISRDNSKNTLYLQMNSLRAEDTAVYYCA
RGFLAFGRYYYGMDVWGQGTTVTVSSASTKGPSVFPLAPSSKSTSGGT
AALGCLVKDYFPEPVTVSWNSGALTSGVHTFPAVLQSSGLYSLSSVVT
VPSSSLGTQTYICNVNHKPSNTKVDKKVEPKSCDKTHTCPPCPAPELL
GGPDVFLFPPKPKDTLMISRTPEVTCVVVDVSHEDPEVKFNWYVDGVE
VHNAKTKPCEEQYNSTYRCVSVLTVLHQDWLNGKEYKCKVSNKALPAP
EEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSV
MHEALHNHYTQKSLSLSPG Column 55, Sequence 11 should appear as follows:
QSVLTQPPSASGTPGQRVTISCSGSSSNIGSNYVYWYQQLPGTAPKLL

CERTIFICATE OF CORRECTION (continued)
U.S. Pat. No. 12,286,475 B2

IYRNNQRPSGVPDRFSGSKSGTSASLAISGLRSEDEADYYCAAWDDSL
SGDVFGGGTKLTVLGQPKAAPSVTLFPPSSEELQANKATLVCLISDFY
PGAVTVAWKADSSPVKAGVETTTPSKQSNNKYAASSYLSLTPEQWKSH
RSYSCQVTHEGSTVEKTVAPTECS

Column 55, Sequence 12 should appear as follows:
MYKDCIESTGDYFLLCDAEGPWGIILESLAILGIVVTILLLLAFLFLM
RKIQDCSQWNVLPTQLLFLLSVLGLFGLAFAFIIELNQQTAPVRYFLF
GVLFALCFSCLLAHASNLVKLVRGCVSFSWTTILCIAIGCSLLQIIIA
TEYVTLIMTRGMMFVNMTPCQLNVDFVVLLVYVLFLMALTFFVSKATF
CGPCENWKQHGRLIFITVLFSIIIWVVWISMLLRGNPQFQRQPQWDDP
VVCIALVTNAWVFLLLYIVPELCILYRSCRQECPLQGNACPVTAYQHS
FQVENQELSRARDSDGAEEDVALTSYGTPIQPQTVDPTQECFIPQAKL
SPQQDAGGV Column 55, Sequence 14 should appear as follows:
MATTVPDGCRNGLKSKYYRLCDKAEAWGIVLETVATAGVVTSVAFMLT
LPILVCKVQDSNRRKMLPTQFLFLLGVLGIFGLTFAFIIGLDGSTGPT
RFFLFGILFSICFSCLLAHAVSLTKLVRGRKPLSLLVILGLAVGFSLV
QDVIAIEYIVLTMNRTNVNVFSELSAPRRNEDFVLLLTYVLFLMALTF
LMSSFTFCGSFTGWKRHGAHIYLTMLLSIAIWVAWITLLMLPDFDRRW
DDTILSSALAANGWVFLLAYVSPEFWLLTKQRNPMDYPVEDAFCKPQL
VKKSYGVENRAYSQEEITQGFEETGDTLYAPYSTHFQLQNQPPQKEFS
IPRAHAWPSPYKDYEVKKEGSEYMPME Column 55, Sequence 15 should appear as follows:
MATTVPDGCRNGLKSKYYRLCDKAEAWGIVLESLAILGIVVTILLLLA
FLFLMRKIQDCSQWNVLPTQLLFLLSVLGLFGLAFAFIIELNQQTAPV
RYFLFGVLFALCFSCLLAHASNLVKLVRGCVSFSWTTILCIAIGCSLL
QIIIATEYVTLIMTRGMMFVNMTPCQLNVDFVVLLVYVLFLMALTFFV
SKATFCGPCENWKQHGRLIFITVLFSIIIWVVWISMLLRGNPQFQRQP
QWDDPVVCIALVTNAWVFLLLYIVPELCILYRSCRQECPLQGNACPVT
AYQHSFQVENQELSRARDSDGAEEDVALTSYGTPIQPQTVDPTQECFI
PQAKLSPQQDAGGVEYMPME Column 55, Sequence 16 should appear as follows:
MYKDCIESTGDYFLLCDAEGPWGIILESLAILGIVVTILLLLAFLFLM
RKIQDCSQWNVLPTQLLFLLSVLGLFGLAFAFIIELDGSTGPTRFFLF
GVLFALCFSCLLAHASNLVKLVRGCVSFSWTTILCIAIGCSLLQIIIA
TEYVTLIMTRGMMFVNMTPCQLNVDFVVLLVYVLFLMALTFFVSKATF
CGPCENWKQHGRLIFITVLFSIIIWVVWISMLLRGNPQFQRQPQWDDP
VVCIALVTNAWVFLLLYIVPELCILYRSCRQECPLQGNACPVTAYQHS

FQVENQELSRARDSDGAEEDVALTSYGTPIQPQTVDPTQECFIPQAKL
SPQQDAGGVEYMPME

Column 55 and 57, Sequence 17 should appear as follows:
MYKDCIESTGDYFLLCDAEGPWGIILESLAILGIVVTILLLLAFLFLM
RKIQDCSQWNVLPTQLLFLLSVLGLFGLAFAFIIELNQQTAPVRYFLF
GVLFALCFSCLLAHASNLVKLVRGCVSFSWTTILCIAIGCSLLQIIIA
IEYIVLTMNRTNVNVFSELSAPRRNVDFVVLLVYVLFLMALTFFVSKA
TFCGPCENWKQHGRLIFITVLFSIIIWVVWISMLLRGNPQFQRQPQWD
DPVVCIALVTNAWVFLLLYIVPELCILYRSCRQECPLQGNACPVTAYQ
HSFQVENQELSRARDSDGAEEDVALTSYGTPIQPQTVDPTQECFIPQA
KLSPQQDAGGVEYMPME Column 57, Sequence 18 should appear as follows:
MYKDCIESTGDYFLLCDAEGPWGIILESLAILGIVVTILLLLAFLFLM
RKIQDCSQWNVLPTQLLFLLSVLGLFGLAFAFIIELNQQTAPVRYFLF
GVLFALCFSCLLAHASNLVKLVRGCVSFSWTTILCIAIGCSLLQIIIA
TEYVTLIMTRGMMFVNMTPCQLNVDFVVLLVYVLFLMALTFFVSKATF
CGPCENWKQHGRLIFITVLFSIIIWVVWISMLLLPDFDRRWDDPVVCI
ALVTNAWVFLLLYIVPELCILYRSCRQECPLQGNACPVTAYQHSFQVE
NQELSRARDSDGAEEDVALTSYGTPIQPQTVDPTQECFIPQAKLSPQQ
DAGGVEYMPME In the Claims Column 64, Lines 39-41 in Claim 15, Line 1, change "The antigen-binding portion of claim 4" to
--The antigen-binding protein of claim 14--